US009365622B2

(12) United States Patent
Schmidt et al.

(10) Patent No.: US 9,365,622 B2
(45) Date of Patent: Jun. 14, 2016

(54) METHODS AND COMPOSITIONS RELATED TO CYCLIC PEPTIDE SYNTHESIS

(75) Inventors: Eric W. Schmidt, Salt Lake City, UT (US); Brian Hathaway, Salt Lake City, UT (US); James T. Nelson, South Euclid, OH (US); Mohamed S. Donia, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1017 days.

(21) Appl. No.: 12/281,373

(22) PCT Filed: Mar. 1, 2007

(86) PCT No.: PCT/US2007/063089
§ 371 (c)(1),
(2), (4) Date: Jan. 21, 2009

(87) PCT Pub. No.: WO2007/103739
PCT Pub. Date: Sep. 13, 2007

(65) Prior Publication Data
US 2009/0215172 A1 Aug. 27, 2009

Related U.S. Application Data

(60) Provisional application No. 60/777,954, filed on Mar. 1, 2006.

(51) Int. Cl.
*C07K 14/00* (2006.01)
*C07K 5/12* (2006.01)
*C07K 7/02* (2006.01)
*C07K 7/06* (2006.01)
*C07K 7/64* (2006.01)

(52) U.S. Cl.
CPC . *C07K 14/00* (2013.01); *C07K 5/12* (2013.01); *C07K 7/02* (2013.01); *C07K 7/06* (2013.01); *C07K 7/64* (2013.01)

(58) Field of Classification Search
CPC .................................................... C07K 14/00
USPC .......................................................... 530/324
See application file for complete search history.

(56) References Cited

U.S. PATENT DOCUMENTS

| 3,610,795 | A | 10/1971 | Antoine |
| 4,342,566 | A | 8/1982 | Theofilopoulos |
| 4,816,567 | A | 3/1989 | Cabilly |
| 4,868,116 | A | 9/1989 | Morgan |
| 4,897,355 | A | 1/1990 | Epstein |
| 4,980,286 | A | 12/1990 | Morgan |
| 5,556,768 | A | 9/1996 | Yamashita |
| 5,565,332 | A | 10/1996 | Hoogenboom |
| 5,596,079 | A | 1/1997 | Smith |
| 5,721,367 | A | 2/1998 | Kay |
| 5,804,440 | A | 9/1998 | Burton |
| 5,824,520 | A | 10/1998 | Mulligan-Kehoe |
| 5,837,243 | A | 11/1998 | Deo |
| 5,939,598 | A | 8/1999 | Kuchrlpati |
| 6,031,071 | A | 2/2000 | Mandeville |
| 6,096,441 | A | 8/2000 | Hauser |
| 6,130,364 | A | 10/2000 | Jakobovits |
| 6,180,377 | B1 | 1/2001 | Morgan |
| 6,261,834 | B1 | 7/2001 | Srivastava |
| 2004/0014100 | A1 | 1/2004 | Lorenz et al. |
| 2005/0260626 | A1 | 11/2005 | Lorens et al. |

FOREIGN PATENT DOCUMENTS

| CA | 2345407 | 4/2000 |
| WO | WO89/07136 | 8/1989 |
| WO | WO90/02806 | 3/1990 |
| WO | WO92/03566 | 3/1992 |
| WO | WO93/22434 | 11/1993 |
| WO | WO94/29348 | 6/1994 |
| WO | WO94/19478 | 9/1994 |
| WO | WO95/24489 | 3/1995 |

OTHER PUBLICATIONS

Hsu, Joseph C. (Plant and Cell Physiology 13(4), 689-94, 1972).*
Schulze E (Comparative biochemistry and physiology. B, Comparative Biochemistry 103(4), 913-6, 1992).*
Bender, Margaret M. (Phytochemistry (Elsevier) 10(6), 1239-44, 1971).*
Gaffney J. S. (Biomedical Mass Spectrometry 5(8), 495-7, 1978).*
Abel-Santos E, Scott CP, Benkovic SJ, Use of inteins for the in vivo production of stable cyclic peptide libraries in *E. coli*, Methods Mol Biol. 205:281-94 (2003).
Baggiohni M, et al ., Interleukin-8, a chemotactic and inflammatory cytokine. FEBS Lett 307 97-101, (1992).
Banker, R., and S. Carmeli, Tenuecyclamides A-D, cyclic hexapeptides from the cyanobacterium *Nostoc spongiaforme* var. *tenue*, J. Nat. Prod. 61:1248-1251 (1998).
Baumann, Biology bacteriocyte-associated endosymbionts of plant sap-sucking insects, P Annu Rev Microbiol 59:155-189 (2005).
Biard, J.F., C. Grivois, J.F. Verbist, C. Debitus & J.B. Carre, Origin of bistramide A identified in *Lissoclinum bistratum* (Urochordata): possible involvement of symbiotic Prochlorophyta. J. Mar. Biol. Ass. U. K. 70:741-746 (1990).
Blunt, J. W., B. R. Copp, M. H. G. Munro, P. T. Northcote, and M. R. Prinsep. Marine natural products. Nat. Prod. Rep. 23:26-78 (2006).
Bourne GT, Nielson JL, Coughlan JF, Darwen P, Campitelli MR, Horton DA, Rhumann A, Love SG, Tran TT, Smythe MLA convenient method for synthesis of cyclic peptide libraries, Methods Mol Biol. 298:151-65 (2005).
Bout, Lung Gene Therapy: In Vivo Adenovirus-Mediated Gene Transfer to Rhesus Monkey Airway Epithelium, Human Gene Therapy 5:3-10 (1994).
Carmichael, W. W., Cyanobacteria secondary metabolites—the cyanotoxins. J Appl Bacteriol. 72(6):445-59 (1992).
Carroll, A.R. et al., Patellins 1-6 and Trunkamide A: Novel Cyclic Hexa-, Hepta- and Octa-peptides from Colonial Ascidians, *Lissoclinum* sp., Aust. J. Chem, 49(6):659-667 (1996).

(Continued)

*Primary Examiner* — David Lukton
(74) *Attorney, Agent, or Firm* — Ballard Spahr LLP; Scott Marty

(57) ABSTRACT

Disclosed are compositions and methods for cyclization of polymers such as peptides.

19 Claims, 53 Drawing Sheets

(56) References Cited

OTHER PUBLICATIONS

Choate KA, Kinsella TM, Wiliams ML, Nolan GP, Khavari PA. Transglutaminase 1 delivery to lamellar ichthyosis keratinocytes. Hum. Gene Ther 7:2247-53. (1996).
Cohen BA, Colas P, Brent R, An artificial cell-cycle inhibitor isolated from a combinatorial library, PNAS 1Proc Natl Acad Sci USA 95(24) 14272-7 (1998).
Davidson, B. S., Ascidians: producers of amino acid derived metabolites, Chem. Rev. 93, 1771-1791 (1993).
Davies et al., The cyclization of peptides and depsipeptides, J Peptide Sci 9(8):471-501 (2003).
Degnan, B. M., Hawkins, C. J., Lavin, M. F., McCaffrey, E. J., Parry, D. L., van den Brenk, A. L. & Watters, D. J. (1989. ) J. Med. Chem. 32, 1349-1354.
Devassy, V. P., P. M. Bhattathiri, and S. Z. Qasim. Succession of organisms following Trichodesmium phenomenon. Indian J. Mar. Sci. 8:88-93 (1979).
Donia M, Hathaway BJ, Sudek S, Haygood MG, Rosovitz MJ, Ravel J, Schmidt EW Natural combinatorial peptide libraries in cyanobacterial symbionts of marine ascidians, N at. Chem. Biol. 2:729-735 (2006).
Faulkner, D.J.; He, H.; Unson, M.D.; Bewley, C.A.; Garson, M.J. New metabolites from marine sponges: Are symbionts important? Gazz. Chim. Ital. 123, 301-307 (1993).
Feigner et al., Lipofection: A highly efficient, lipid-mediated DNA-transfection procedure. Proc Natl Acad Set USA 84 '413-7 '417 (1987).
Floss, Combinatorial biosynthesis—Potential and problems. Journal of Biotechnology 124 (2006) 242-257 (2006).
Fu, X., T. Do, F. J. Schmitz, V. Andrusevich, and M. H. Engel. 1998. New cyclic peptide from the ascidian Lissoclinum patella, J. Nat. Prod. 61:1547-1551 (1998).
Fuller, J. D., Camus, A. C., Duncan, C. L., Nizet, V., Bast, D. J., Thune, R. L., Low, D. E., de Azavedo, J. C. S., Identification of a Streptolysin S-Associated Gene Cluster and Its Role in the Pathogenesis of *Streptococcus iniae* Disease. Infect. Immun. 70:5730-5739 (2002).
Gehring, I. Mori, R. Perry, C. Walsh, The Nonribosomal Peptide Synthetase HMWP2 Forms a Thiazoline Ring During Biogenesis of Yersiniabactin, an Iron Chelating Virulence Factor of Y. pestis, Biochemistry 37:11637-11650 (1998).
Gerwick, W. H., L. T. Tan, and N. Sitachitta, Nitrogen-containing metabolites from marine cyanobacteria. Alkaloids Chem. Biol. 57:75-184, (2001).
Gonzalez-Pastor, J. E., San Millan, J. L., Castilla, M. A. & Moreno, F. Structure and Organization of Plasmid Genes Required to Produce the Translation Inhibitor Microcin. Journal of Bacteriology , p. 7131-7140 (Dec. 1995).
Guo C, P A, Tester Toxic effect of the bloom-forming *Tnchodesmium* sp (Cyanophyta) to the copepod Acartia tonsa, Nat Toxins 2 222-227 (1994).
Hahn J., Selective interaction between nonribosomal peptide synthetases is facilitated by short communication-mediating domains Chem Soc Perkm Trans 1307-314 (1982).
Hawser, S. P., E. J. Carpenter, G. A. Codd, and D. G. Capone, . A neurotoxic factor associated with the bloom-forming cyanobacterium Trichodesmium. Toxicon 29:277-278 (1991).
Hawser, S. P., J. M. O'Neil, M. R. Roman, and G. A. Codd., Toxicity of blooms of the cyanobacterium Trichodesmium to zooplankton, J. Appl. Phycol. 4:79-86 (1992).
Haygood, M.G.; Schmidt, E.W.; Davidson, S.K.; Faulkner, D.J. Microbial Symbionts of Marine Invertebrates: Opportunities for Microbial Biotechnology. J. Mol. Microbiol. Biotechnol. 1:33-34 (1999).
Hildebrand, M., L. Waggoner , H. Liu, S. Sudek, S. Allen, C. Anderson, D. Sherman, and M. Haygood, bryA: An Unusual Modular Polyketide Synthase Gene from the Uncultivated Bacterial Symbiont of the Marine Bryozoan Bugula neritina Chemistry and Biology, 11:1543-1552 (2004).

Hoogenboom et al, Human Antibodies from Synthetic Repertoires of Germline Vh Gene Segments Rearranged in Vitro. J Mol Biol. 227: 381 (1991).
Horswill AR, Benkovic SJ, Cyclic peptides, a chemical genetics tool for biologists, Cell Cycle, (4):552-5. Epub (2005).
Horton DA, Bourne GT, Smythe ML, Exploring privileged structures: the combinatorial synthesis of cyclic peptides, J Comput Aided Mol Des. 16(5-6):415-30 (2002).
Ibba and Hennecke, Towards engineering proteins by site directed incorporation in vivo of non natual amino acids. Review, Bio/technology, 12 678-682 (1994).
Ibba, Strategies for in vitro and in vivo translation with non-natural amino acids. Biotechnology & Genetic Engineering Reviews 13 197-216 (1995).
Ichinose, K., Bedford, D. J., Tornus, D., Bechthold, A., Bibb, M. J., Revill, W. P., Floss, H. G. & Hopwood, D. A. (1998) Chem. Biol. 5, 647-659.
Ireland CM, Durso AR, Newman RA and Hacker MP Antineoplastic cyclic peptides from the marine tunicate Lissoclinum patella. J Org Chem 47:1807-1811(1982).
Jack, R W & Jung, G, Lantibiotics and microcins: polypeptides with unusual chemical diversity, Curr Opm Chem Biol 4:310-317 (2000).
Karl, D., A. Michaels, B. Bergman, D. Capone, E. Carpenter, R. Letelier, F. Lipschultz, H. Paerl, D. Sigman, and L. Stal, Dinitrogen fixation in the world's oceans. Biogeochemistry 57/58:47-98 (2002).
Kimura R, Camarero JA, Expressed protein ligation: a new tool for the biosynthesis of cyclic polypeptides, Protein Pept Lett. 12(8):789-94 (2005).
Kinsella, T. M., Nolan, G. P., Episomal vectors rapidly and stably produce high-titer recombinant retrovirus. Hum. Gene Ther. 7:1405-1413 (1996).
Kirshenbaum, Highly efficient gene transfer into adult ventricular myocytes by recombinant adenovirus, J. Clin. Invest. 92:381-387 (1993).
Kleinkauf H, von Dohren H, Applications of peptide synthetases in the synthesis of peptide analogues, Acta Biochim Pol. 44(4):839-47 (1997).
Kline, T. C. and Lewin, R. A. Natural 15N/14N abundance as evidence for N2 fixation by *Prochloron* (Prochlorophyta) endosymbiotic with didemnid ascidians, Symbiosis 26:193-198 (1999).
Kobayashi and Ishibashi, Bioactive metabolites of symbiotic marine organisms, Chem. Rev. 93:1753-1770 (1993).
Koike, I., Yamamuro, M. & Pollard, P. C., Carbon and nitrogen budgets of two Ascidians and their symbiont, Prochloron, in a tropical seagrass meadow, Australian Journal of Marine and Freshwater Research, 44, 173-182 44, 173-182 (1993).
Lenes, et al., Iron fertilization and the Trichodesmium response on the West Florida shelf. Limnol. Oceanogr. 46: 1261-1277 (2001).
Letsinger et al , Cholesteryl-conjugated oligonucleotides: Synthesis, properties, and activity as inhibitors of replication of human immunodeficiency virus in cell culture Proc Natl Acad Sci USA, 86, 6553-6556 (1989).
Li, Y.-M., Milne, J. C., Madison, L. L., Kolter, R., Walsh, C. T., From Peptide Precursors to Oxazole and Thiazole-Containing Peptide Antibiotics: Microcin B17 Synthase. Science 274:1188-1193 (1996).
Litzinger and Huang, Biodistribution and immunotargetability of ganglioside-stabilized dioleoylphosphatidylethanolamine liposomes. Biochimica et Biophysica Acta, 1104: 179-187 (1992).
Long PF, Dunlap WC, Battershill CN, Jaspars M, Shotgun cloning and heterologous expression of the patellamide gene cluster as a strategy to achieving sustained metabolite production, Chembiochem 6(10):1760-1765 (2005).
Lusky, M L , et al , Bovine Papilloma Virus Contains an Activator of Gene Expression at the Distal End of the Early Transcription Unit. Molecular and Cellular Biology , p. 1108-1122 (Jun. 1983).
Madison, L. L. Vivas, E. I., Li, Yue-M, Walsh, C. T., and Kolter, R. Mol. Microbiol. 23, 161-168 (1997).
Milne J C , A C Eliot, N L Kelleher, C T Walsh, ATP/GTP hydrolysis is required for oxazole and thiazole biosynthesis m the peptide antibiotic microcosm B17 Biochemistry 37 13250-13261 (1998).
Milne, J. C., Roy, R. S., Eliot, A. C., Kelleher, N. L., Wokhlu, A., Nickels, B. & Walsh, C. T., Cofactor requirements and reconstitution

(56) References Cited

OTHER PUBLICATIONS of microcin B17 synthetase: a multienzyme complex that catalyzes the formation of oxazoles and thiazoles in the antibiotic microcin B17 Biochemistry 38, 4768-4781(1999).
Morley, J. S., Modulation of the Action of Regulatory Peptides by Structural Modification, Trends Pharm Sci., 463-468, (1980).
Namikoshi et al., Bioactive compounds produced by cyanobacteria J Ind Microbiol 17 373-384 (1996).
Newman DJ, Cragg GM: Marine natural products and related compounds in clinical and advanced preclinical trials. J Nat Prod 67:1216-1238 (2004).
Onaka H, M Nakaho, K Hayashi, Y Igarashi, T Furumai, Cloning and charactenzation of the goadsponn biosynthetic gene cluster from *Streptomyces* sp TP-A0584 Microbiology 151 3923-3933 (2005).
Pear et al, Production of high-titer helper-free retroviruses by transient transfection, PNAS USA 90(18) 8392-6 (1993).
Piel, J., Hui, D., Wen, G., Butzke, D., Platzer, M., Fusetani, N., Matsunaga, S., Antitumor polyketide biosynthesis by an uncultivated bacterial symbiont of the marine sponge *Theonella swinhoei*, Proc. Natl. Acad. Sci. USA 101:16222-16227 (2004).
Prufert-Bebout et al., Growth, nitrogen fixation, and spectral attenuation in cultivated *Trichodesmium* species, Appl. Environ. Microbiol. 59:1367-1375 (1993).
Rizo, J. & Gierasch, L.M., Constrained peptides—models of bioactive peptides and protein substructures, Ann. Rev. Biochem. 61:387-418 (1992).
Salomon, C. E. and Faulkner, D. J., Localization studies of bioactive cyclic peptides in the ascidian Lissoclinum patella, J. Nat. Prod. 65: 689-692 (2002).
Salvatella, X., J. M. Caba, F. Albericio, and E. Giralt, Solution of the antitumor candidate trunkamide A by 2D NMR restrained simulated annealing methods. J. Org. Chem. 68:211-215 (2003).
Schmidt, E. W., Nelson, J. T., Rasko, D. A., Sudek, S., Eisen, J. A., Haygood, M. G., Ravel, Patellamide A and C biosynthesis by a microcin-like pathway in Prochloron didemni, the cyanobacterial symbiont of Lissoclinum patella, J. Proc. Nat. Acad. Sci. USA, 102, 7315-7320 (2005).
Schmidt, E.W.; Sudek, S.; Haygood, M.G., Genetic evidence supports secondary metabolic diversity in *Prochloron* spp., the cyanobacterial symbiont of a tropical ascidian, J. Nat. Prod. 67:1341-1345 (2004).
Schnell, N., K.-D. Entian, U. Schneider, F. Götz, H. Zähner, R. Kellner, and G. Jung., Prepeptide sequence of epidermin, a ribosomally synthesized antibiotic with four sulphide-rings, Nature 333:276-278 (1988).
Scott CP, Abel-Santos E, Wall M, Wahnon DC, Benkovic SJ, Production of cyclic peptides and proteins in vivo, Proc Natl Acad Sci U S A. 96(24):13638-43 (1999).
Simmons, et al., Marine natural products as anticancer drugs, MoI Cancer Ther 4, 333-342 (2005).
Sings HL, Rinehart KL, Compounds produced from potential tunicate-blue-green algal symbiosis: a review, J Ind Microbiol Biotechnol 17: 385-396 (1996).
Solbiati, J. O., Ciaccio, M., Farías, R. N., González-Pastor, J. E., Moreno, F., Salomón, R. A., Sequence analysis of the four plasmid genes required to produce the circular peptide antibiotic microcin J25, J. Bacteriol. 181:2659-2662 (1999).
Sudek, S., Haygood, M. G., Youssef, D. T. A., Schmidt, E. W., Structure of Trichamide, a Cyclic Peptide from the Bloom-Forming Cyanobacterium Trichodesmium erythraeum, Predicted from the Genome Sequence.. Appl. Environ. Microbiol. 72: 4382-4387 (2006).
Swift, H. and D.L. Robertson, Structural aspects of a Prochloron-tunicate symbiosis. Symbiosis, 10:95-113 (1991).
Tan, L. T., Bioactive natural products from marine cyanobacteria for drug discovery. Phytochemistry 68:954-979 (2007).
Thorson et al, A Biosynthetic approach for the incorporation of unnatural amino acids into proteins. Methods in Molec Biol 77 43-73 (1991).
Tomitani, A., Okada, K., Miyashita, H., Matthijs, H. C. P., Ohno, T. & Tanaka, A., Chlorophyll b and phycobilins in the common ancestor of cyanobacteria and chloroplasts Nature 400, 159-162 (1999).
Trauger, et al., Peptide cyclization catalysed by the thioesterase domain of tyrocidine synthetase, Nature 407:215-218, (2000).
Williams et al., A marine natural product, patellamide D, reverses multidrug resistance in a human leukemic cell line, Cancer Lett 71, 97-102 (1993).
Wipf et al., Conformational studies and structure—activity analysis of lissoclinamide 7 and related cyclopeptide alkaloids, J Am Chem Soc 120, 4105-4112 (1998).
Withers et al., Pigment composition, photosynthesis and fine structure of a non-blue-green procaryotec algal symbiont (*Prochloron* sp_in a didemnid ascidian from Hawaiian waters, Phycologia 17, 167-171 (1978).
Withers, N. W., Alberte, R. S., Lewin, R. A., Thornber, J. P., Britton, G. & Goodwin, T. W., Photosynthetic unit size, carotenoids, and chlorophyll-protein composition of *Prochloron* sp., a prokaryotic green alga, Proc. Natl. Acad. Sci. USA 75, 2301-2305 (1978).
Yokoboria, Kurabayashib, Neilanc, Maruyamad and Hirose, Multiple origins of the ascidian-Prochloron symbiosis: Molecular phylogeny of photosymbiotic and non-symbiotic colonial ascidians inferred from 18S rDNA sequences, Molecular Phylogenetics and Evolution 40(1):8-19 (2006).
Zabriskie, Foster, Stout, Clardy and Ireland, Studies on the Solution and Solid State Structure of Patellin 2, J. Am. Chem. Soc. 112, 8080-8084 (1990).

* cited by examiner

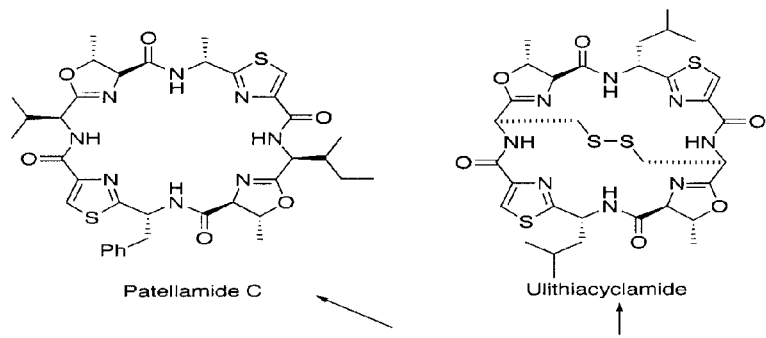
PatE2:  MNKKN(X)₃₁GLEASVTACITFCAYDGVEPSCTLCCTLCAYDGE
PatEdm: MNKKN(X)₃₁GLEASVTACITFCAYDGVEPSQGGRGDWPAYDGE
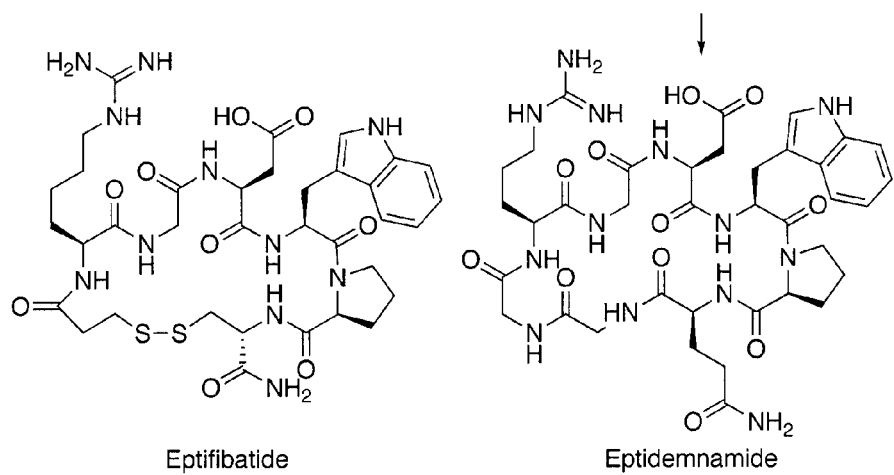
FIGURE 1

```
>PatE  MNKKNI--------LPQQGQPVIRTAGQLSSQLAELSEEALGDAGLEASVTACITFC---AYD
                                              ▶ GVEPSITVCISVC---AYDGE
>TriG  MGKKNIQPNSSQPVFRSLVARPALEELREENLTEGNQGHGPLANGPGPSGDGLHPRLCSCSYDGDDE
```

| COMPOUND | CODING SEQUENCE |
|---|---|
| patellamide C | V T A C I T F C |
| patellamide A | I T V C I S V C |
| ulithiacyclamide | C T L C C T L C |
| patellamide B | L T A C I T F C |
| lissoclinamide 2/3 | A C F P T I C |
| lissoclinamide 4/5 | F C F P T V C |
| new compound 1 | F I F A T V C |
| new compound 2 | S C F P T I C |
| new compound 3 | F I F P T V C |
| consensus | N N N N N T N C |

FIGURE 15
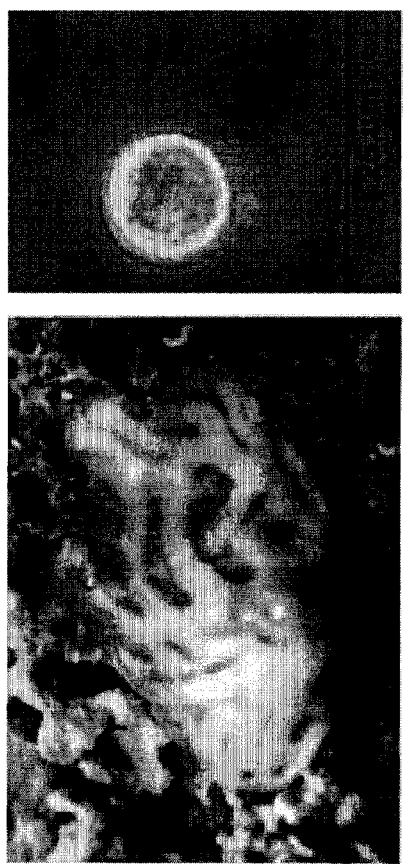
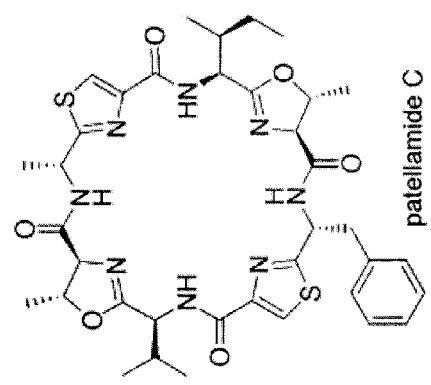
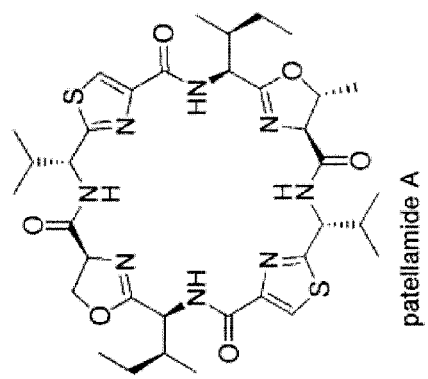

>PatE  MNKKNILPQQGQPVIRLTAGQLSSQLAEISEEALGDAGLEASVTACITFCAYD
GVEPSITVCISVCAYDGE

FIGURE 16

Marine Symbionts & Filamentous Fungi

A Family of Compounds
Figure 21

| Peptide | AA#1 | AA#2 | AA#3 | AA#4 | AA#5 | AA#6 | AA#7 | AA#8 | Source |
|---|---|---|---|---|---|---|---|---|---|
| 1 | Ccv | Val | Ccv | Phe | Tcv | Val | Pro | | D |
| 2 | Tcv | Val | Ccv | Phe | Ccv | Phe | Pro | | L |
| 3 | Tcv | Val | Ccv | Ile | Tcv | Val | Ccv | Ile | ? |
| 4 | Scv | Val | Ccv | Ile | Tcv | Val | Ccv | Ile | L |
| 5 | Ccv | Ile | Ccv | Met | Ccv | Leu | | | D |
| 6 | Ccv | Val | Ccv | Met | Ccv | Val | Pro | Val | D |
| 7 | Ccv | Phe | Ccv | Ile | Ccv | Val | Pro | Val | D |
| 8 | Ccv | Leu | Ccv | Ile | Ccv | Val | Pro | | D |
| 9 | Tcv | Ala | Ccv | Ile | Tbren | Phe | | | D |
| 10 | Thr | Ala | Ccv | Ile | Tbren | Phe | | | D |
| 11 | | Phe | Ccv | Tbren | Spren | Ile | Ala | Pro | D |
| 12 | Tbren | Leu | Ccv | Tbren | Val | Pip | Val | Pro | L |
| 13 | Tbren | Leu | Ccv | Tbren | Val | Pro | Val | Pro | L |
| 14 | Tbren | Leu | Ccv | Tbren | Ile | Pro | Val | Pro | L |
| 15 | Tbren | Val | Ccv | Tbren | Ile | Pro | Val | Pro | L |
| 16 | Spren | Phe | Ccv | Tbren | Val | Pro | Val | Pro | L |
| 17 | Tbren | Val | Ccv | Tbren | Phe | Pro | Val | Pro | L |
| 18 | Spren | Phe | Pro | Ccv | Ile | Pro | Ile | | D |

Heterocycle  Prenylation

Figure 22

- Last GRC:
  – Described nonribosomal pathway
  – Metabolic diversity between strains
  – Genome project planning

| Sample | Ascidian | Chemistry | 16S rDNA | prnA |
|---|---|---|---|---|
| Palau Reef | L. patella | Patellamides | Prochloron | + |
| Palau Seagrass | L. patella | None | Prochloron | + |
| PNG 03-001 | L. patella | Patellamides | Prochloron | - |
| PNG 03-002 | D. molle | None | Mixed | - |
| PNG 03-005 | L. patella | Patellamides | Prochloron | - |
| PNG 03-009 | D. molle | None | Mixed | - |
| PNG 03-011 | D. molle | Mollamides | Mixed | - |
| PNG 03-012 | D. molle | None | Mixed | - |
| PNG 03-017 | unidentified | Patellamides | Prochloron | + |
| PNG 03-018 | unidentified | None | Prochloron | + |
| PNG 03-019 | unidentified | None | Prochloron | + |
| PNG 03-020 | unidentified | None | Prochloron | - |

Schmidt et al., J. Nat. Prod. 2004, 67, 1341.

The *pat* cluster

- In the draft sequence...
  - Search for all 8 possible coding sequences
  - MNKKNILPQQGQPVIRLTAGQLSSQLAELSEEALGDAGLE
    ASVTACITFCAYDGVEPSITVCISVCAYDGE Biogenesis

- Heterocyclization / oxidation
  - PatD: 784 amino acids
    - 2 domains: N-terminal putative hydrolase, C-terminal possible ATPase
    - Cyclization to thiazoline / oxazoline
  - PatG: 1187 amino acids
    - 2 domains: N-terminal oxidase, C-terminal protease
    - Oxidation of thiazoline to thiazole + epimerization

Biogenesis

- Cyclization / cleavage
  - PatG: 1187 amino acids
    - 2 domains: N-terminal oxidase, C-terminal protease
  - PatA: 702 amino acids
    - Putative protease

```
>PatE  MNKKNILPQQGQPVIRTAGQLSSQLAELSEEALGDAGLEASVTACITFCAYDG
                                          VEPSITVCISVCAYDGE
```

- Recognition sequences
- Library

Figure 27

Structure

```
>PatE  MNKKNILPQQGQPVIRTAGQLSSQLAELSEEALGDA----------GLEASVTACITFC---AYDG--
>TriG  MGKKNIQPNSSQPVFRSLVARPA-LEELREENLTEGNQGHGPLANGPGPSGDGLHPRLCSCSYDGDDE
                                                   --VEPSITVCISVC---AYDGE
```

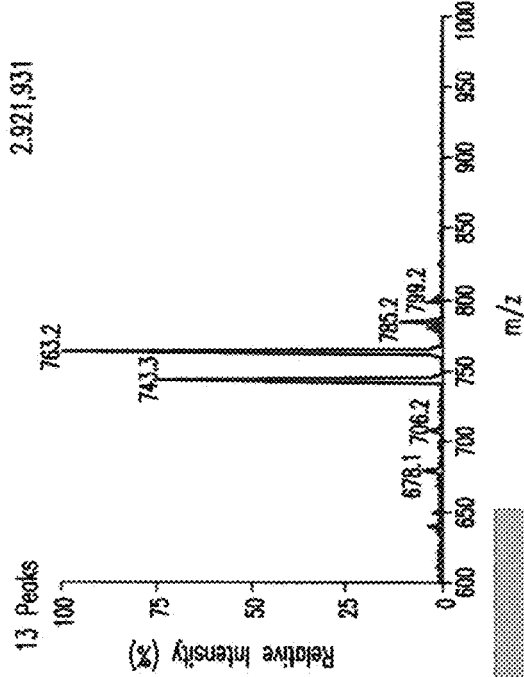
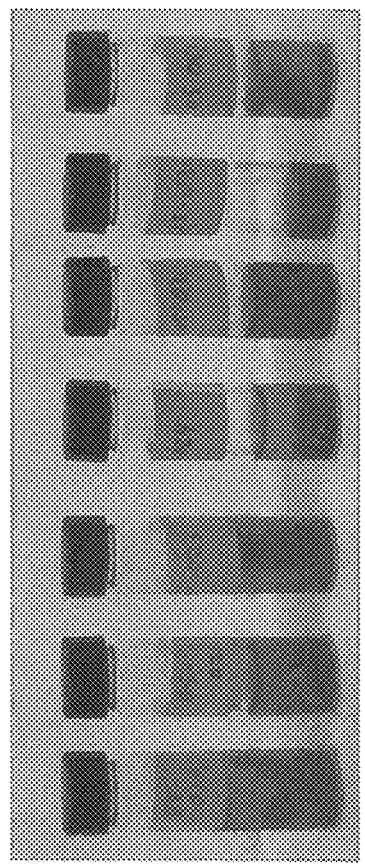
FIG. 29

Figure 30
PatE Evolution

- DNA: Identical except in coding region
- Only "Patellamide A" region is changed Patellamide A >PatE1   MNKKNILPQQGQPVIRTAGQLSSQLAELSEEALGDAGLEASVTACITFCAYDGVEPSITVCISVCAYDGE >PatE2   MNKKNILPQQGQPVIRTAGQLSSQLAELSEEALGDAGLEASVTACITFCAYDGVEPSCTLCCTLCAYDGE Ulithiacyclamide

PatE Evolution

| COMPOUND | CODING SEQUENCE |
|---|---|
| patellamide C | V T A C I T F C |
| patellamide A | I T V C I S V C |
| ulithiacyclamide | C T L C C T L C |
| patellamide B | L T A C I T F C |
| lissoclinamide 2/3 | A C F P T I C |
| lissoclinamide 4/5 | F C F P T V C |
| new compound 1 | F I F A T V C |
| new compound 2 | S C F P T I C |
| new compound 3 | F I F P T V C |
| trichamide | G D G L H P R L C S C |

*pat* Biochemistry

| vector | Expt1 | Expt2 | Expt3 | Expt4 | Expt5 | Expt6 | Expt7 |
|---|---|---|---|---|---|---|---|
| pACYC-patA | x | | | | | | x |
| pACYC-patAC | | x | | x | x | | |
| pCDF-patDG | x | x | x | x | x | x | |
| pCDF-patG | | | | | | | x |
| pET-patBF | x | x | x | | | x | x |
| pET-patF | | | | x | | | |
| pRSF-patE | x | | x | x | x | x | x |
| pRSF | | x | | | | | |
| Title | All | E control | -PatC | -PatBC | -PatBCF | -PatAC | -PatCD |
| proteins | ABCDEFG | ABCDFG | ABDEFG | ADEFG | ADEG | BDEFG | ABEFG |
| Patellamide? | Yes | No | Yes | Yes, less | No (!) | No | No |

Required proteins include PatF!

PatB helps

Figure 34
Eptidemnamide Synthesis

- Swap sequence in single mutagenesis

PatE2: MNKKN(X)$_{31}$GLEASVTACITFCAYDGVEPSCTLCCTLCAYDGE

PatEdm: MNKKN(X)$_{31}$GLEASVTACITFCAYDGVEPSQGGRGDWPAYDGE

Recognition sequence

- Single P-Q mutation
- Synthesis abolished

PatEdm: MNKKN(X)$

- PCR amplification of the whole cluster

Cloning the whole cluster in pCR2.1 TOPO
Overnight expression at 30°

SEQUENCE LISTING

<160> NUMBER OF SEQ ID NOS: 53

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence; note = synthetic construct
<220> FEATURE:
<221> NAME/KEY: VARIANT
<222> LOCATION: 6, 15

```
<223> OTHER INFORMATION: Xaa is any one or more amino acid

<400> SEQUENCE: 1

Gly Leu Glu Ala Ser Xaa Ala Tyr Asp Gly Val Glu Pro Ser Xaa Ala
1               5                   10                  15

Tyr Asp Gly Glu
            20

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 6
<223> OTHER INFORMATION: Xaa is any one or more amino acid

<400> SEQUENCE: 2

Gly Leu Glu Ala Ser Xaa Ala Tyr Asp Gly Val Glu Pro Ser
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 9
<223> OTHER INFORMATION: Xaa is any one or more amino acid

<400> SEQUENCE: 3

Ala Tyr Asp Gly Val Glu Pro Ser Xaa Ala Tyr Asp Gly Glu
1               5                   10

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Gly Leu Glu Ala Ser Val Thr Ala Cys Ile Thr Phe Cys Ala Tyr Asp
1               5                   10                  15

Gly Val Glu Pro Ser Cys Thr Leu Cys Cys Thr Leu Cys Ala Tyr Asp
            20                  25                  30

Gly Glu

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Gly Leu Glu Ala Ser Val Thr Ala Cys Ile Thr Phe Cys Ala Tyr Asp
1               5                   10                  15
```

-continued

Gly Val Glu Pro Ser Gln Gly Gly Arg Gly Asp Trp Pro Ala Tyr Asp
            20                  25                  30

Gly Glu

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Gly Leu Glu Ala Ser Val Thr Ala Cys Ile Thr Phe Cys Ala Tyr Asp
 1               5                  10                  15

Gly Val Glu Pro Ser Ile Thr Val Cys Ile Ser Val Cys Ala Tyr Asp
            20                  25                  30

Gly Glu

<210> SEQ ID NO 7
<211> LENGTH: 67
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Met Gly Lys Lys Asn Ile Gln Pro Asn Ser Ser Gln Pro Val Phe Arg
 1               5                  10                  15

Ser Leu Val Ala Arg Pro Ala Leu Glu Glu Leu Arg Glu Glu Asn Leu
            20                  25                  30

Thr Glu Gly Asn Gln Gly His Gly Pro Leu Ala Asn Gly Pro Gly Pro
        35                  40                  45

Ser Gly Asp Gly Leu His Pro Arg Leu Cys Ser Cys Ser Tyr Asp Gly
    50                  55                  60

Asp Asp Glu
65

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 8

Gly Pro Gly Pro Ser Gly Asp Gly Leu His Pro Arg Leu Cys Ser Cys
 1               5                  10                  15

Ser Tyr Asp Gly Asp Asp Glu
            20

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Gly Pro Gly Pro Ser Asn Ser Tyr Asp Gly Asp Asp Glu

```
                1               5                  10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 10

Gly Leu Glu Ala Ser
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 11

Ala Tyr Asp Gly Val Glu Pro Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 12

Ala Tyr Asp Gly Glu
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 13

Gly Pro Gly Pro Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 14

Ser Tyr Asp Gly Asp Asp Glu
1               5

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence; note =
``` synthetic construct

<400> SEQUENCE: 15
gcatcacttt ttgcgcttat gatggtgtgg agccatctca gggcggacgc ggtgactggc    60
ctgcttacga tggtgaataa    80

<210> SEQ ID NO 16
<211> LENGTH: 80
<212> TYPE: DNA
<213> ORGANISM: Artificial Sequence
<220> FEATURE:
<223> OTHER INFORMATION: Description of Artificial Sequence; note = synthetic construct

<400> SEQUENCE: 16
ttattcacca tcgtaagcag gccagtcacc gcgtccgccc tgagatggct ccacaccatc    60
ataagcgcaa aaagtgatgc    80

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence; note = synthetic construct

<400> SEQUENCE: 17

Gly Pro Gly Pro Ser
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence; note = synthetic construct

<400> SEQUENCE: 18

Ser Tyr Asp Gly Asp
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence; note = synthetic construct

<400> SEQUENCE: 19

Gly Asp Gly Leu His Pro Arg Leu Cys Ser Cys
1               5                   10

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence; note = synthetic construct

<400> SEQUENCE: 20
cgtgaaaatt gctctttgaa taaagg    26

```
<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 21
atcatgaata gagatatttt gcgaac                                          26

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 22
gaatcatgag acttccgcta ctgtc                                           25

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 23
aaacatatga tggtcactaa caaccc                                          26

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 24
ttcatgaacc caaccgcgct ccaaattaag                                      30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 25
ccaaccaaca tatgaacaag aagaacattc taccccc                              36

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 26
aacatatgga cttaaattga caggcttc                                        28

<210> SEQ ID NO 27
```

```
<211> LENGTH: 28
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 27
ccatatgatc acgatagact acccttc                                          28

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 28
tcggccgttc cttagtaaga agaagaccaa g                                     31

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 29
aaatgcggcc gcttaatcag aataagcgtc ccatac                                36

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 30
aaaggtaccg aaagaagtag ccttagagtt aag                                   33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 31
gccgcggccg caaacttgaa aatgcttaaa acg                                   33

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 32
ttcttattgg taccctatt caccatc                                           27

<210> SEQ ID NO 33
<211> LENGTH: 29
```

```
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 33
atgactaggt acctgagtca atgcaaatg                                          29

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 34
cggtacccca ataactactt tgagacggtg                                         30

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2, 3, 4
<223> OTHER INFORMATION: Xaa = Any Amino Acid

<400> SEQUENCE: 35

Gly Xaa Xaa Xaa Ser
 1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 1
<223> OTHER INFORMATION: Xaa = Any Amino Acid

<400> SEQUENCE: 36

Xaa Tyr Asp Gly
 1

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 37
acggcaaagg gagtttaaac gg                                                 22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence; note =
```

```
                    synthetic construct

<400> SEQUENCE: 38
cgcagctacg agcaaaacat tg                                              22

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 39
ccacagttga ggccagcac                                                  19

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 2
<223> OTHER INFORMATION: Xaa can be either Leu or Val
<220> FEATURE:
<221> NAME/KEY: VARIANT
<222> LOCATION: 4
<223> OTHER INFORMATION: Xaa can be either Ala or Pro

<400> SEQUENCE: 40

Gly Xaa Glu Xaa Ser
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 5
<223> OTHER INFORMATION: Xaa can be either Glu or Val

<400> SEQUENCE: 41

Ala Tyr Asp Gly Xaa
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 42

Gly Ala Glu Pro Arg
 1               5

<210> SEQ ID NO 43
<211> LENGTH: 70
<212> TYPE: PRT
<213> ORGANISM: Artificial Sequence
<220> FEATURE:
```

```
<223> OTHER INFORMATION: Description of Artificial Sequence; note =
      synthetic construct
<220> FEATURE:
<221> NAME/KEY: VARIANT
<222> LOCATION: 6, 7, 8, 9, 10, 11, 12, 13, 14, 15, 16, 17, 18, 19, 20,
      21, 22, 23, 24, 25, 26, 27, 28, 29, 30, 31, 32, 33, 34, 35, 36
<223> OTHER INFORMATION: Xaa = Any Amino Acid

<400> SEQUENCE: 43

Met Asn Lys Lys Asn Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Gly Leu Glu Ala Ser Val Thr Ala Cys Ile Thr Phe
        35                  40                  45

Cys Ala Tyr Asp Gly Val Glu Pro Ser Cys Thr Leu Cys Cys Thr Leu
    50                  55                  60

Cys Ala Tyr Asp Gly Glu
65                  70

<210> SEQ ID NO 44
<211> LENGTH: 70
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 6, 7, 8, 9, 10, 11, 12, 13, 14, 15, 16, 17, 18, 19, 20,
      21, 22, 23, 24, 25, 26, 27, 28, 29, 30, 31, 32, 33, 34, 35, 36
<223> OTHER INFORMATION: Xaa = Any Amino Acid

<400> SEQUENCE: 44

Met Asn Lys Lys Asn Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Gly Leu Glu Ala Ser Val Thr Ala Cys Ile Thr Phe
        35                  40                  45

Cys Ala Tyr Asp Gly Val Glu Pro Ser Gln Gly Gly Arg Gly Asp Trp
    50                  55                  60

Pro Ala Tyr Asp Gly Glu
65                  70

<210> SEQ ID NO 45
<211> LENGTH: 70
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 45

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
            20                  25                  30

Leu Gly Asp Ala Gly Leu Glu Ala Ser Val Thr Ala Cys Ile Thr Phe
        35                  40                  45

Cys Ala Tyr Asp Gly Val Glu Pro Ser Ile Thr Val Cys Ile Ser Val
    50                  55                  60
```

Cys Ala Tyr Asp Gly Glu
65                  70

<210> SEQ ID NO 46
<211> LENGTH: 70
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 46

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
            20                  25                  30

Leu Gly Asp Ala Gly Leu Glu Ala Ser Val Thr Ala Cys Ile Thr Phe
        35                  40                  45

Cys Ala Tyr Asp Gly Val Glu Pro Ser Gln Gly Arg Gly Asp Trp
    50                  55                  60

Pro Ala Tyr Asp Gly Glu
65                  70

<210> SEQ ID NO 47
<211> LENGTH: 70
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 47

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
            20                  25                  30

Leu Gly Asp Ala Gly Leu Glu Ala Ser Val Thr Ala Cys Ile Thr Phe
        35                  40                  45

Cys Ala Tyr Asp Gly Val Glu Gln Ser Gln Gly Gly Arg Gly Asp Trp
    50                  55                  60

Pro Ala Tyr Asp Gly Glu
65                  70

<210> SEQ ID NO 48
<211> LENGTH: 70
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 48

Met Asn Lys Lys Asn Ile Leu Pro Gln Gln Gly Gln Pro Val Ile Arg
1               5                   10                  15

Thr Ala Gly Gln Leu Ser Ser Gln Leu Ala Glu Leu Ser Glu Glu Ala
            20                  25                  30

Leu Gly Asp Ala Gly Leu Glu Ala Ser Val Thr Ala Cys Ile Thr Phe
        35                  40                  45

Cys Ala Tyr Asp Gly Val Glu Gln Ser Gln Gly Gly Arg Gly Asp Trp
    50                  55                  60

Pro Ala Tyr Asp Gly Glu

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence; note = synthetic construct

<400> SEQUENCE: 49

Gly Val Asp Ala Ser Thr Leu Pro Val Pro Thr Leu Cys Ser Tyr Asp
 1               5                  10                  15

Gly Val Asp Ala Ser Thr Val Pro Thr Leu Cys Ser Tyr Asp Asp
            20                  25                  30

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence; note = synthetic construct
<220> FEATURE:
<221> NAME/KEY: VARIANT
<222> LOCATION: 6, 15
<223> OTHER INFORMATION: Xaa is any one or more amino acid

<400> SEQUENCE: 50

Gly Val Asp Ala Ser Xaa Ser Tyr Asp Gly Val Asp Ala Ser Xaa Ser
 1               5                  10                  15

Tyr Asp Asp

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence; note = synthetic construct

<400> SEQUENCE: 51

Gly Val Asp Ala Ser Thr Phe Pro Val Pro Thr Val Cys Ser Tyr Asp
 1               5                  10                  15

Gly Val Asp Ala Ser Thr Ser Pro Leu Ala Pro Leu Cys Ser Tyr Asp
            20                  25                  30

Asp

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence; note = synthetic construct
<220> FEATURE:
<221> NAME/KEY: VARIANT
<222> LOCATION: 6
<223> OTHER INFORMATION: Xaa is any one or more amino acid

<400> SEQUENCE: 52

Gly Val Asp Ala Ser Xaa Ser Tyr Asp Gly Val Asp Ala Ser
 1               5                  10

<210> SEQ ID NO 53
<211> LENGTH: 13

```
<212> TYPE: PRT
<213> ORGANISM: Artificial Sequence
<220> FEATURE:
<223> OTHER INFORMATION: Description of Artificial Sequence; note =
      synthetic construct
<220> FEATURE:
<221> NAME/KEY: VARIANT
<222> LOCATION: 9
<223> OTHER INFORMATION: Xaa is any one or more amino acid

<400> SEQUENCE: 53

Ser Tyr Asp Gly Val Asp Ala Ser Xaa Ser Tyr Asp Asp
 1               5                  10
```

METHODS AND COMPOSITIONS RELATED TO CYCLIC PEPTIDE SYNTHESIS

I. CROSS REFERENCE TO RELATED APPLICATIONS

The present application is a National Phase Application of International Application No. PCT/US2007/063089, filed Mar. 1, 2007, which claims priority to U.S. Patent Application No. 60/777,954, filed Mar. 1, 2006, which applications are incorporated herein fully by this reference.

II. ACKNOWLEDGEMENTS

This invention was made with government support under grant number R01 GM071425 awarded by National Institutes of Health and grant number 0412226 awarded by National Science Foundation. The government has certain rights in the invention.

III. BACKGROUND

*Prochloron* spp. are obligate cyanobacterial symbionts of many didemnid family ascidians. It has been proposed that the cyclic peptides of the patellamide class found in didemnid extracts are synthesized by *Prochloron* sp., but studies in which host and symbiont cells are separated and chemically analyzed to identify the biosynthetic source have yielded inconclusive results. As part of the *Prochloron didemni* sequencing project, patellamide biosynthetic genes were identified, and their function confirmed by heterologous expression of the whole pathway in *Escherichia coli*. The primary sequence of patellamides A and C is encoded on a single open reading frame that resembles a precursor peptide. This pre-patellamide is heterocyclized to form thiazole and oxazoline rings, and the peptide is cleaved to yield the two cyclic patellamides, A and C.

Marine invertebrates, particularly sponges and ascidians, are well known for their production of bioactive natural products (Newman et al. (2005) Mol. Cancer. Ther. 4, 333-342. A major hurdle in the development of many of these agents into drugs has been their supply, since collection or aquaculture of marine invertebrates pose many difficulties and may not be environmentally acceptable. Because marine invertebrate compounds often resemble molecules isolated from bacteria, many compounds are synthesized by symbiotic bacteria and not by the animals themselves (Faulkner et al. (1993) Gazz. Chim. Ital. 123, 301-307; Kobayashi et al. (1993) Chem. Rev. 93, 1753-1770; Sings et al. (1996) J. Ind. Microbiol. Biot. 17, 385-396; Haygood et al. (1999) J. Mol. Microbiol. Biot. 1, 33-34). Recently, these early speculations have been borne out in the cloning and sequencing of genes from two symbiotic natural product pathways (Piel et al. (2004) Proc. Natl. Acad. Sci. USA 101, 16222-16227; Hildebrand et al. (2004) Chem. Biol. 11, 1543-1552), opening a new era in marine natural products discovery and development.

Ascidians in the family Didemnidae contain numerous structural classes of cyclic peptides and harbor symbiotic cyanobacteria, *Prochloron* spp. (FIG. 15) (Withers et al. (1978) Phycologia 17, 167-171; Lewin, R. A. & Cheng, L. (1989) (Chapman and Hall, New York)). Despite nearly 30 years of attempts, *Prochloron* sp. have eluded cultivation and are thus considered to be obligate symbionts. *Prochloron* sp., unlike the vast majority of cyanobacteria but like plants, use both chlorophylls a and b for photosynthesis, lack phycobilins, and have plant-like thylakoids (Withers et al. (1978) Proc. Natl. Acad. Sci. USA 75, 2301-2305). The cells are relatively large for bacteria (10-20 µm in diameter). *Prochloron* has also been implicated in the biosynthesis of cyclic peptides isolated from whole didemnid ascidians. In early cell-separation studies, it was reported that the peptides were localized in *Prochloron* cells (Degnan et al. (1989) J. Med. Chem. 32, 1349-1354; Biard et al. (1990) J. Mar. Biol. Assoc. UK 70, 741-746), but a later investigation found the molecules distributed throughout the ascidian tunic, as well as in the cyanobacteria (Salomon, C. E. & Faulkner, D. J. (2002) J. Nat. Prod. 65, 689-692). Because of the unique biological and chemical features of the *Prochloron*-ascidian symbiosis, a project was initiated to sequence the genome of *Prochloron didemni*, isolated from the ascidian *Lissoclinum patella*.

The patellamides and trunkamide (another didemnid product) are peptides that exemplify both the unique structural features and potent bioactivities of didemnid ascidian natural products (FIG. 15). Both groups have clinical usefulness, since patellamides are typically moderately cytotoxic, and patellamides B, C, and D reportedly reverse multidrug resistance (Williams et al. (1993) Cancer Lett. 71, 97-102; Fu et al (1998) J. Nat. Prod. 61, 1547-1551), while trunkamide was initially isolated because of specific and unusual activity against the multidrug resistant UO-31 renal cell line (Carroll, A. et al (1996) Aust. J. Chem. 49, 659-667). Patellamides are characteristically composed of pseudo-symmetrical, cyclic dimers, with each substructure having the sequence thiazole-nonpolar amino acid-oxazoline-nonpolar amino acid. Trunkamide and related molecules often contain proline, thiazolines, and prenylated serine and threonine derivatives. These features can result from either a ribosomal or a nonribosomal peptide biosynthetic pathway, since precedents exist for heterocyclization and cyclization in both cases (Gehring et al. (1998) Biochemistry 37, 11637-11650; et al. (2000) Nature 407, 215-218; Li et al. (1996) Science 274, 1188-1193; Solbiati et al. (1999) J. Bacteriol. 181, 2659-2662). The nonribosomal hypothesis of patellamide biosynthesis was investigated using a homology-based approach (Schmidt et al (2004) *J. Nat. Prod.* 67, 1341-1345). Only a single nonribosomal peptide synthetase (NRPS) gene was identified in fosmid clones, but the gene was found in only a few strains, and its presence did not correlate with patellamide production.

Bacterial secondary metabolites are bioactive small molecules that often find use as pharmaceuticals. (Newman et al. J. Nat. Prod. 66, 1022-1037 (2003)). Numerous studies of secondary metabolite biosynthetic genes have led to an increasing ability to synthesize new small molecules through rational pathway engineering (Floss J. Biotechnol. epub (2006); Walsh, C. T. ChemBioChem, 124-134 (2002)). Much of this capability comes from gene sequence comparison, in which the observation of evolution of these pathways has enabled engineering. Despite the advances, a weakness of this approach is that most described pathways are relatively distantly related, making an analysis of single evolutionary events difficult to discern. This difficulty is compounded by the large number of dedicated enzymatic steps (up to approximately 60 or so) commonly required to synthesize individual secondary metabolites.

Small, cyclic peptides are valuable pharmaceuticals, biotechnological products, and tools for scientific research (Davies, J. S. Amino Acids, Peptides and Proteins 2003, 34, 149-217). Cyclic peptides in general have advantages over their linear relatives in that they sample a more constricted conformational and configurational space. (Payne et al. Curr. Org. Chem. 2002, 6, 1221-1246). Stemming from this basic property, cyclic peptides often have stronger binding constants and favorable pharmacological properties such as resistance to proteases (Fairlie, D. P.; Tyndall, J. D. A.; Reid, R. C.;

Wong, A. K.; Abbenante, G.; Scanlon, M. J.; March, D. R.; Bergman, D. A.; Chai, C. L. L.; Burkett, B. A. J. Med. Chem. 2000, 43, 1271-1281). Because of this, numerous investigators have developed means to produce arrays of small, cyclic peptides. Synthetic and enzymatic systems, as well as combinations of the two, have been used successfully on small and medium scale (Davies et al. J. Peptide Sci. 2003, 9, 471-501; Hahn et al. Proc. Nat. Acad. Sci. USA 2004, 101, 15585-15590). At the large scale, peptides in phage-display libraries have been cyclized via disulfide bonds or via semisynthesis from the same libraries (Kehoe, J. W.; Kay, B. K. Chem. Rev. 2005, 105, 4056-4072; Ho, K. L.; Yusoff, K.; Seow, H. F.; Tan, W. S. J. Med. Virol. 2003, 69, 27-32).

There is a great need for new methods for making cyclic peptides, particularly for the manufacture of synthetic cyclic peptides for clinical investigations and therapeutic use, and for the production of cyclic peptide libraries that can be screened to identify cyclic peptides with a desired activity. What is needed in the art are methods for the in vivo construction of cyclic peptide libraries that are enzymatically cyclized at the C—N terminus.

IV. SUMMARY

Disclosed are methods and compositions related to cyclization of polymers such as peptides.

V. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows PatE2 (SEQ ID NO: 43) encodes patellamide C (yellow) and ulithiacyclamide (green). Mutation of the sequence to PatEdm (SEQ ID NO: 44) leads to production of eptidemnamide (blue). Bold: proposed recognition sequences for heterocyclization and C—N terminal cyclization. Eptifibatide (bottom left) is shown for comparison.

FIG. 5 shows alignment of the precursor peptides PatE and TriG. The sequence encoding patellamide C, patellamide A and trichamide (top to bottom) is underlined, proposed cyclization signal is in bold.

FIG. 6A shows structure of trichamide. Stereochemistry is inferred, not determined experimentally, as described in the text. 6B. Assignment of CID-MS fragments from table 5 to the trichamide structure. 6C. Assignment of IRMPD-MS fragments.

Figure 7:
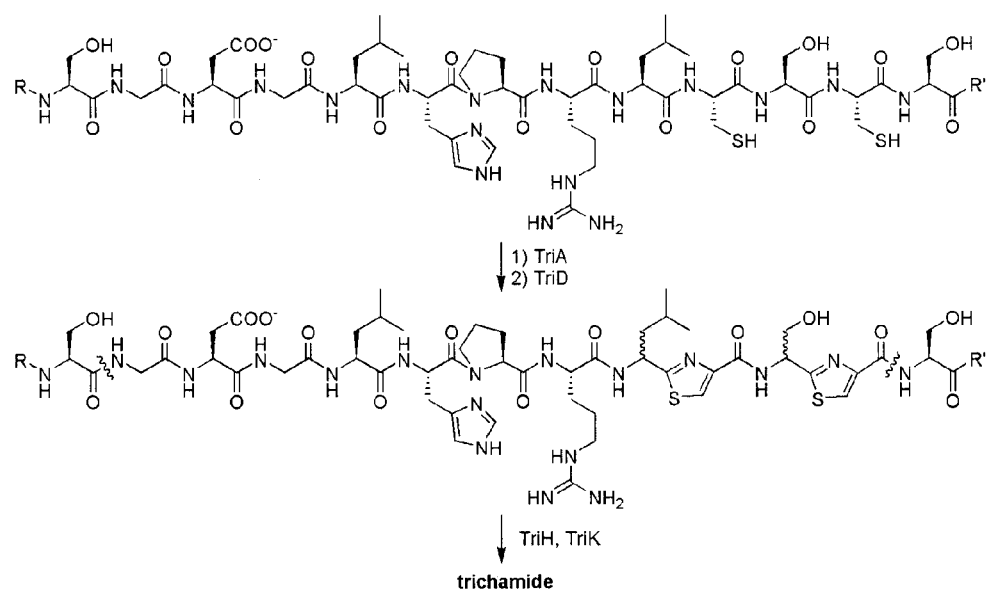

FIG. 7 shows a biosynthetic pathway to trichamide.

Figure 8:
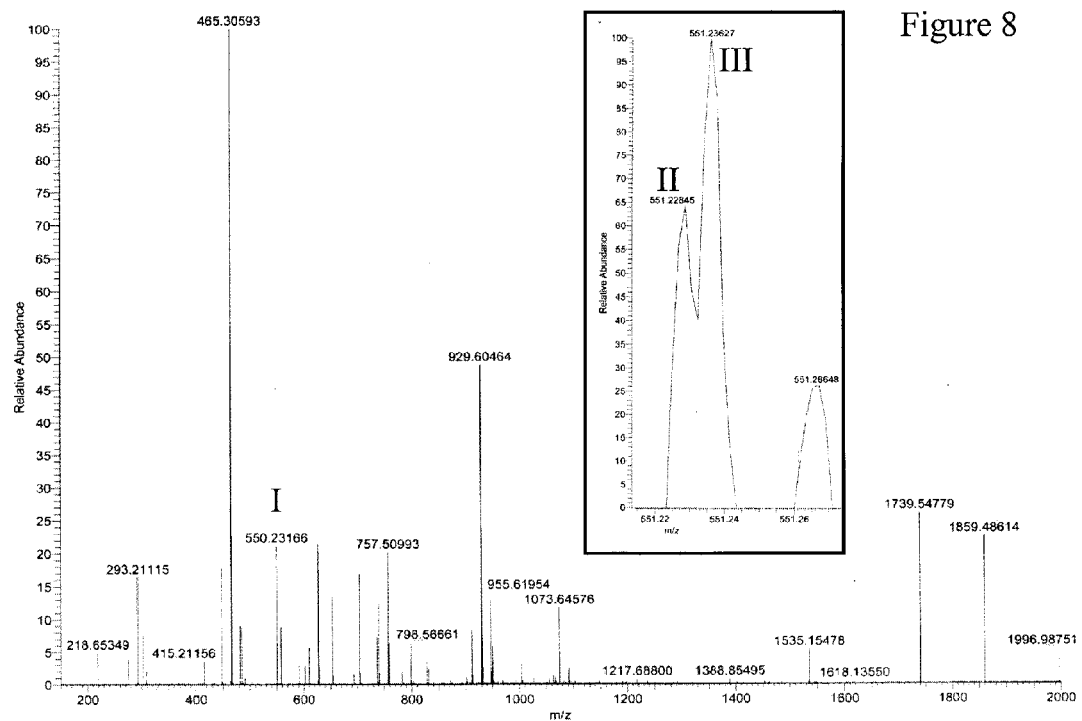

FIG. 8 shows FT-MS of a crude *Trichodesmium* extract. Peaks are present for the trichamide parent ion (I), the 34S isotope (II) and the 13C2 isotope (III).

Figure 9:
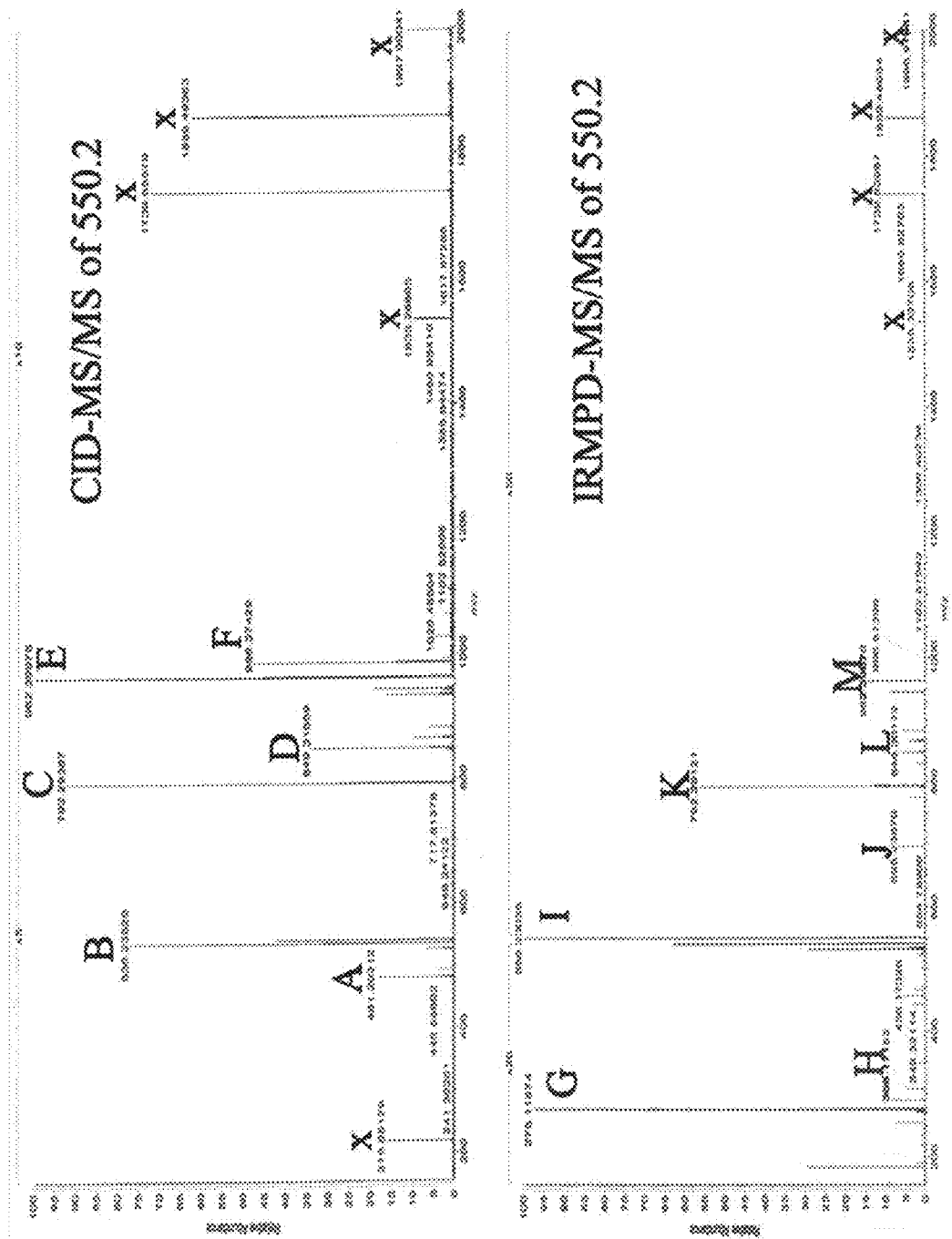

FIG. 9 show MS fragmentation patters of ion 550.2 with two different dissociation techniques. CID=collision-induced dissociation, IRMPD=infrared multiphoton dissociation. Peaks labeled "x" are artifacts of the instrument, and all other ions can be accounted for as in Table 5 and FIG. 6.

Figure 10:
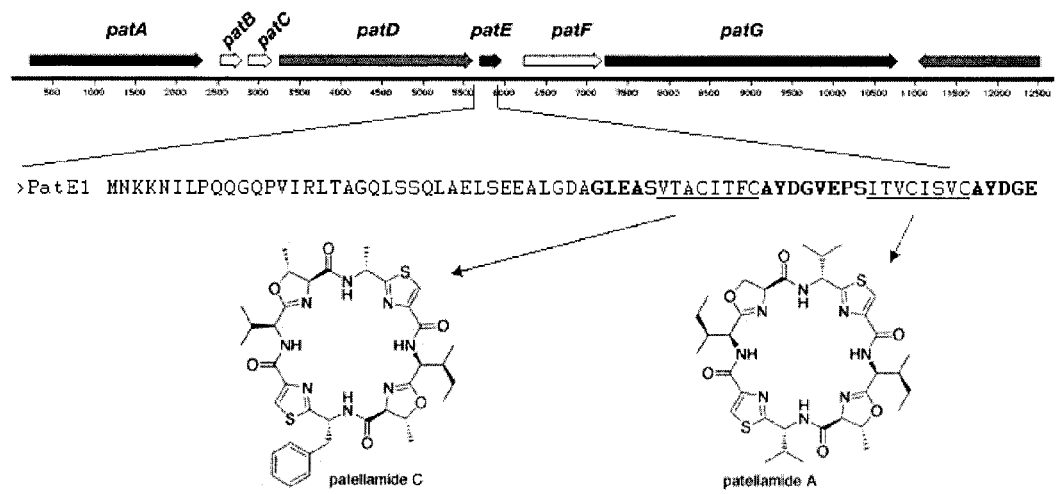

FIG. 10 shows the pat pathway. The PatE protein, now renamed PatE1, directly encodes the production of highly modified peptides, patellamides A and C. Putative recognition sequences flank the coding regions and are shown in bold.

Figure 11:
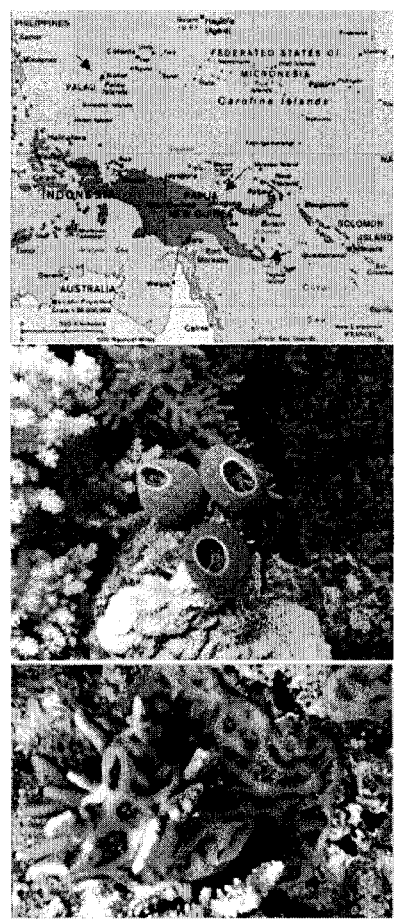

FIG. 11 shows diverse ascidians were collected from Palau and Papua New Guinea. Top: map of collection sites (red arrows). Middle: *Didemnum molle*. Bottom: *Lissoclinum patella*.

Figure 12:
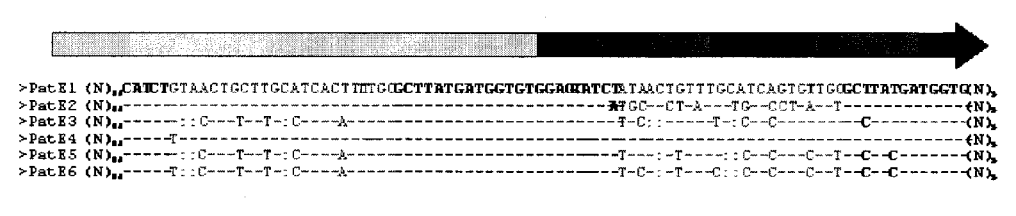

FIG. 12 show patE diversity. Although pat pathway variants are >99% identical at the DNA level, patE is hypervariable in the region encoding patellamides. Top: Schematic view ofpatE. Bottom: Sequence differences between patE1-E6. Dashes indicate residues that are identical to those in PatE1, and all residues N are identical between variants. Red: peptide-coding region. Black: recognition sequences.

Figure 13:
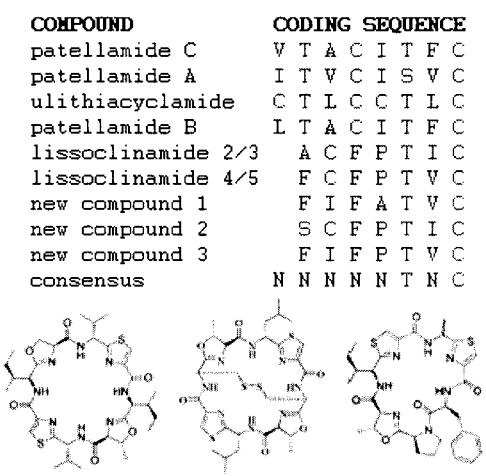

FIG. 13 shows sequences and structures predicted from patE sequence variants. All of the known compounds (blue) have been identified in the requisite ascidian samples.

Figure 14:
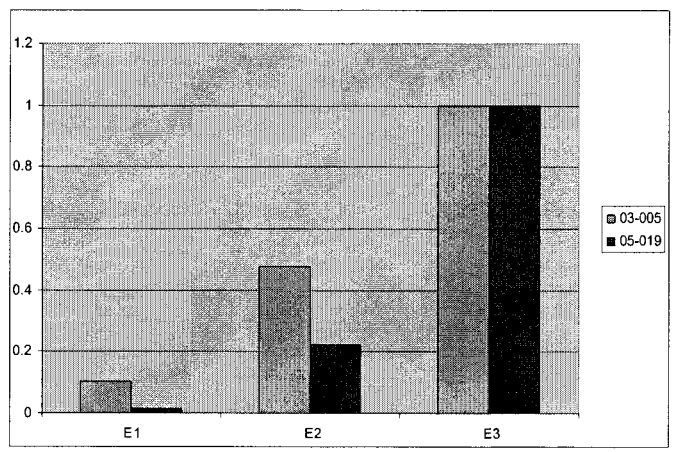

FIG. 14 shows quantitative PCR of *Prochloron* samples. Relative amounts of patE1-E3 genes present in samples 05-019 and 03-005, normalized to the patE3 concentration.

FIG. 15 shows top: Single cell of *P. didemni* (right) isolated from the ascidian *L. patella*. The green pockets near the surface of *L. patella* are monocultures of *P. didemni*. Bottom: Patellamides A and C.

FIG. 16 shows a PatE sequence. In italics, the conserved leader sequence; in bold, the proposed start and stop cyclization sequences; underlined, product-coding sequences. Sequences corresponding to patellamide C (top) and A (bottom) are aligned for clarity.

Figures 17A, 17B:
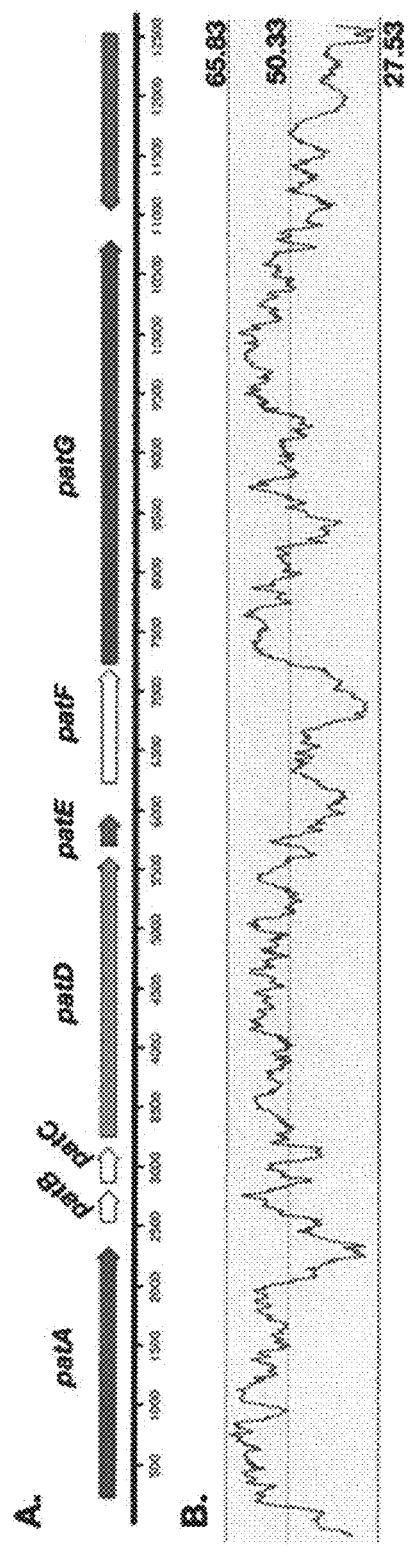

FIG. 17 shows the pat gene cluster (A) and GC skew (B). Colored genes represent those that can have a function assigned. White genes are those that have no significant homolog. Blue genes contains protease activity. The G+C % skew below is altered where a coding region is present, as is common in many species and suggests that the gene predictions are correct. Additionally, the increase of the G+C % in this area shows that this region could have been transferred into this species via horizontal gene transfer.

Figure 18:
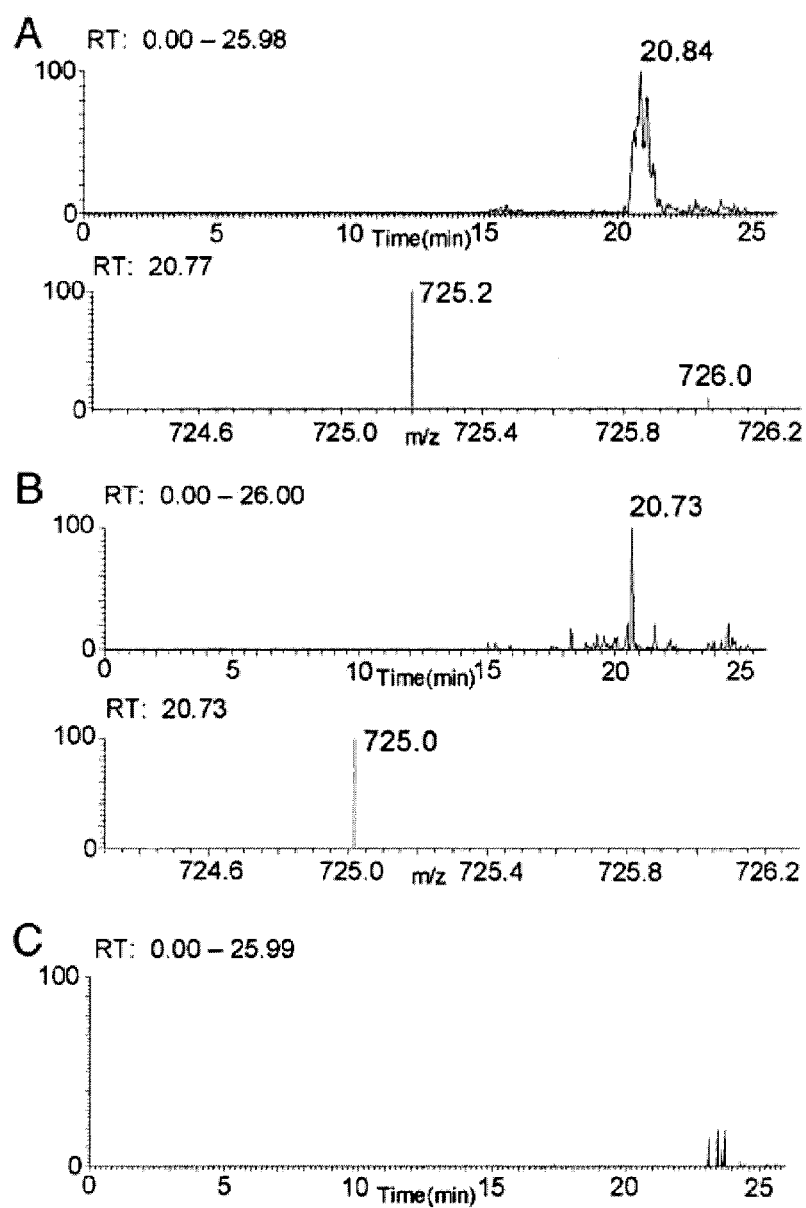

FIG. 18 shows proof of function of the pat cluster. (A) Standard from 25 mL culture broth containing 20 µg patellamides, under SRM conditions observing m/z=725 (patellamide A daughter ion). (B) 2 L sample pCR2.1-pat #9, under SRM conditions for m/z=725. (C) Blind control: SRM using a sample identical to (B), except that empty pCR2.1 vector was used.

Figure 19:
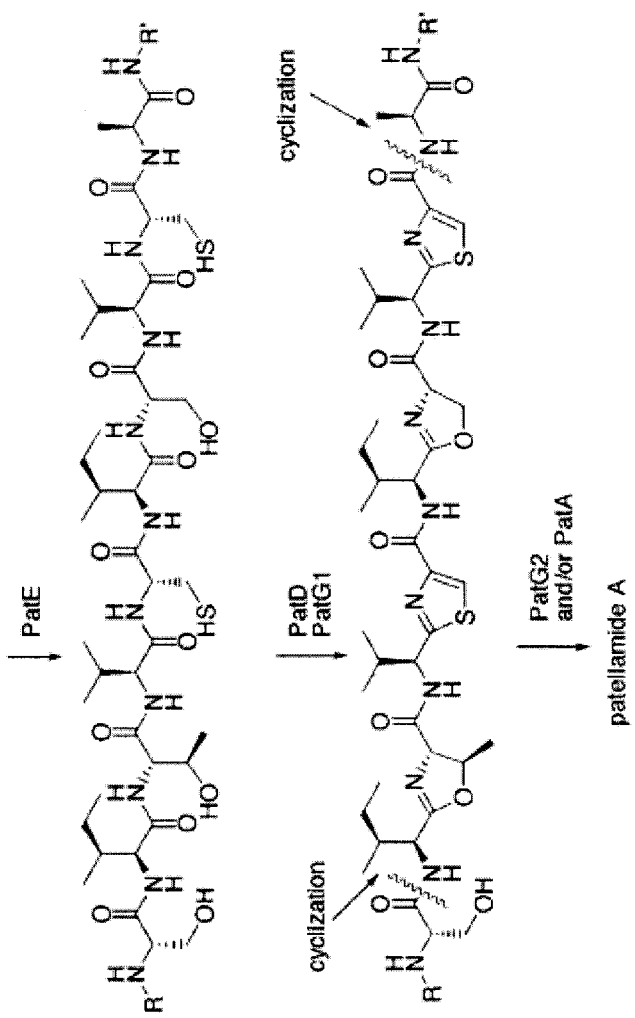

FIG. 19 shows a proposed pathway to patellamides, showing route to patellamide C.

Figure 20:
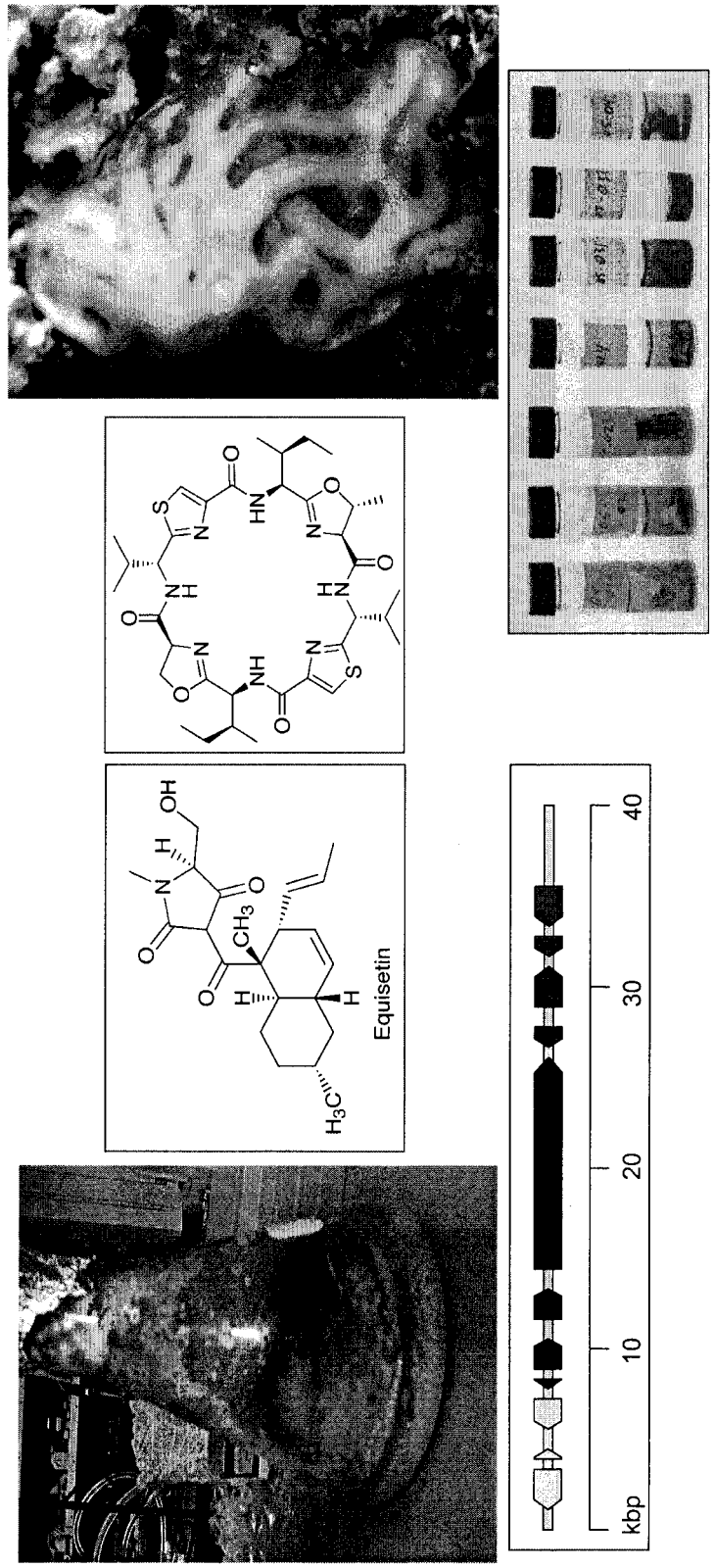

FIG. 20 shows marine symbionts and filamentous fungi.

FIG. 21 shows a family of compounds and various amino acid positions.

FIG. 22 shows the origin of various samples, the organism from which it was derived, its chemistry, source of the 16S rDNA, and whether or not it was positive for pmA.

Figure 23:
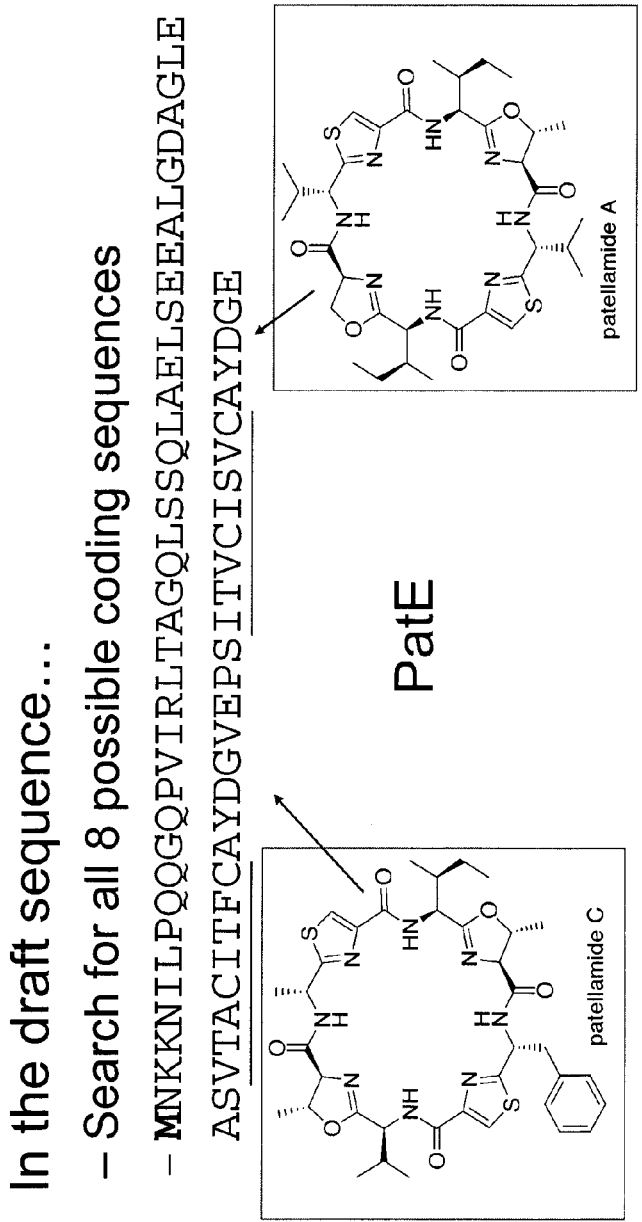

FIG. 23 shows the pat cluster, and the coding region of PatE.

Figure 24:
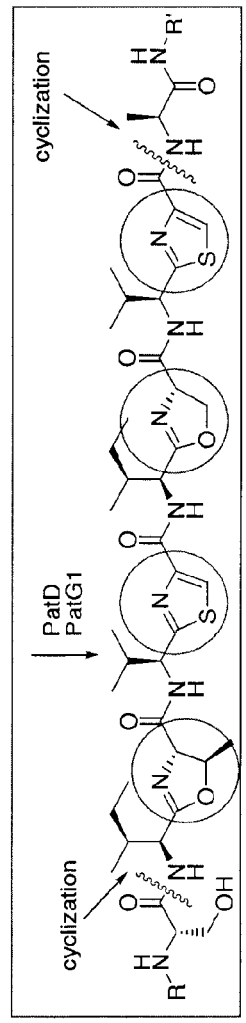

FIG. 24 shows biogenesis, and heterocyclization/oxidation for PatD and PatG.

Figure 25:
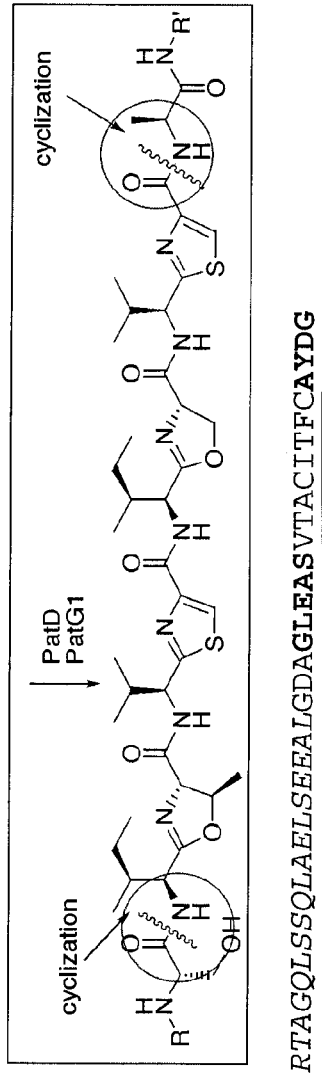
Figure 26A:
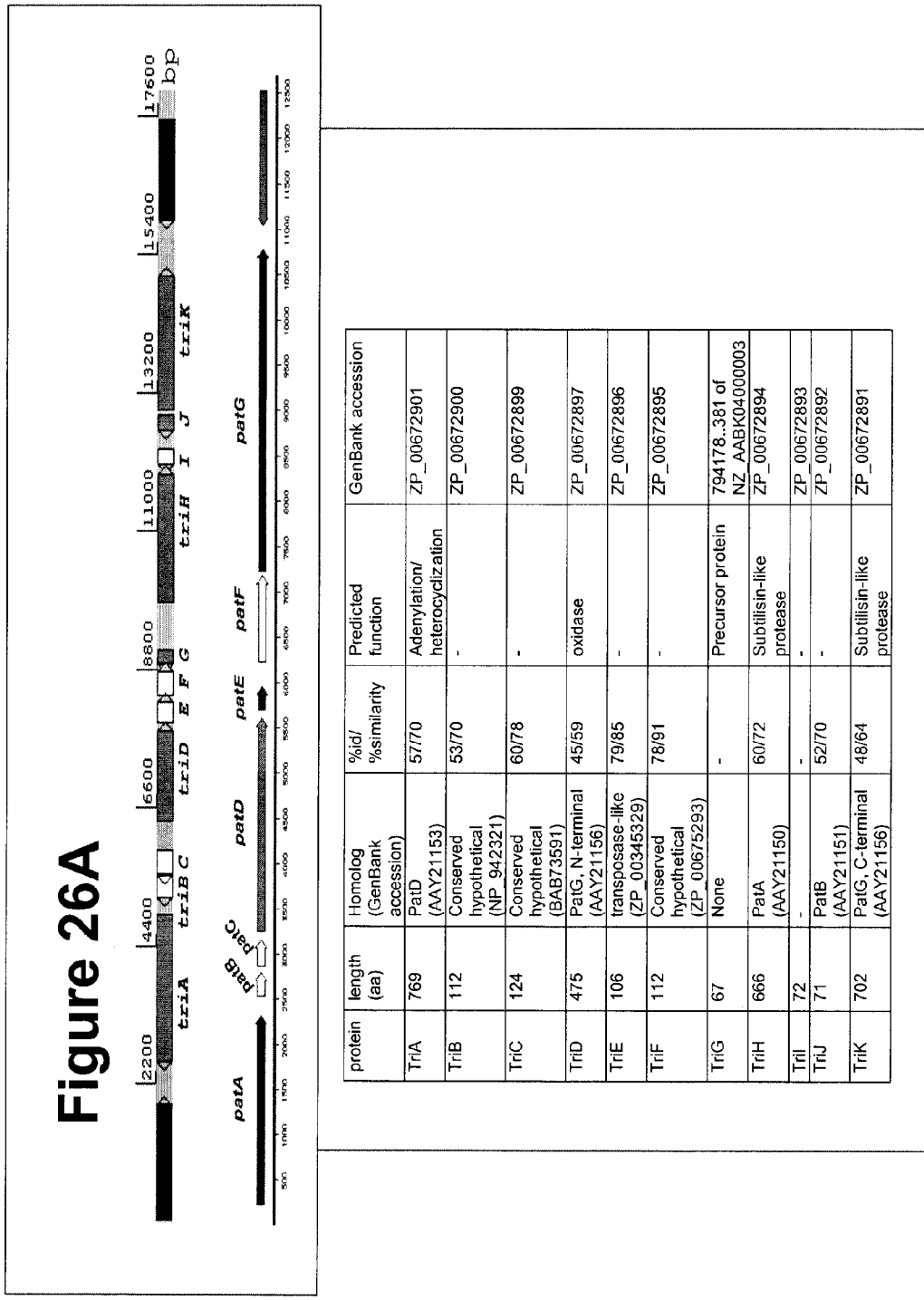
Figure 26A:
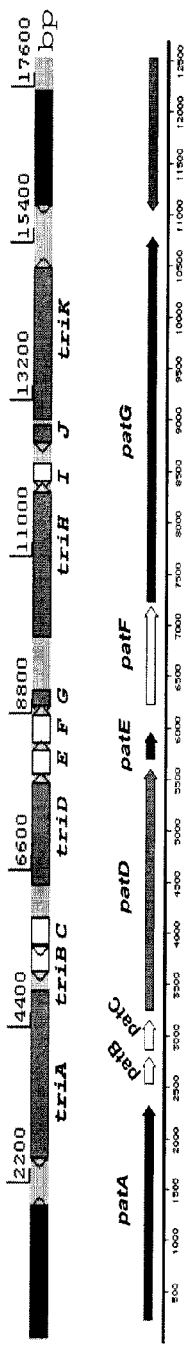
Figure 26B:
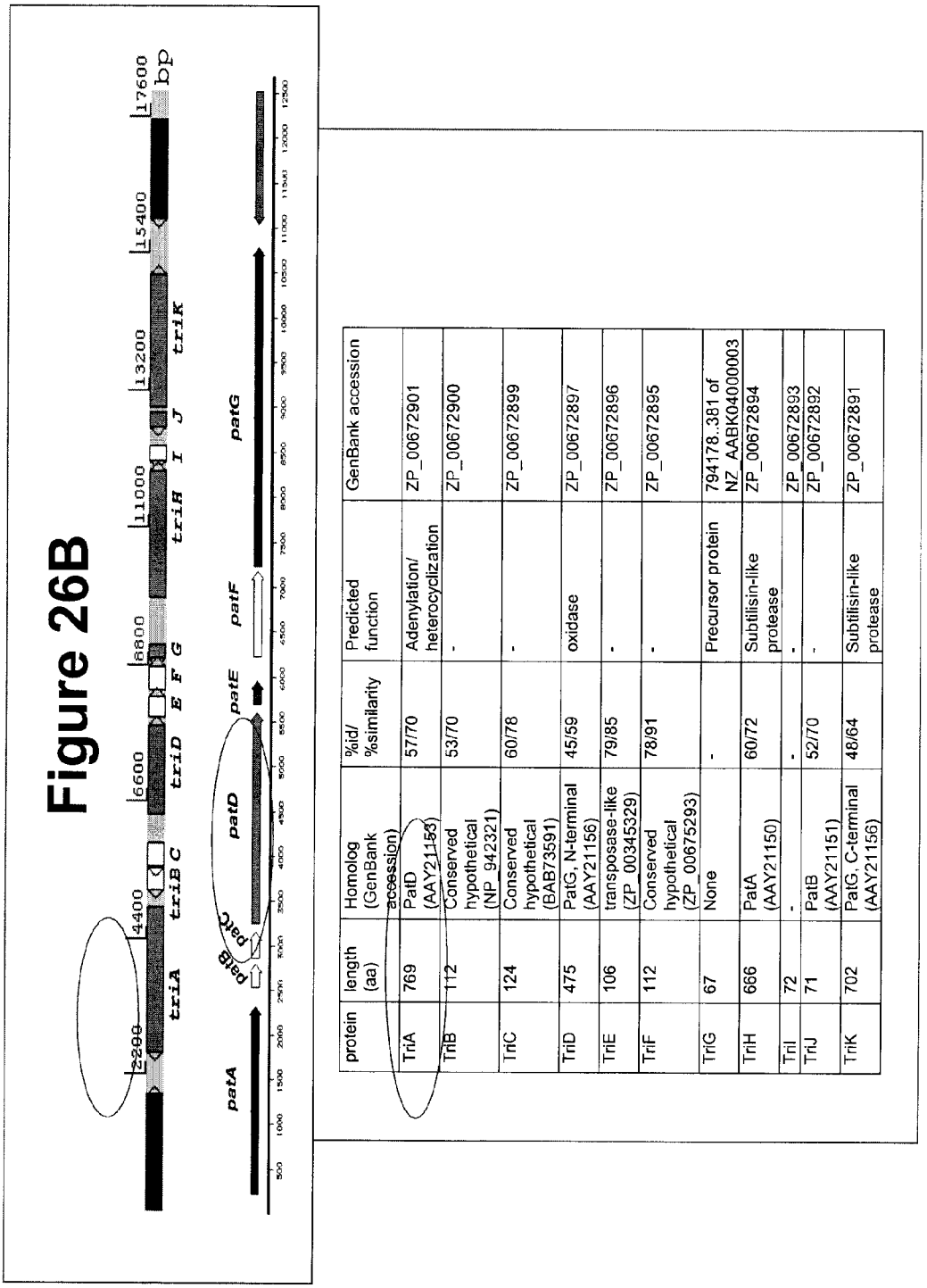
Figure 26C:
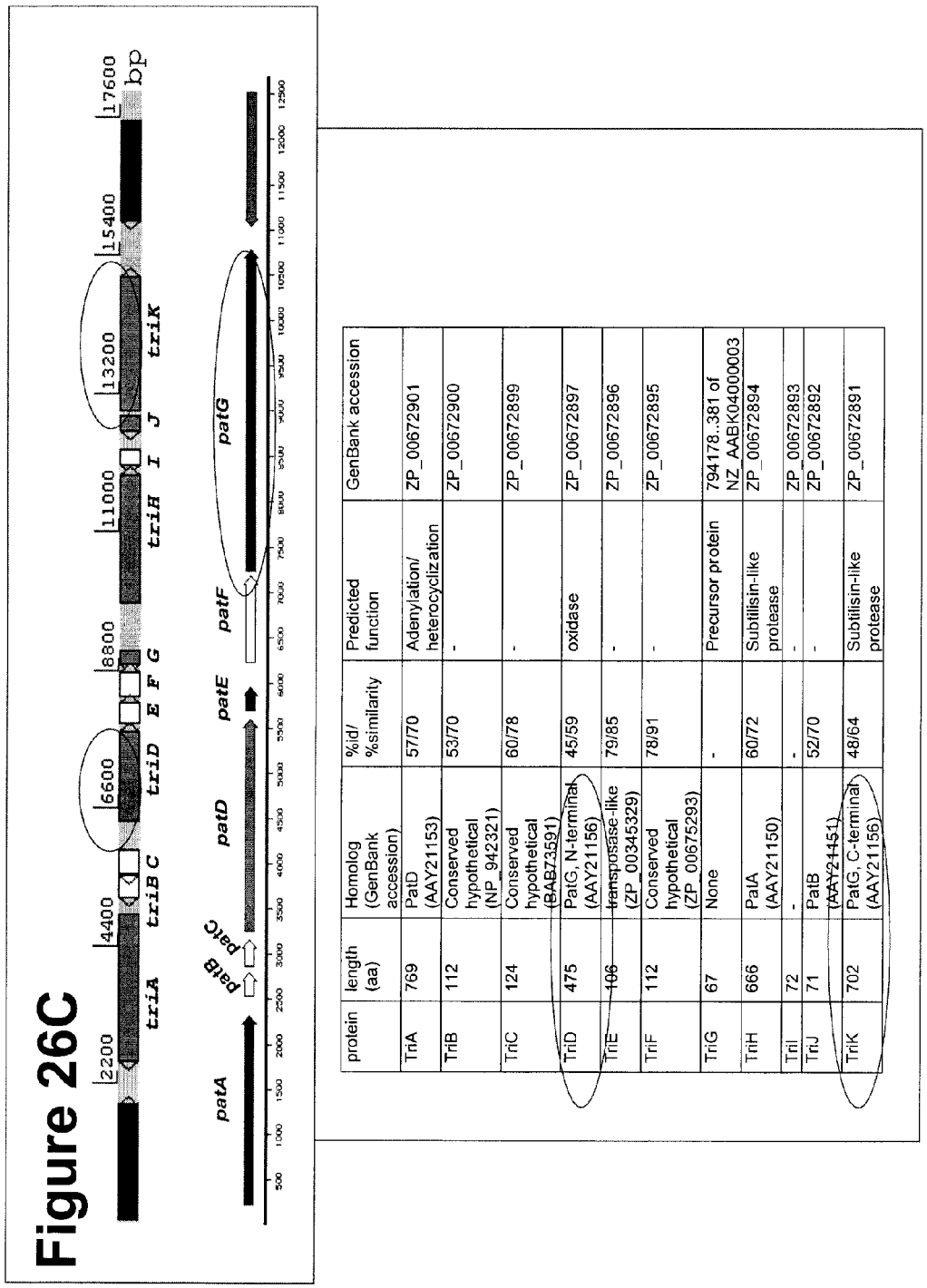
Figure 26D:
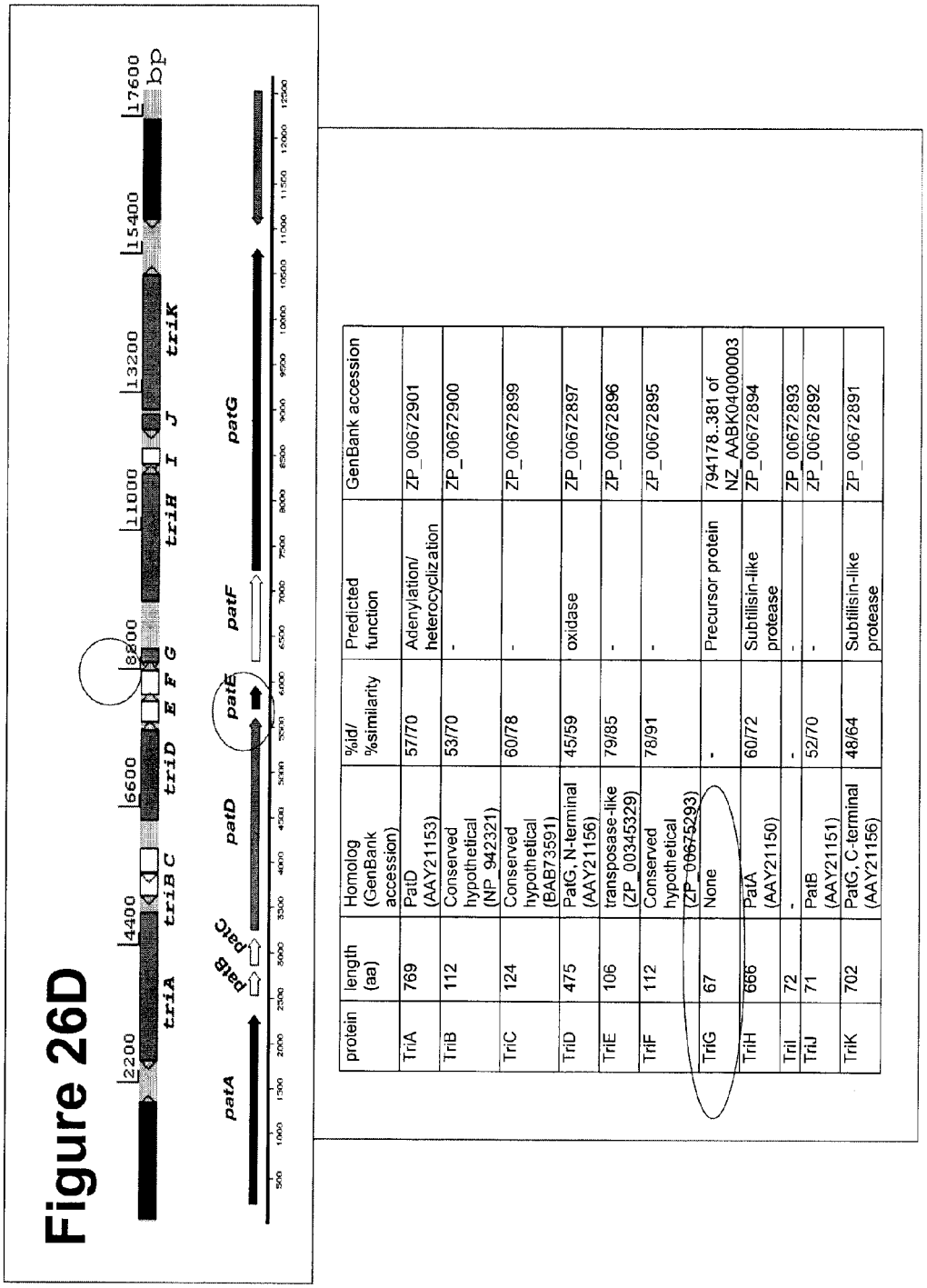

FIG. 25 shows biogenesis, and cyclization/cleavage for PatG and PatA. Also shown are recognition sequences.

FIG. 26 shows that *Trichodesmium erythraeum* contains a pathway similar to pat.

FIG. 27 shows the structure prediction of PatE and TriG. TriG is a PatE homolog, as the coding sequence is different but the recognition sequences are closely related.

Figure 28:
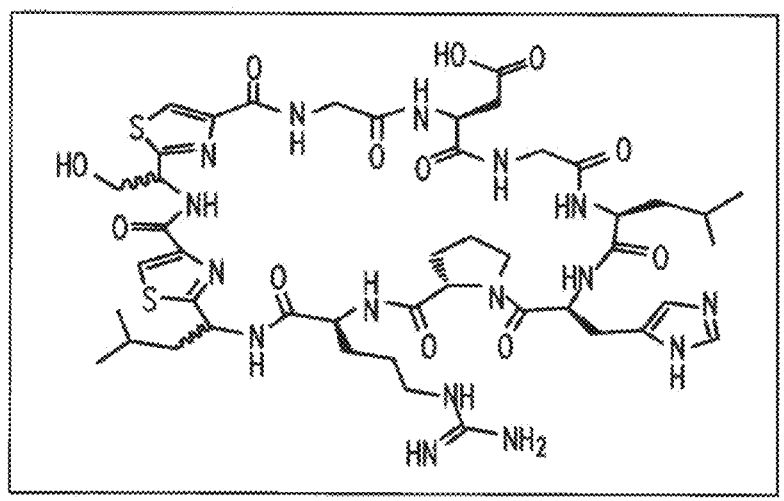
Figure 28:
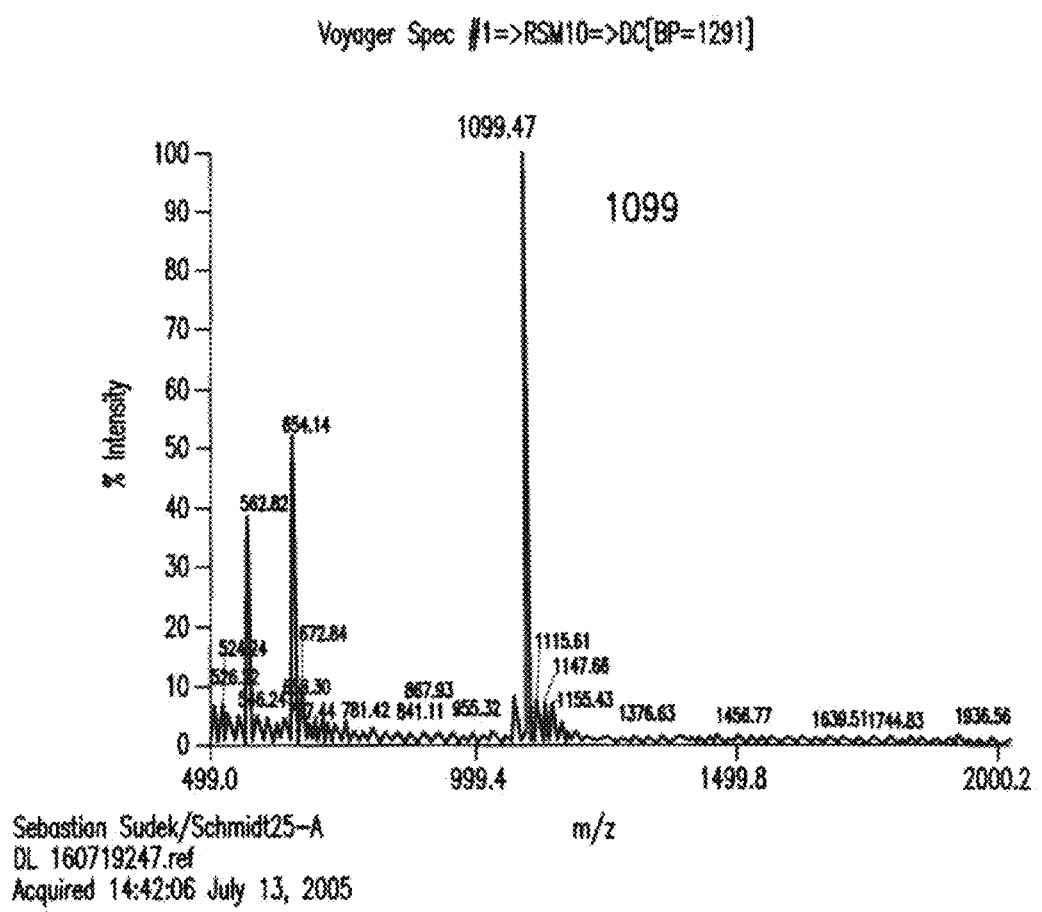

FIG. 28 shows the predicted product trichamide based on the mass using MALDI-TOF, and structure elucidation by FT-MS.

FIG. 29 shows the methodology of structure elucidation, using mass spectrometry and NMR confirmation.

FIG. 30 shows PatE evolution. The DNA is identical except in coding regions. Only Patellamide A region is changed (compared to ulithiacyclamide).

Figure 31:
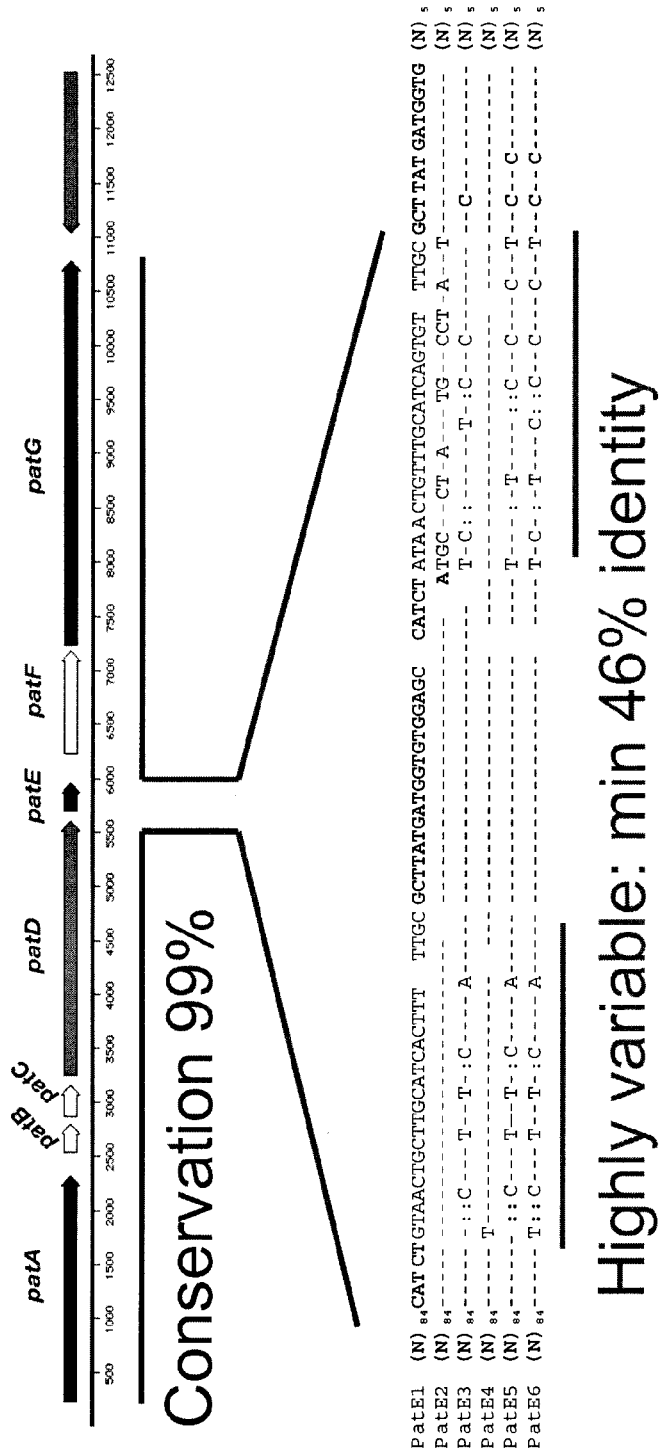

FIG. 31 shows 6 PatE variants. They are 99% identical, except in the exact coding region.

Figure 32:
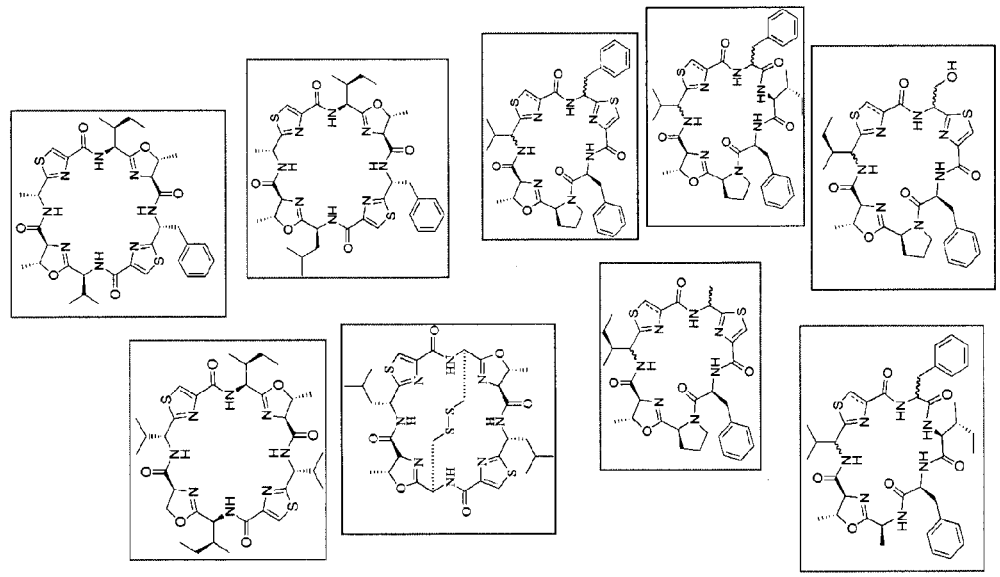

FIG. 32 shows PatE evolution. Various compounds and coding sequences are compared, and shown along with their structures. There is an unprecedented type of np evolution.

Figure 33:
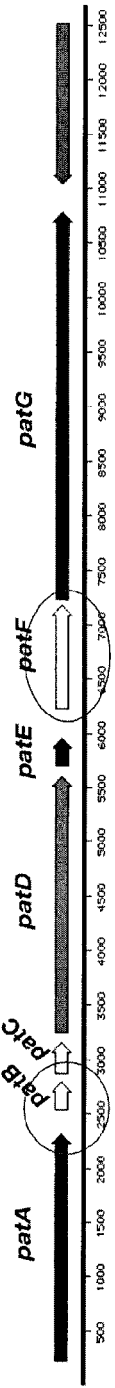

FIG. 33 shows the biochemistry of pat. Importantly, it is shown that the required proteins include PatF.

FIG. 34 shows eptidemnamide synthesis.

Figure 35:
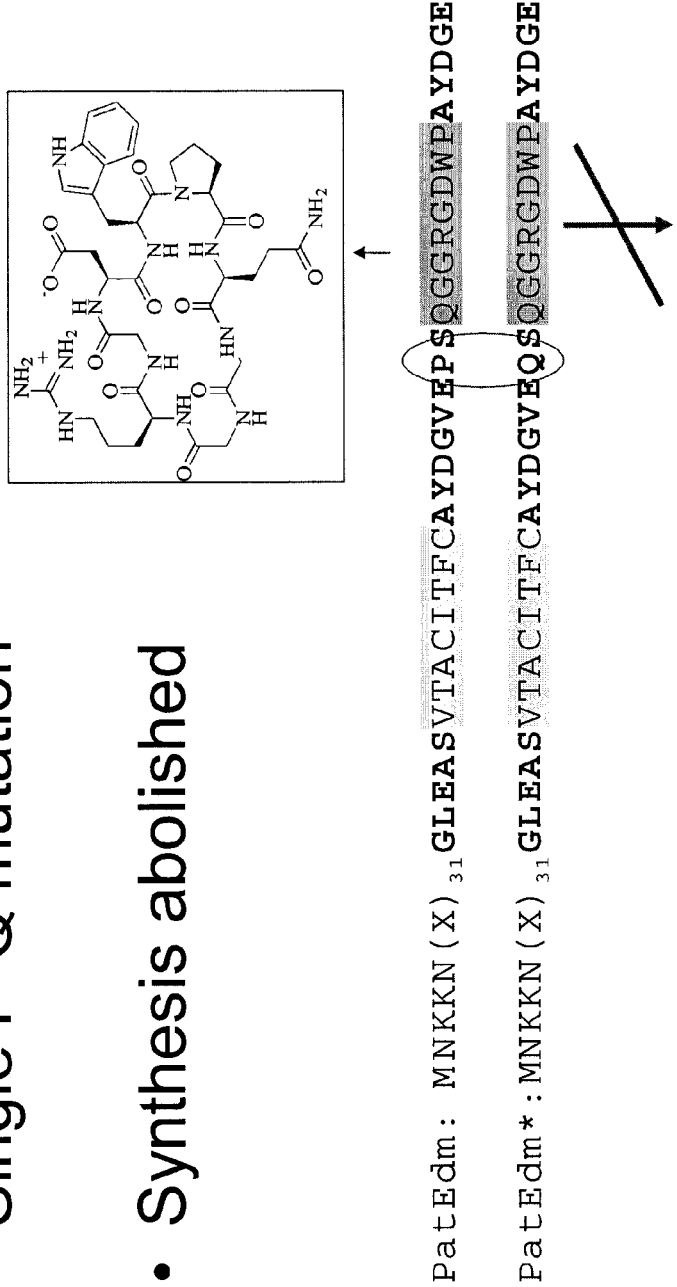

FIG. 35 shows the recognition sequence, and that a single mutation can abolish synthesis.

Figure 36:
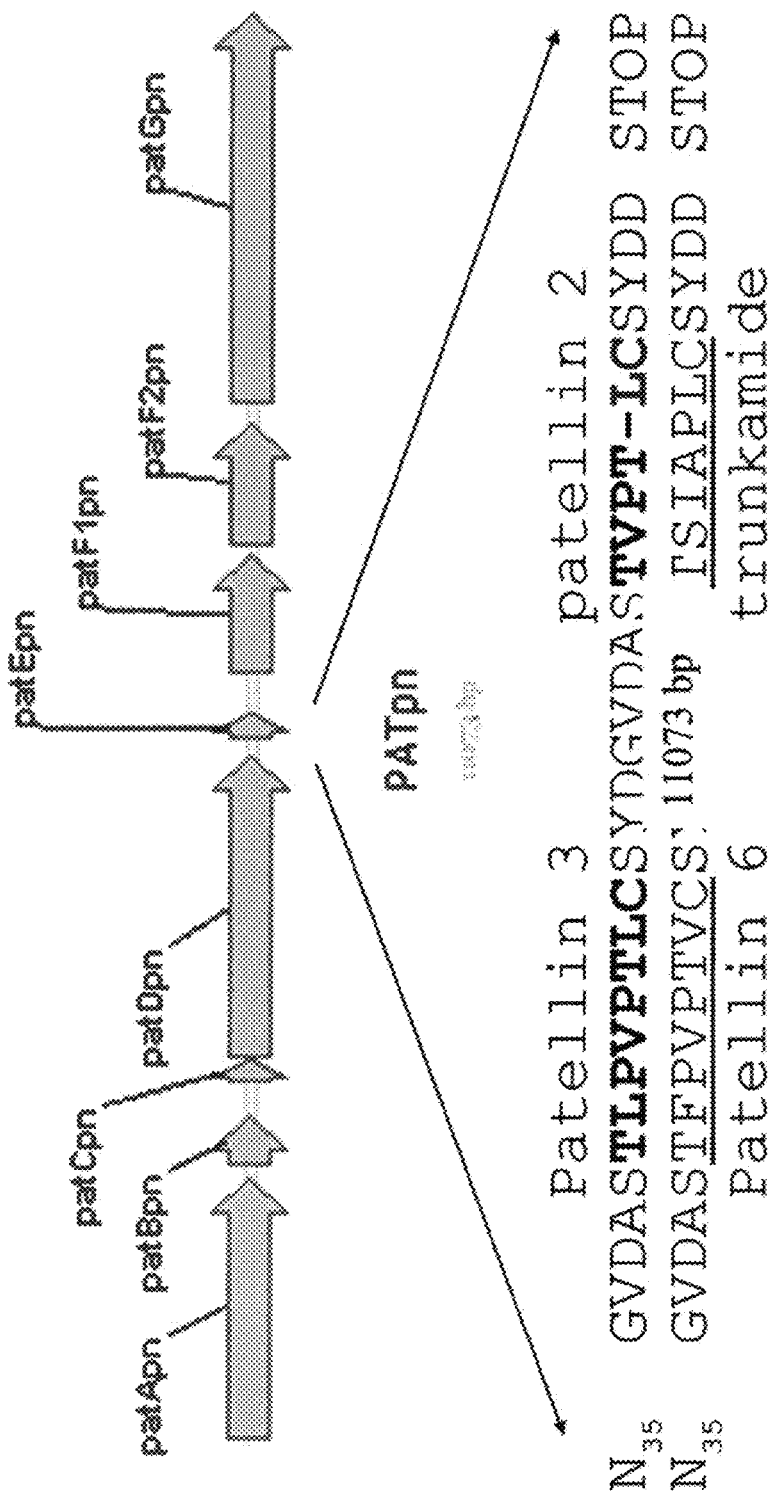

FIG. 36 shows the gene cluster for trunkamide. The first four coding sequences are very similar to those for PatA, PatB, PatC, and PatD. The homolog of PatE, which directly encodes trunkamide, is identical to PatE until about midway through the coding sequence, where there is a clear insertion event leading to the new trunkamide-like sequences. The following ~2 kbp of DNA sequence is not similar to that found in the previously reported patellamide sequence. Following this insertion, the latter half of PatG is present. This contains the protease domain found in patellamides, but it lacks the oxidase found in the patellamide pathway. This was expected, since trunkamide and relatives are not oxidized. However, the remainder of PatG is >95% identical to that of the patellamides. Within this insertion, in addition to the latter half of the new PatE homolog, there are encoded two new proteins. These are both 40-50% identical to the previously described PatF. It appears that at least one of these performs the prenyltransfer reaction important to formation of trunkamide; this is the major difference between these two classes of metabolites. These comprise a unique class of proteins with two functions: heterocyclization of Thr/Ser (in the case of patellamides); and prenylation of Thr/Ser (in the trunkamide family).

Figure 37:
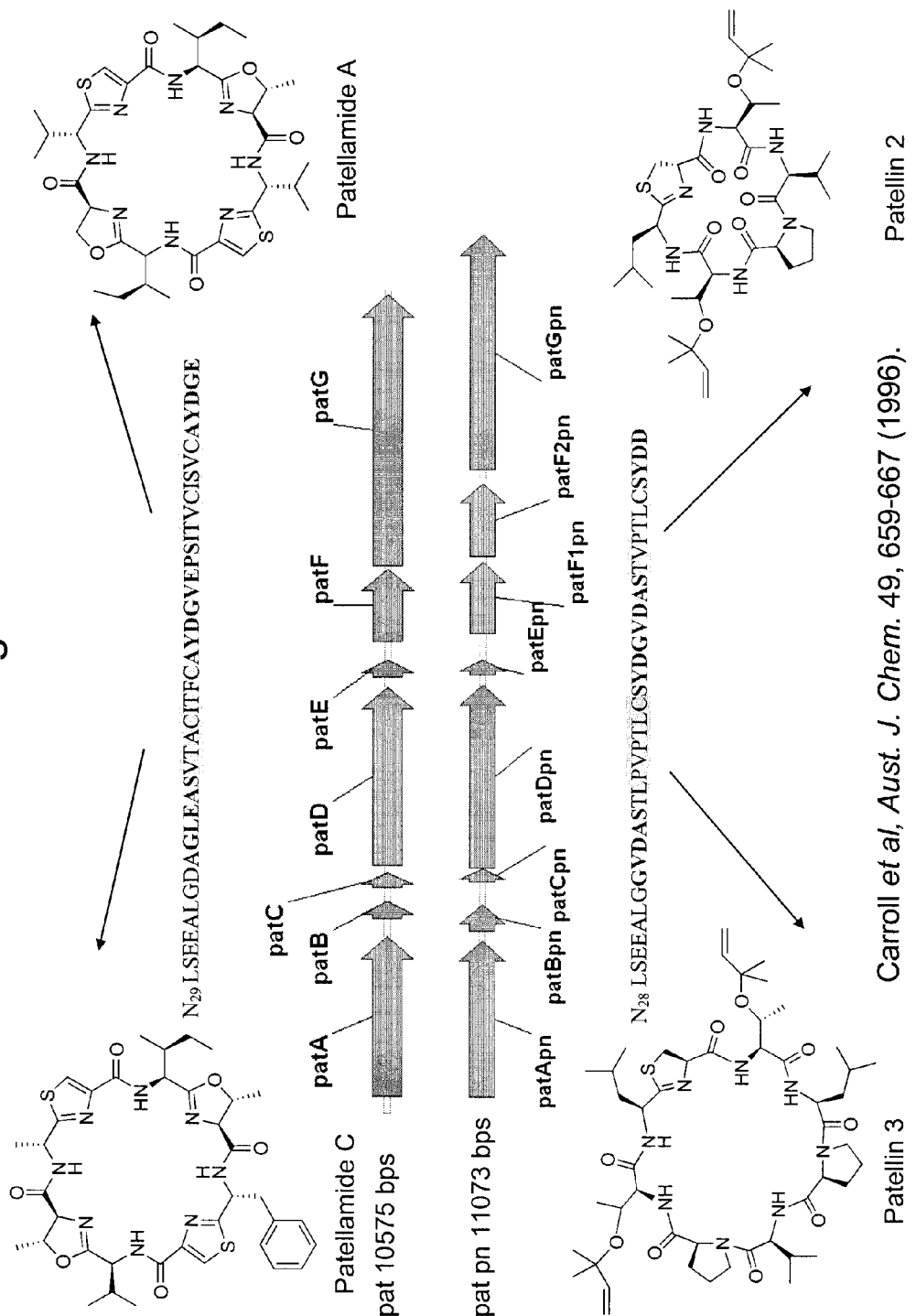

FIG. 37 shows patellamides versus patellin. The bottom cluster (pat pn) was sequenced, which directly encodes patellins 2 and 3. The pathway is very similar (<90% identical) to the previously reported pat pathway, with 2 major differences: 1) patG is missing the oxidase domain; 2) there are 2 copies of patF, both of which are only about 40% identical to the patF from the patellamide cluster.

Figure 38:
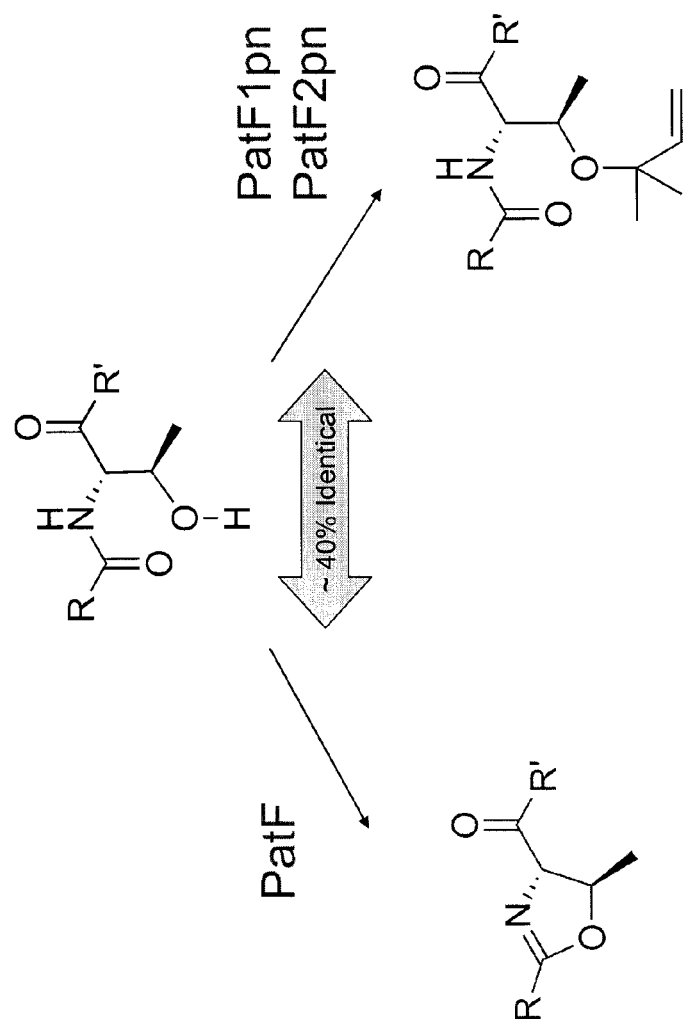

FIG. 38 shows that a new family of enzymes have been identified. In one case, heterocyclization occurs, and in the other, prenylation. Prenylation is extremely important, since cyclic peptide libraries can be prenylated.

Figure 39:
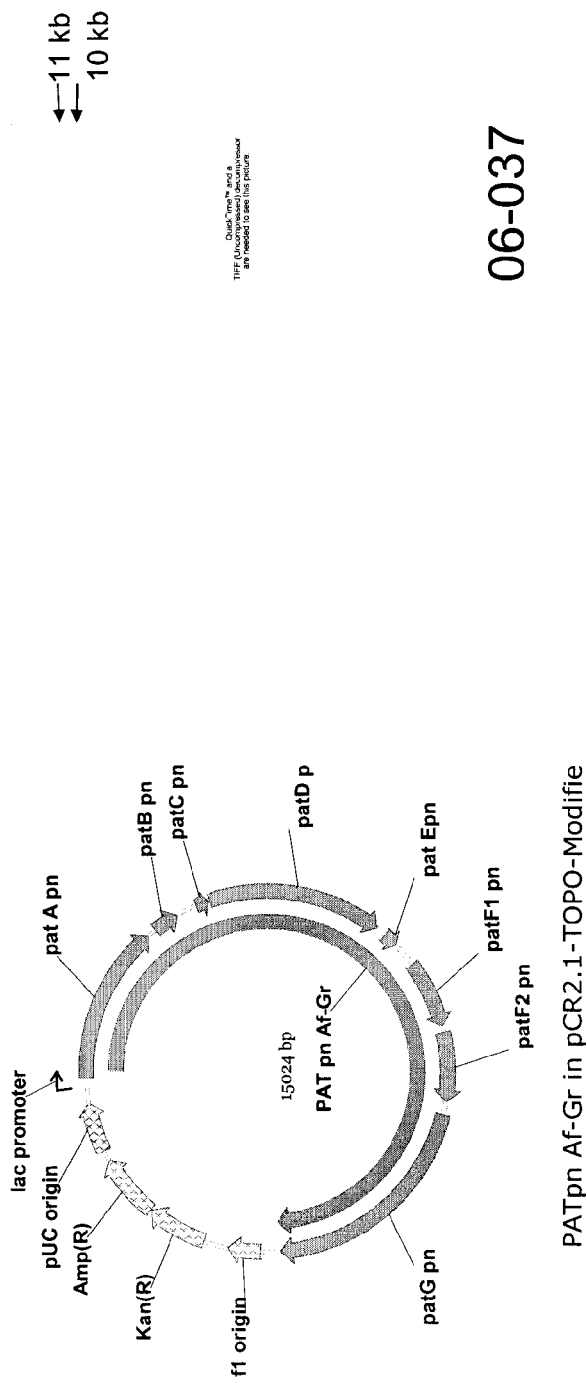

FIG. 39 shows a proof of function of patellin synthesis. The whole gene cluster out of the *Prochloron* bacteria was amplified by PCR and put it into the pCR2.1 TOPO vector (Invitrogen). Expression and chemical analysis was carried out in *E. coli*. Methodology overall was similar to that used for patellamides.

Figure 40:
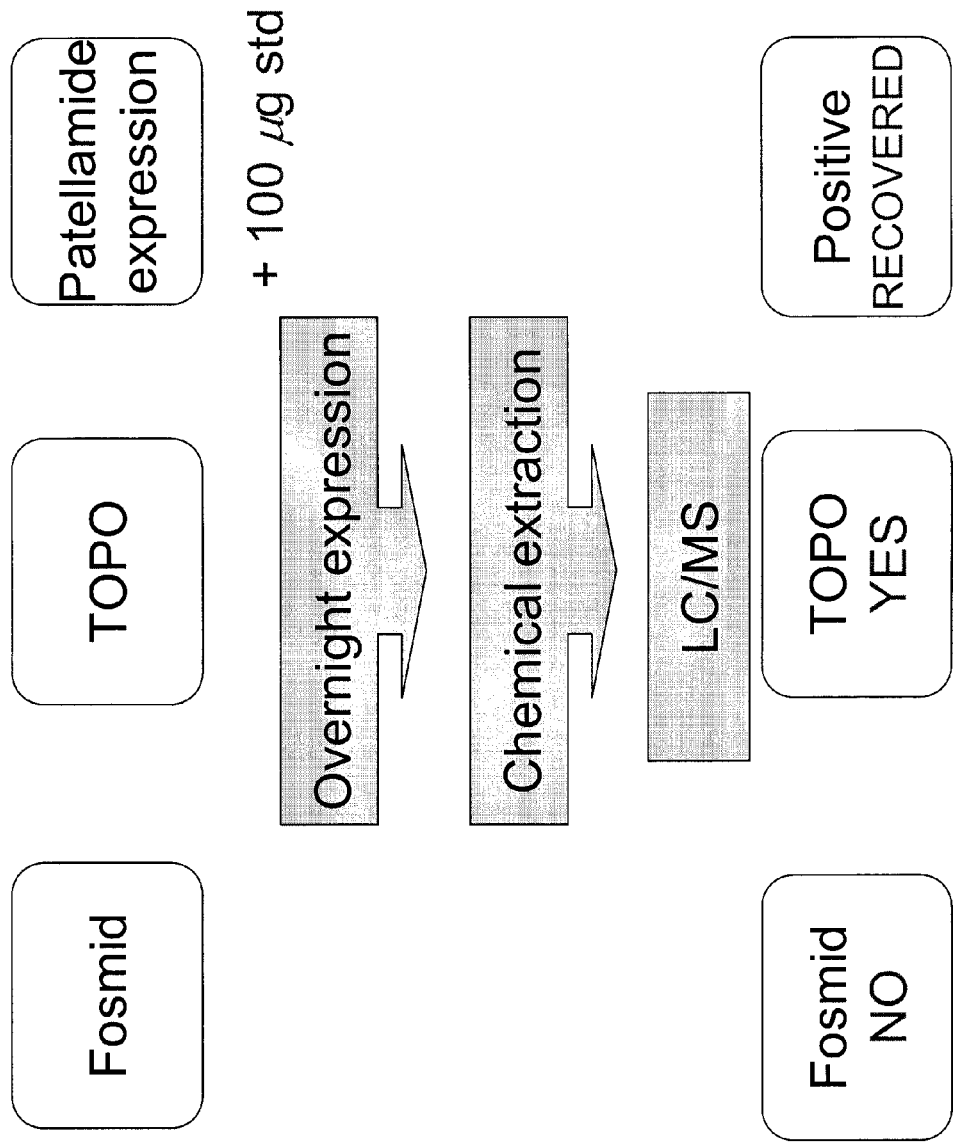

FIG. 40 shows an expression design. By LC-MS, the TOPO clone could make patellins 2 and 3, proving that the identified cluster is necessary and sufficient for patellin synthesis.

Figure 41:
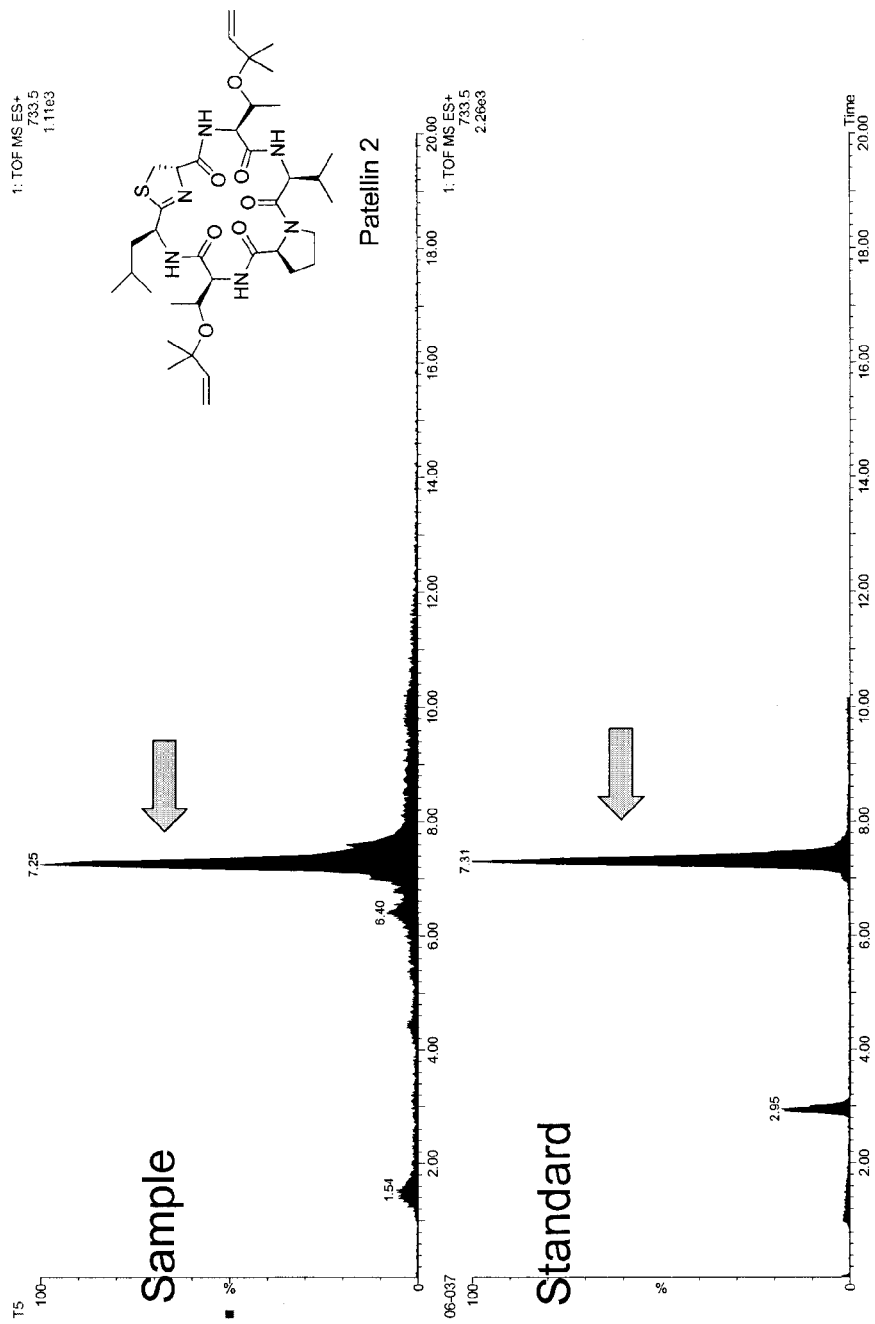

FIG. 41 shows heterologous expression of Patellins 2 and 3. Shown is the LC-MS run (y-axis: % abundance; x-axis: time (min)). The top panel is an extract of *E. coli* containing the patellin cluster. The bottom is an extract of whole ascidian containing patellins (positive control).

Figure 42:
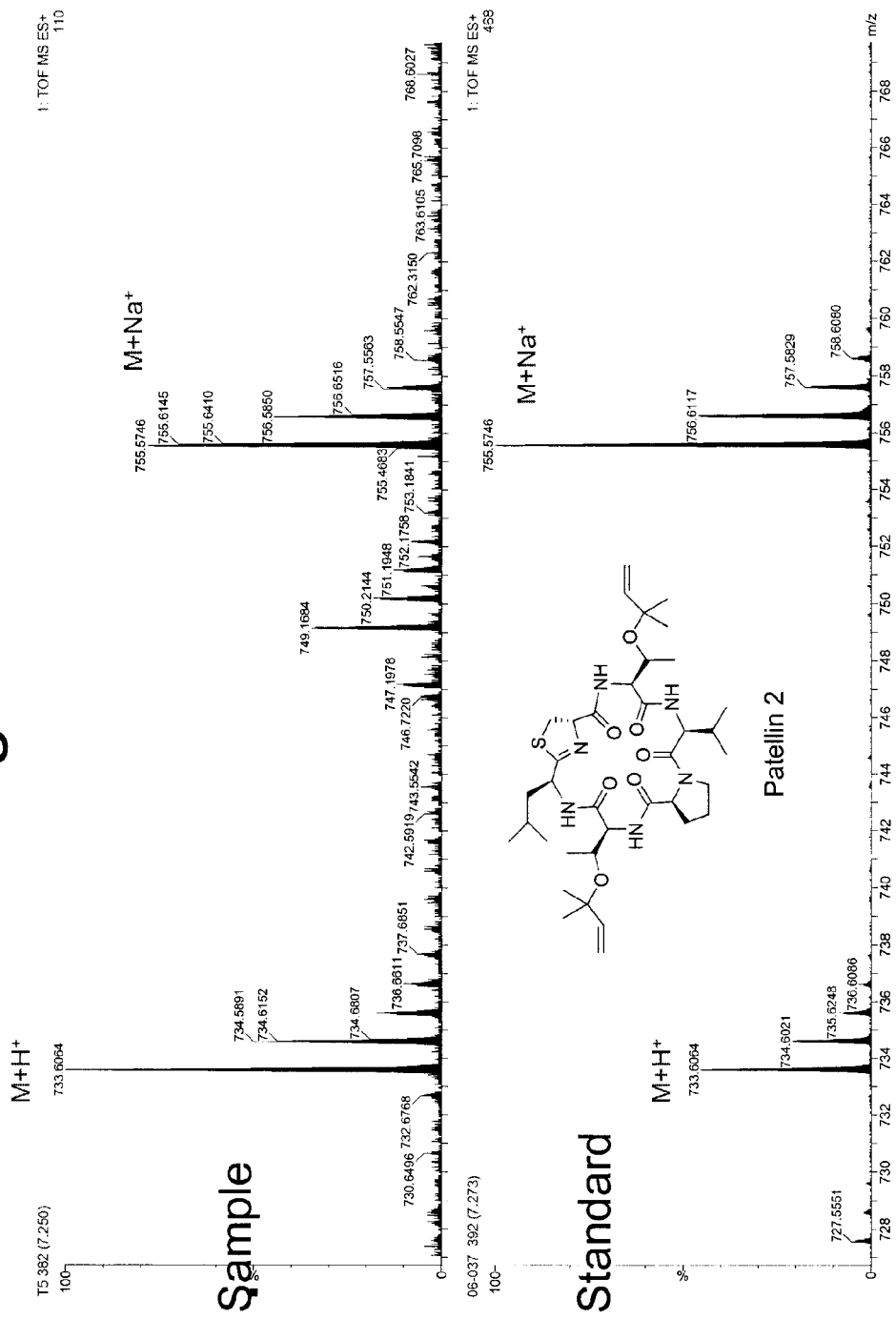

FIG. 42 shows heterologous expression of Patellin 2. Mass analysis of this peak clearly shows that patellin 2 is synthesized in *E. coli* when the patellin gene cluster is present.

Figure 43:
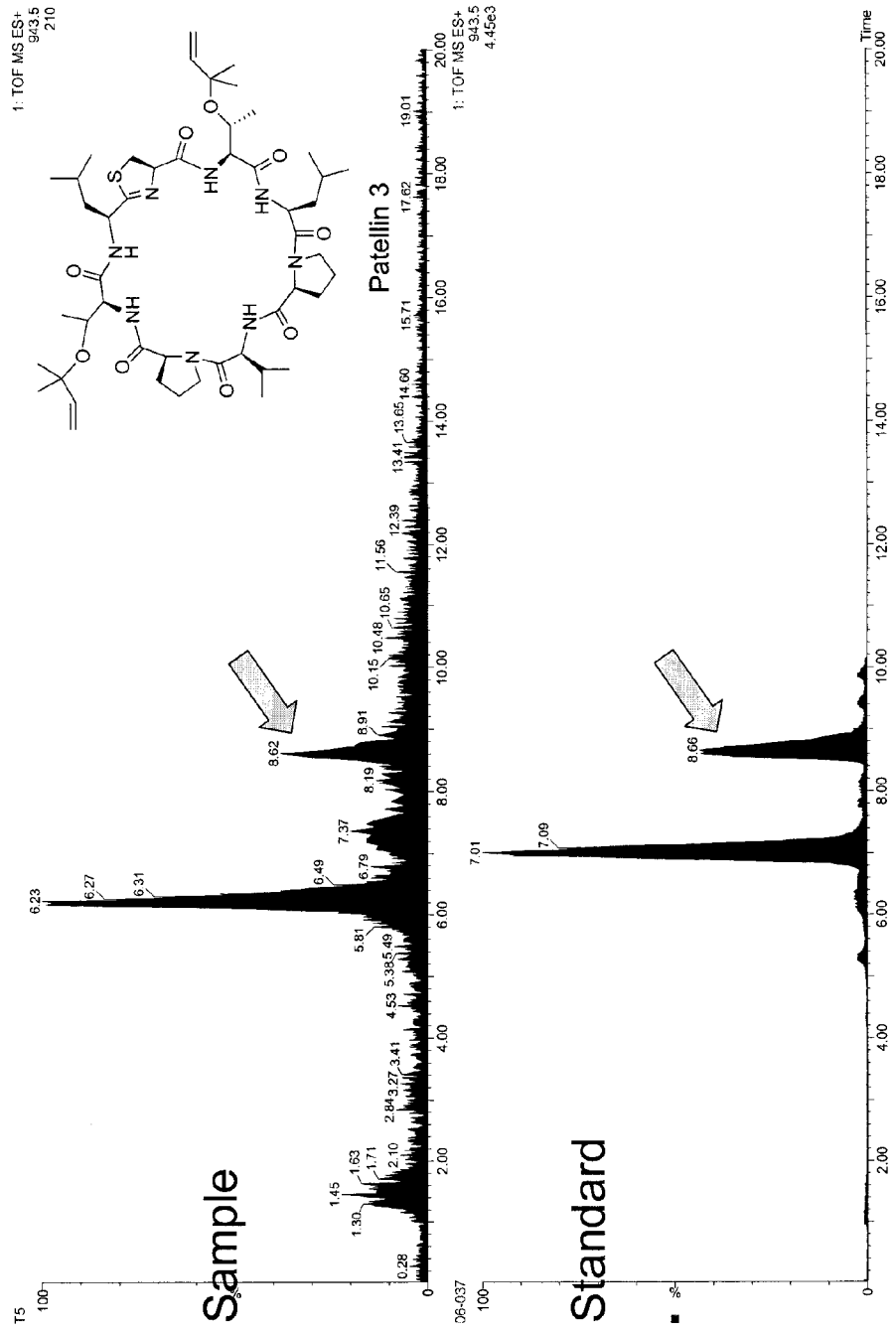

FIG. 43 also shows heterologous expression of Patellin 3. Mass analysis of this peak clearly shows that patellin 3 is synthesized in *E. coli* when the patellin gene cluster is present.

Figure 44:
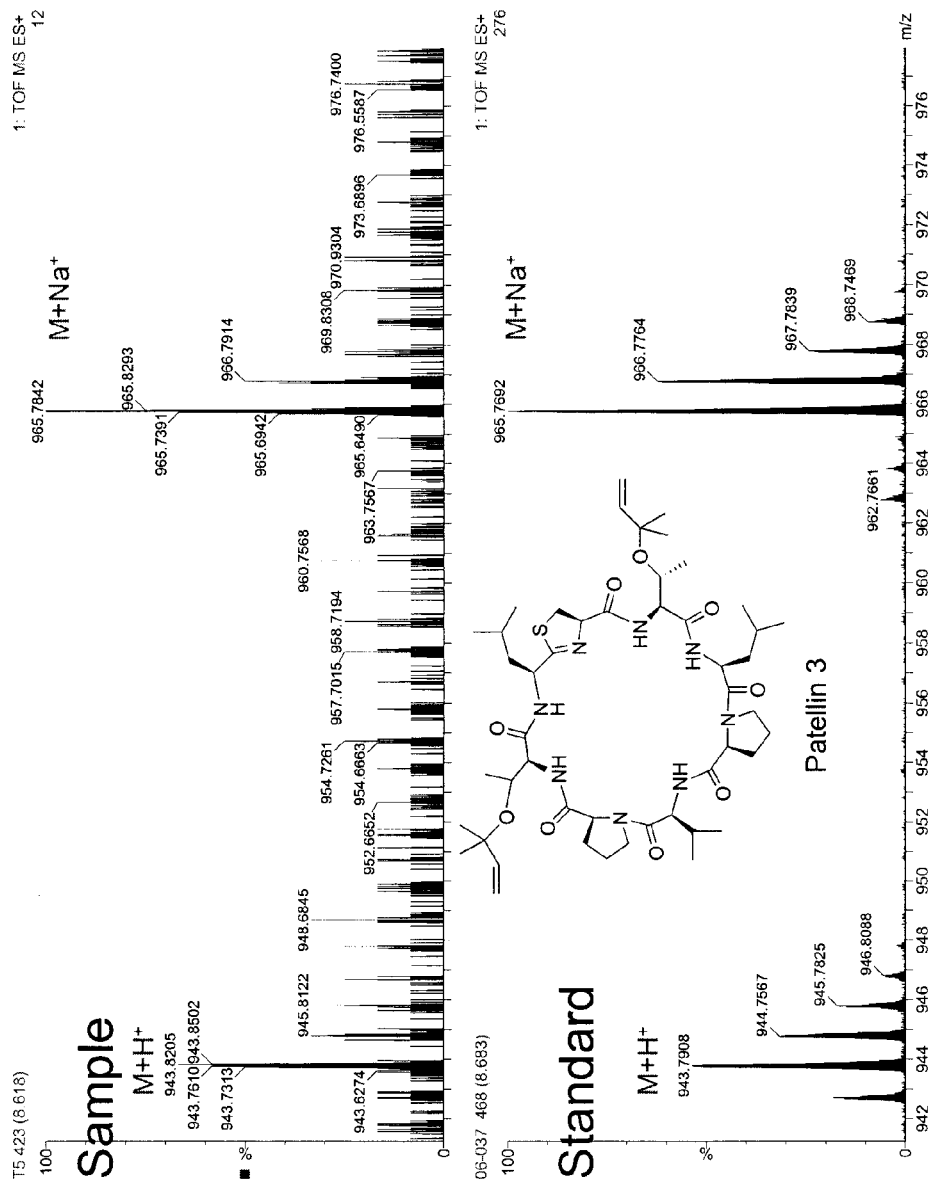

FIG. 44 shows that patellin 3 is clearly synthesized when the identified gene cluster is used.

Figure 45:
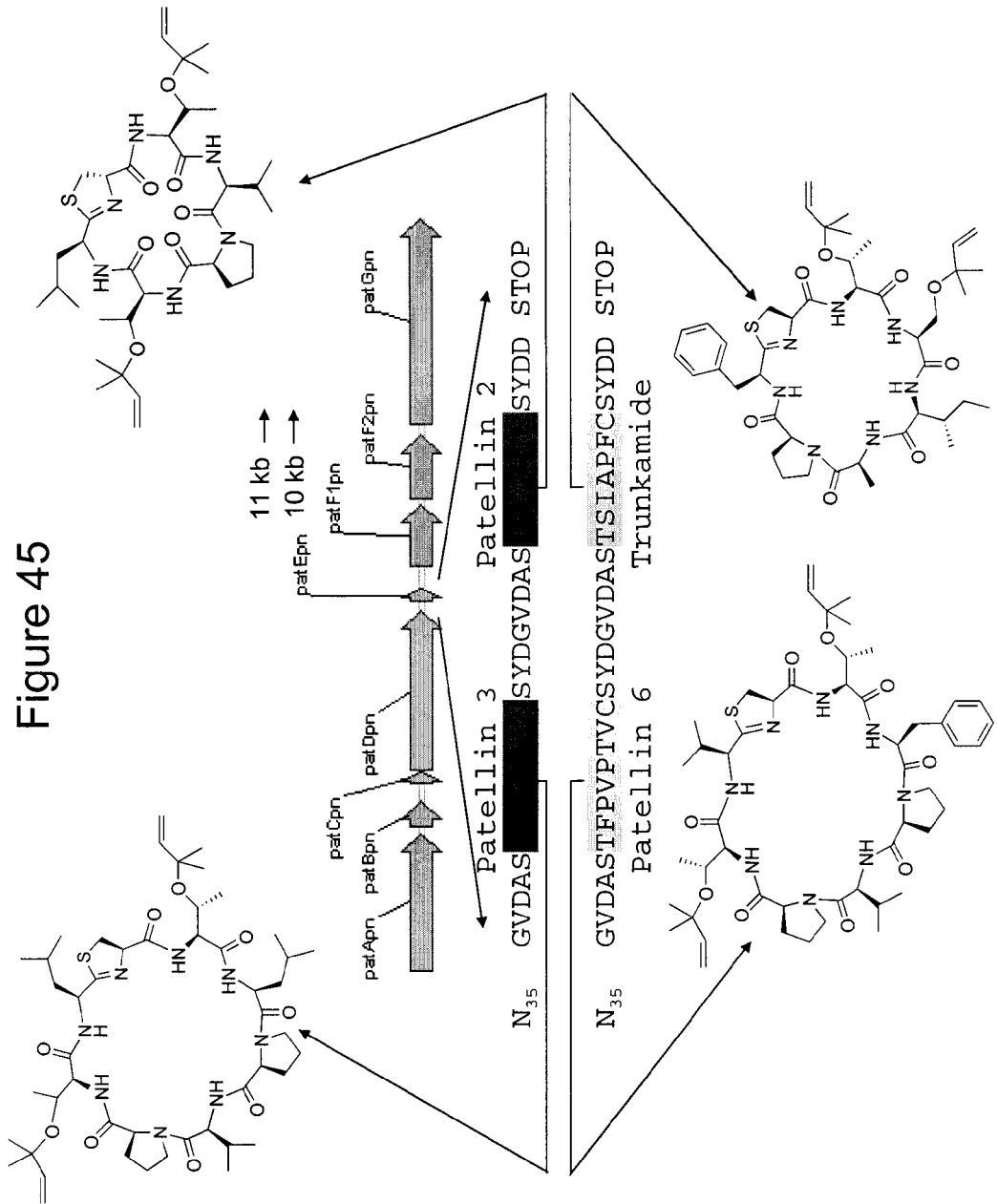

FIG. 45 shows trunkamide. A gene cluster that produces trunkamide (the clinically important molecule) and patellin 6 was cloned. The pathways are nearly identical, except that they make different molecules.

Figure 46:
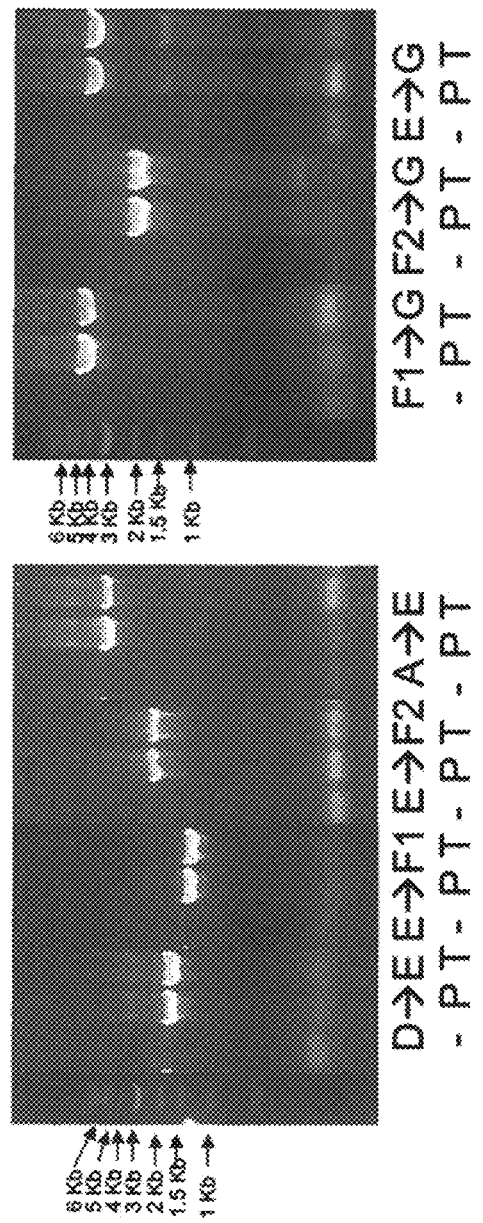

FIG. 46 shows trunkamide cluster verification. To address the orientation of the cluster, PCR with primers from the patellin cluster covering the whole cluster in pieces was used. This clearly indicates that these clusters are nearly identical, with the exception of the products synthesized.

VI. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "cyclic polypeptide" is a type of conformationally restrained polypeptide that, as its name suggests, contains a cyclic polymer of amino acids. The term "cyclic polypeptide" is used to describe a polypeptide (including a cyclic peptide) that is circularized via a peptide bond between the N and C terminal amino acids of a linear polypeptide (as described in U.S. published patent application 20040014100, for example).

The term "randomized amino acid sequence" refers to a polypeptide having an amino acid sequence that is at least partially randomized, including fully randomized. When made recombinantly, a library of polypeptides having randomized amino acid sequences usually contains polypeptides having any of the naturally occurring amino acids, or any subset thereof, present into at least one or all positions (e.g., at last 1, 2, 3, 4, 5, about 8, about 10, about 15, about 20, usually up to at least 100 or more positions) of the polypeptide. Polypeptides having a randomized amino acid sequence are usually produced using synthetic nucleic acids that contain any of the four nucleotides, or a subset thereof, in at least one or all positions of the polynucleotide.

A "library" of cells is a plurality of cells. Such a library may be a mixture of different cells, or may contain cells that are separated from each other (e.g., in the wells of a multi-well plate).

The terms "pool" or "mixture", as used herein, refers to a combination of elements, e.g., cells or polypeptides, that are interspersed in two or three dimensions and not in any particular order. A mixture is homogeneous and not spatially separable into its different constituents. Examples of mixtures of elements include a number of different polypeptides that are present in the same solution (e.g., an aqueous solution). In other words, a mixture is not addressable. To be specific, an arrayed library of polypeptides, as is commonly known in the art, is not a mixture of polypeptides because the elements of the library are spatially distinct and the array is addressable.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a receptor modulator that can provide for enhanced or desirable effects in the subject (e.g., reduction of pathogen load, beneficial increase in a physiological parameter of the subject, reduction of disease symptoms, etc.).

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. General

Patellamides

Patellamides are a family of N—C terminally cyclized peptide natural products isolated from marine ascidians (Ireland, C. M.; Durso, Jr., A. R.; Newman, R. A.; Hacker, M. P. J. Org. Chem. 1982, 47, 1807-1811) (FIG. 1). These peptides and their relatives often contain thiazole, thiazoline, and oxazoline heterocycles derived from Cys, Thr, and Ser. They form a large family of molecules, some of which are relatively unrelated to the parent patellamide structure (Davidson, B. S. Chem. Rev. 1993, 93, 1771-1791; Sings et al. Ind. Mirobiol. 1996, 17, 385-396; Schmidt et al. J. Nat. Prod. 2004, 67, 1341-1345). To investigate the biosynthesis and biotechnological utility of this family, the patellamide A/C biosynthetic gene cluster, pat, was cloned and synthesized from an uncultivated bacterial symbiont of ascidians (FIG. 1). When expressed in *E. coli*, pat led to the production of very small amounts of patellamides (Long et al. ChemBioChem, 2005, 6, 1-7). This represented the first fully validated natural product pathway from uncultured symbionts.

pat is composed of seven coding sequences, patA-G, which had little to no similarity with other characterized gene clusters. PatE encoded the cyclic peptides, patellamides A and C, directly on a single prepeptide (FIG. 1). Putative start- and stop-cyclization recognition sequences were found, leading to the speculation that the coding sequences themselves could be modified to produce new, cyclic peptides.

pat was originally cloned from an environmental (uncultured) bacterial sample, and the intact pathway produced low levels of patellamides. Therefore, patA-G were cloned and expressed in compatible DUET vectors in *E. coli*. On the basis of sequence analysis, it was predicted that PatA, PatD, PatE, and PatG would be required for patellamide biosynthesis. PatE, as the direct patellamide prepeptide, is obviously a required precursor. PatD has low sequence similarity to a series of enzymes involved in thiazole formation in a group of microcins, (Roy et al. Nat. Prod. Rep. 1999, 16, 249-263; Milne et al. Biochemistry 1999, 38, 4768-4781; Kelleher et al. Biochemistry, 1999, 38, 15623-15630) indicating that it is likely required for the same function in pat. PatA and PatG both contained serine protease domains that were predicted to be involved in maturation (Chatterje et al. A. Chem. Rev. 2005, 105, 633-683) and cyclization of patellamides. In addition, PatG harbored an N-terminal domain with homology to FAD-dependent oxidases, indicating that it would likely be required to synthesize thiazole from thiazoline. The other three predicted coding sequences, PatB, PatC, and PatF, had no significant similarity to any protein with known function.

It was discovered that patE2, which was identical to patE except that the nucleotides encoding patellamide A were neatly replaced with those encoding the known compound, ulithiacyclamide. patE2 was used for the studies described, in part because ulithiacyclamide was much more readily detected in comparison to patellamide A or C. In order to achieve better production with patE2, all pat genes were removed from their native context and placed under control of individual T7 promoters in *E. coli*. Production of patellamides and ulithiacyclamide was monitored by HPLC-ESI-MS, using an authentic standard of ulithiacyclamide as a positive control.

Figure 2:
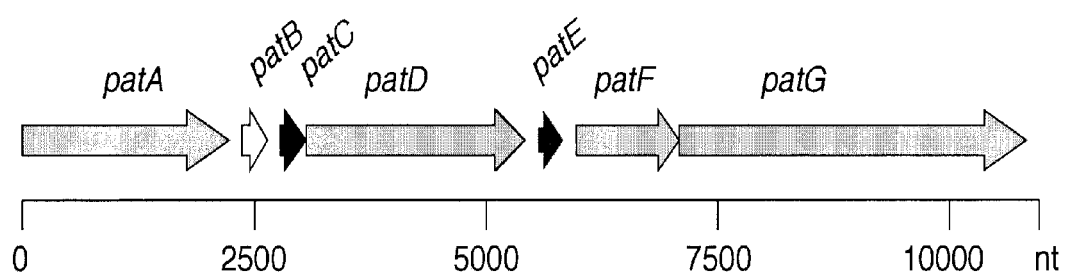
FIG. 2 shows the pat pathway. Genes for required enzymes are shown in blue and the precursor peptide gene is red. patB (white) increases peptide yield, while patC (black) is apparently not required for biosynthesis.
Figure 3:
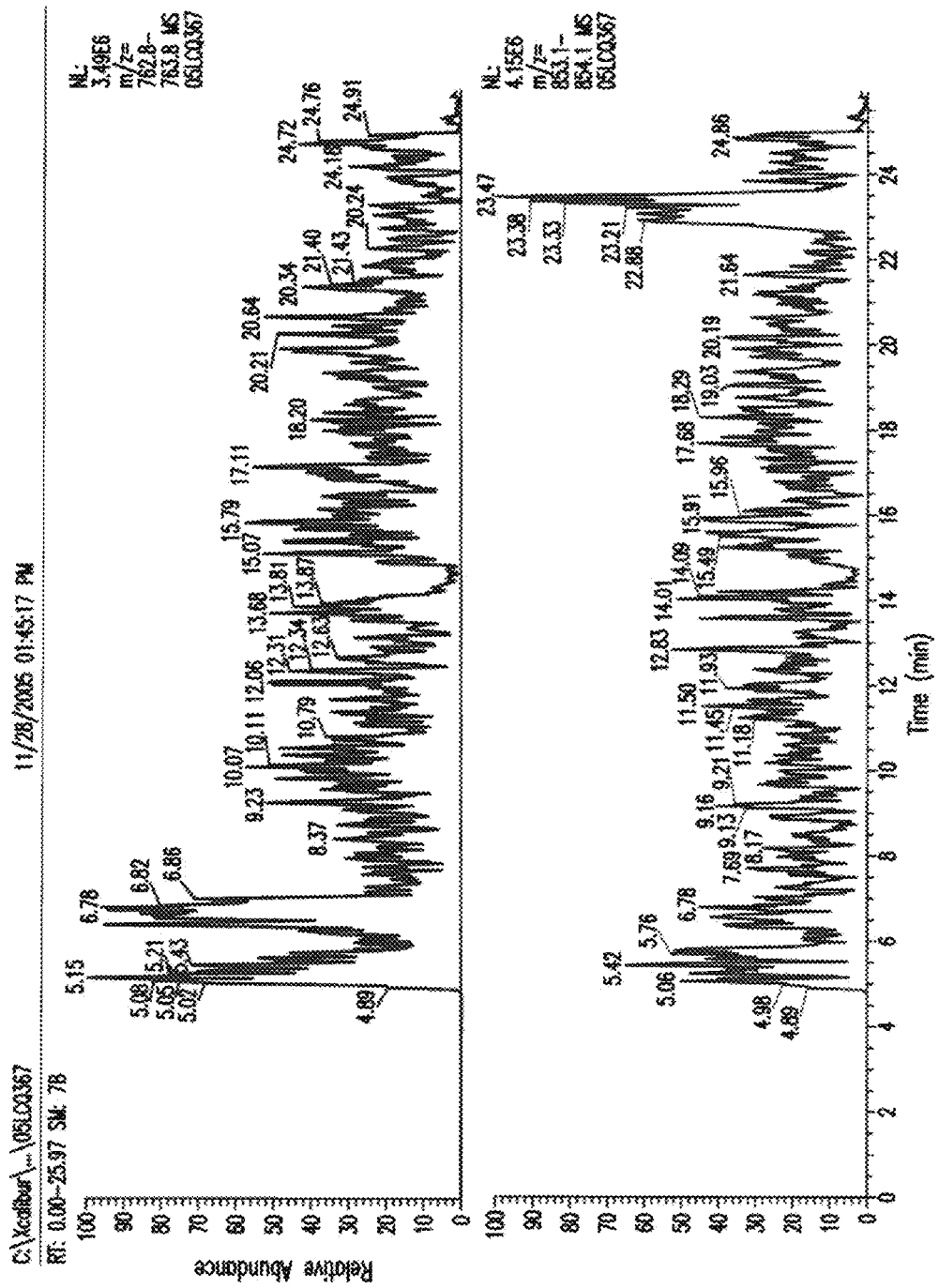
FIG. 3 shows HPLC-MS traces for gene combinations ADEG (top), ABDEFG (middle) and ABDEdrmFG (bottom), monitored on mass 763 (upper) and 853 (lower).
Figure 3:
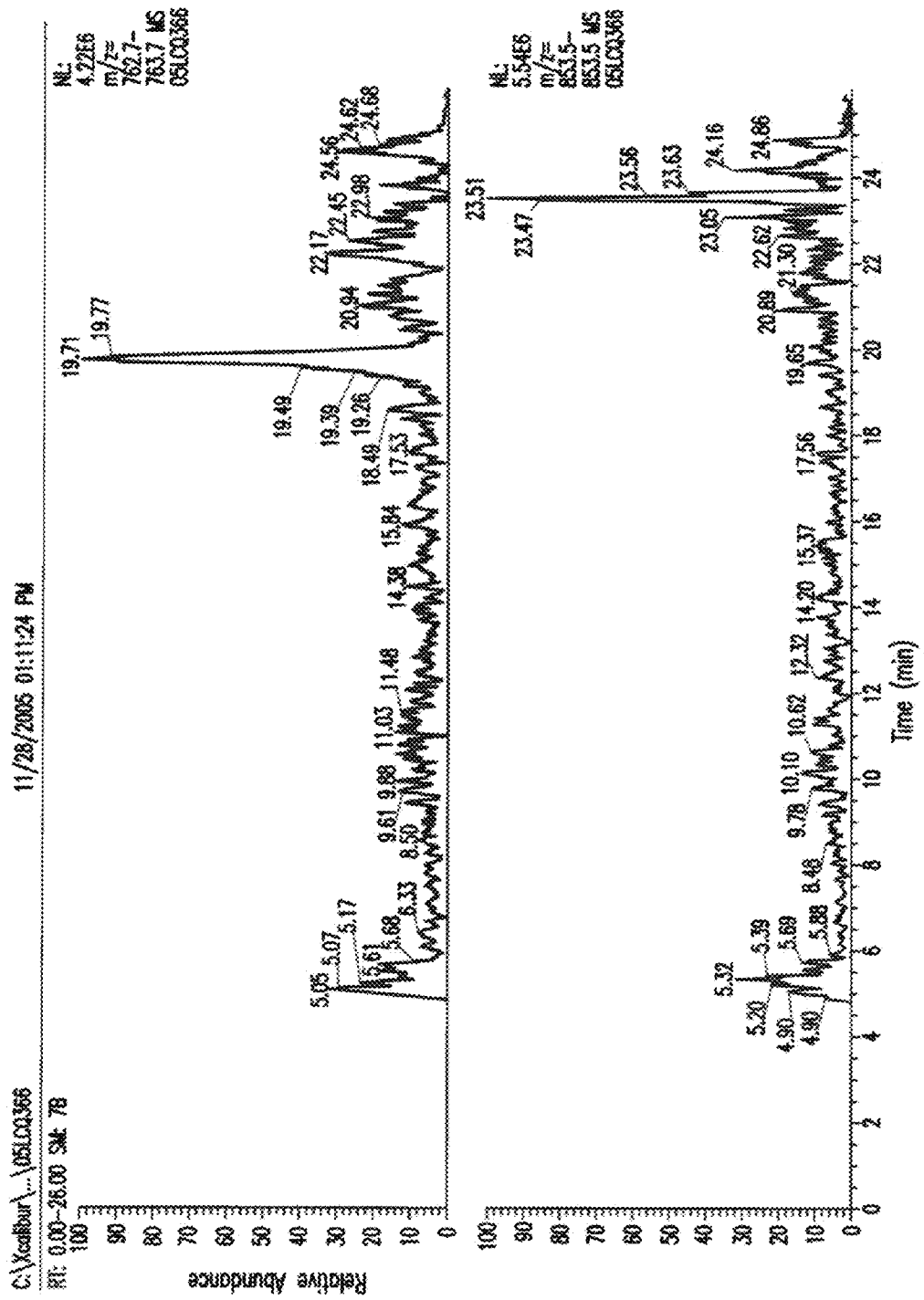
Figure 3:
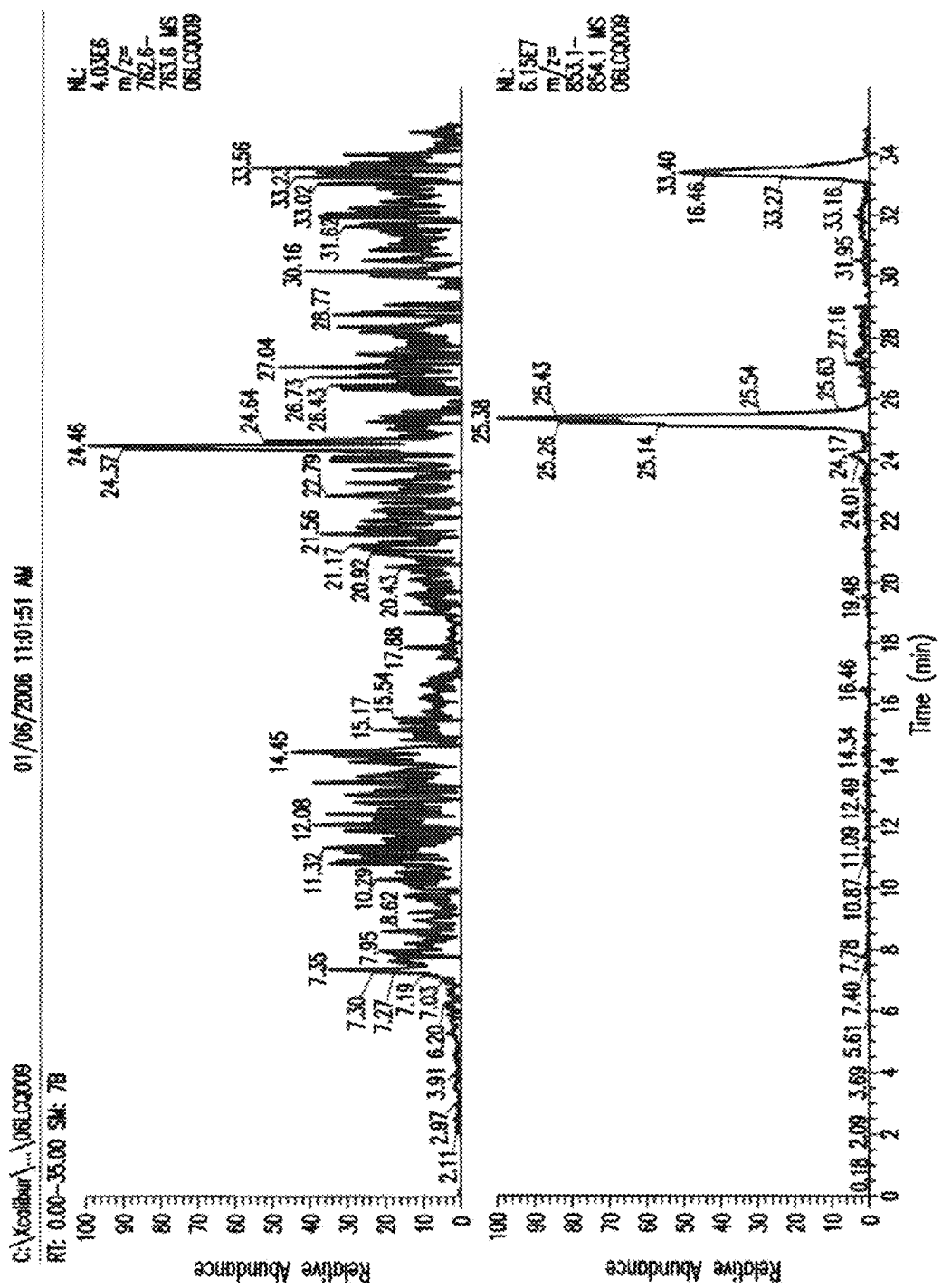

Co-expression of the full gene set patA-G followed by subtraction of genes one at a time led to the discovery that PatADE2G was required, but that PatF was also required for patellamide C/ulithiacyclamide production. PatB and PatC, by contrast, were not necessary for the production of the patellamides, although PatB increased the detected yield. Strains that lacked any of the proteins PatADE2FG did not make patellamides. On this basis, the minimal gene set was defined as patADEFG (FIG. 2).

A series of pat relatives encoding both new and known products were identified. Only the patellamide-like coding sequences were mutated, while other sequences remained identical. However, most of the mutations were relatively conservative, in that aliphatic amino acids could be swapped, and Thr and Ser were interchangeable. Thus, it was sought whether less conservative mutations could be tolerated by the pat system.

A mutant, patEdm, was synthesized in which the entire ulithiacyclamide sequence was swapped with a sequence encoding "eptidemnamide". This new peptide sequence has no biosynthetic precedent in the literature, is not related in any way to known patellamide relatives, and was meant to be an amide-cyclized relative of the clinically used disulfide-bridged anticoagulant, eptifibatide (Curran, M. P.; Keating, G. M. Drugs 2005, 65, 2009-2035). In contrast to patellamides, eptidemnamide contains charged and polar residues and new hydrophobic amino acids Trp and Gly. This new peptide was designed in order to define the sequence tolerance of PatADFG in one step.

patEdm was synthesized in a single round of mutational PCR, (Kunkel, T. A. Proc. Nat. Acad. Sci. USA 1985, 82, 488-492) and its identity was verified by sequencing. In addition, a mutant patEdm* was discovered in a clone library that was very similar to patEdm but contained a $P^{56}$-Q mutation in the recognition sequence immediately upstream of eptidemnamide. Both patEdm and patEdm* were cloned into pRSF-DUET vector and co-expressed with patABDFG. By HPLC-ESI-MS analysis, the strain containing patEdm produced eptidemnamide, while the patEdm* strain did not produce any detectable new compound. From the patEdm-expressing strain, eptidemnamide was isolated, and its structure verified by NMR and ESI-FTMS. These experiments demonstrate the crucial nature of the recognition region in controlling peptide cyclization, while also showing that the coding sequences of these peptides can be varied greatly.

The absolute configuration of the new compound can be all L, based upon the following consideration: In all cases, patellamides and relatives contain L-amino acids except adjacent to thiazole, in which case D- or L-amino acids are present. As noted by numerous synthetic and natural products chemists, this position is notoriously labile, undergoing racemization under many different conditions (Milne et al. Org. Biomol. Chem. 2006; Wipf et al. J. Am. Chem. Soc. 1998, 120, 4105-4112).

The experiments described above are useful in the enzymatic synthesis of cyclic peptide libraries by allowing the rapid construction of C—N terminally amide-linked cyclic peptides on a reasonable scale. In addition, the biosynthetic gene set has been defined, facilitating a complete biochemical analysis of the unique steps involved in the synthesis of this family of compounds. Finally, numerous compounds have been isolated from marine invertebrates, many with novel architectures and functional groups (Blunt et al. Nat. Prod. Rep. 2006, 23, 26-78; Newman et al. J. Nat. Prod. 2004, 67, 1216-1238; et al. Mol. Cancer. Ther. 2005, 4, 333-342).

Also disclosed is the enzymatic synthesis of prenylated peptide libraries using those peptides disclosed herein.

Trichamide

A gene cluster for the biosynthesis of a new small cyclic peptide, dubbed trichamide, was discovered in the genome of the global, bloom-forming marine cyanobacterium *Trichodesmium erythraeum* ISM101 because of striking similarities to the previously characterized patellamide biosynthesis cluster. The tri cluster consists of a precursor peptide gene containing the amino acid sequence for mature trichamide, a putative heterocyclization gene, an oxidase, two proteases and hypothetical genes. Based upon detailed sequence analysis, a structure was predicted for trichamide and confirmed by Fourier-transform mass spectrometry. Trichamide consists of 11 amino acids, including two cysteine-derived thiazole groups, and is cyclized by an N—C terminal amide bond.

*Trichodesmium* is a genus of marine diazotrophic, non-heterocysteous cyanobacteria. It occurs throughout the open waters of oligotrophic tropical and subtropical oceans and forms filaments (trichomes) of 20-200 cells that can further aggregate into colonies several millimeters across. *Trichodesmium* can form enormous blooms in excess of 100,000 $km^2$ (Karl et al. 2002. Dinitrogen fixation in the world's oceans. *Biogeochemistry* 57/58: 47-98), which are most commonly composed of *T. erythraeum* and *T. thiebautii*. *Trichodesmium* sp. have been the subject of intense research mainly for two reasons. First, they contribute a significant portion (40% or more) to global oceanic nitrogen fixation, thereby directly affecting the biogeochemical carbon flux in tropical oceans with implications for the world's climate. Second, massive coastal *Trichodesmium* blooms have been reported to have toxic effects, both directly on invertebrates (Guo C., P. A. Tester. 1994. Toxic effect of the bloom-forming *Trichodesmium* sp. (Cyanophyta) to the copepod *Acartia tonsa*. *Nat. Toxins* 2: 222-227; Hawser S. P., J. M. ONeil, M. R. Roman, G. A. Codd. 1992. Toxicity of blooms of the cyanobacterium *Trichodesmium* to zooplankton. *J. Appl Phycol* 4: 79-86) and on humans ("*Trichodesmium* or Tamandare fever", (Sato et al. *Trab. do Instit. Oceanogr. Univ. Fed de Pernambuco Recife* 5/6: 7-50) as well as indirectly by inducing blooms of other organisms (Devassy et al 1979. Indian J. Mar. Sci. 8: 88-93; Lenes et al. 2001. Limnol. Oceanogr. 46: 1261-1277) that can be potentially harmful. While cyanobacteria are a prolific source of diverse natural products and toxins (Carmichael W. W. 1992. 72: 445-459; Gerwick et al. 2001. Alkaloids Chem. Biol. 57: 75-184; Namikoshi et al. 1996. Bioactive compounds produced by cyanobacteria. J. Ind. Microbiol. 17: 373-384), a toxic compound (or any natural product) has not been isolated from a *Trichodesmium* species despite some efforts (Hawser et al. 1991. *Toxicon* 29: 277-278].

BLAST searches in GenBank with the pat genes revealed homologs in *T. erythraeum* IMS101. This led to the investigation of a potential patellamide-like biosynthesis cluster as well as its product, a small cyclic peptide, dubbed trichamide in *T. erythraeum*.

Prenylation

Prenylated peptides can also be formed using the peptides disclosed herein. Prenylation can be useful for a variety of reasons. For example, it can be useful in the synthesis of peptide libraries with an unprecedented modification. This can be used in drug discovery, for example. Prenylation can also be useful in the synthesis of peptide libraries with other prenyl modifications, including farnesylation and geranylation. Such modifications are important in cell signaling, especially as related to cancers.

Prenylation provides a unique handle for chemical modification of peptides, either individually or in library format. For example, this modification is useful in fluorescent labeling of peptides, for surface labeling, or for addition of specific functional groups. In the case of fluorescent labeling, modified peptides are used to determine a drug's mechanism of action, to probe cellular events by microscopy, as reagents or components in fluorescent detection kits (for metals, drug interactions, etc.), or as clinical diagnostic agents. Surface labeled peptides can also find use as arrayed libraries for drug discovery. Surfaces are labeled via metathesis or by other well known reactions involving terminal olefins. For the addition of specific functional groups, terminal olefins provide a robust chemical platform. Examples of functionalization include fluorescent labeling, surface labeling, addition of hydrophobic or hydrophilic groups, addition of drugs or other small molecules, addition of specific functional groups to increase drug interactions via avidity effects, and many others which are known to those of skill in the art and herein contemplated.

Prenylation was an ancestral function, and the enzymes gradually evolved to catalyze the other function (heterocyclization). Prenylation is a new type of posttranslational modification, and the regioselectivity of prenylation is a useful aspect. Posttranslational modifications include phosphorylation, acetylation, glycosidation, and other extremely important events in cell biology.

Evolution of Biosynthetic Pathways

Biosynthetic pathways to bacterial secondary metabolites are extremely complex, and an understanding of their evolution allows for the engineering of new pharmaceuticals. Symbiotic bacteria offer an ideal model to follow this evolution because relationships can be precisely defined. The evolution of the pat pathway was examined, from *Prochloron* spp. cyanobacterial symbionts of ascidians collected in the tropical Pacific. Six variants of the 70-amino acid patellamide precursor protein, PatE, were discovered from tropical Pacific *Prochloron* samples. In all cases, amino acid and DNA sequences were virtually identical except in the 16-amino acid regions encoding the actual patellamides, which had highly diverse DNA and amino acid sequences. By contrast, *Prochloron* spp. were found to be >99% identical by molecular methods. Thus, the coding sequences for patellamide biosynthesis have rapidly diversified by recombination that is unprecedented in bacterial metabolic pathways.

Bacteria living symbiotically with higher organisms provide a potential mechanism to more readily discern important events in the evolution of complex secondary metabolites. Often, bacteria-host relationships can be rigorously defined because of vertical transmission of symbionts, (Baumann, P. Annu. Rev. Microbiol. 59, 155-1589 (2005)) simplifying evolutionary scenarios. In addition, the common relationship of microscopic organisms with macroscopic, chemically defined animals or plants provides a platform for the study of pathway evolution.

*Prochloron* spp. are common symbiotic cyanobacteria that are intimately associated with marine animals, especially ascidians of the Family Didemnidae (Withers et al. Phycologia 17, 167-171 (1978); Lewin et al. *Prochloron*: A Microbial Enigma (Chapman and Hall, New York, 1989)). They are also found associated with stromatolites (bacterial mat structures), but they have not yet been found outside of these structured, metabolically active environments. Numerous cyclic peptides, especially those of the patellamide class, have been isolated from didemnid ascidians, forming overlapping families of evolutionarily related metabolites. (Sings et al. Journal of Industrial Microbiology & Biotechnology 17, 385-396 (1996); Schmidt et al. J. Nat. Prod. 67, 1341-1345 (2004)). The first gene cluster, pat, is described herein. pat is responsible for patellamide biosynthesis, demonstrating that *Prochloron* symbiotic bacteria are responsible for patellamide production (FIG. 10).

The pat cluster is composed of seven coding sequences, patA-G, five of which are essential for patellamide biosynthesis. The patellamides are produced by a microcin-like pathway, in which a precursor peptide PatE directly encodes the amino acid sequences of the patellamide products. PatE is modified by heterocyclization of Cys, Ser, and Thr residues, followed by N—C terminal cyclization to afford the final patellamides. It was proposed that start/stop recognition sequences are responsible for the modification to the PatE precursor peptide, while the actual coding sequences between the start/stop have little or no effect on modification.

A large family of patellamides and related compounds have been isolated from didemnid ascidians, leading to the proposal that the pat pathway has rapidly diversified to produce a natural combinatorial library of cyclic peptides. To test this idea, 46 *Prochloron*-containing ascidians were collected in Palau and Papua New Guinea in the tropical Pacific. Ascidians species included *Lissoclinum* spp., *L. patella, Didemnum* spp., *D. molle*, and others. DNA and cyclic peptides were readily purified from these organisms and analyzed by PCR/sequencing, mass spectrometry, and $^1$H NMR.

patE PCR primers were applied to *Prochloron* DNA samples, and the products were directly sequenced. Overlapping sequences were deconvoluted, leading to the discovery of six pate variants (E1-E6), encoding a total of 9 different patellamide-like products. The existence of these putative variants was confirmed by PCR with specific primers for the variants. While most encoded known compounds, some encoded potentially new structures. These patE variants were virtually identical to each other, except that the nucleotide sequence encoding amino acids forming the patellamides were highly mutated, exhibiting identities down to 46%. Some pate variants encoded eight amino-acid products, while others encoded seven amino-acid compounds. The variability in DNA led to highly varied predicted peptide products, although trends could be readily observed. All patE variants encode two patellamide-like molecules, and the recognition sequence regions flanking the coding regions are highly conserved at the DNA and protein levels. This indicates that the second recognition/coding region in patE arose via a duplication.

Both ribosomal RNA and primary metabolic genes were examined to determine whether there was a similar high level of mutation across the *Prochloron* genomes. All 16S rDNA clones sequenced were virtually identical. Unlike the majority of cyanobacteria, *Prochloron* spp. contain chlorophyll b as well as chlorophyll a. Chlorophyll a oxidase (cao) is thus a relatively specific primary metabolic gene that can be used to identify *Prochloron*. cao was amplified from a series of samples with different pate sequences, and it was highly conserved at the DNA sequence level. cao was >99% identical in all strains tested except for two, which exhibited 98% and 97% identity. The presence of patE1-E6 did not correlate with either host or symbiont taxonomy, implicating horizontal transfer as the source of variability.

Specific primers were designed for patE1-E6, and primers from different locations in the known pat were used to determine the presence of whole pathways. Intact pathways contained continuous sequence between patD-patE and patE-patF, while some variants appeared to be non-contiguous with other pat genes. In these cases of isolation, no patellamide-like products could be detected as major compounds in extracts, showing that intact pat pathways are required to produce these compounds. Sequence analysis of numerous patA-G pathway genes, including those clustered with new patE variants, showed that these genes were essentially identical (>99% identical) with each other.

Often, one, two, or three different patE variants were discovered in the same sample. There are two possible explanations: either there are multiple sequences in single strains, or there are multiple strains in the same ascidian. The difference is highly pertinent to the mode of pathway evolution, since pilin genes in bacteria evolve by recombination from up to six copies in a single genome. Two genes, patE1 and patE2, were present in a sample from Palau that was the subject of genome sequence analysis. In this sample, the sequencing reads for the two genes were present in a 1:2 ratio. This ratio was also reinforced by quantitative PCR analysis, which gave the same 1:2 patE1:patE2 ratio.

Quantitative PCR analysis was applied to several other samples from Papua New Guinea. By PCR analysis, Papua New Guinea *L. patella* samples 05-019 from the Milne Bay region and 03-005 from Madang contained patE1, patE2, and patE3. Q-PCR showed that these genes were present in a 1:15:70 ratio in sample 05-019 and in a 1:4.5:9 ratio in 03-005. In summary, samples from three different locations showed three different ratios of patE genes, indicating that multiple strains are indeed present in the same organism. Thus, the recombination event leading to PatE variants does not follow the pilin-like mechanism.

As mentioned above, intact pat pathways were required for patellamide-like products to be synthesized. patE3 contained sequences encoding lissoclinamides, compounds composed of seven amino acids for which no biosynthetic machinery had been previously described. An ascidian, *Lissoclinum patella* from Papua New Guinea, contained patE3 and was selected for detailed chemical analysis. From this sample, lissoclinamides 2-4 and the related ulicyclamide were purified to homogeneity and characterized by $^1$H NMR and mass spectrometry. Lissoclinamides 2 and 4 are directly encoded by patE3. Ulicyclamide and lissoclinamed 3 are encoded by the same sequence as for lissoclinamide 2, but they differ in their posttranslational modifications. Ulicyclamide, for example, contains two thiazoles, while the others contain one thiazole and one thiazoline. The molecules also differ in their stereochemistry adjacent to thiazole/thiazoline, although this process may be spontaneous. Samples containing other patE variants, such as those encoding patellamide C and ulithiacyclamide, also were shown to contain their predicted chemical products. Samples from which patE variants could not be amplified did not contain related products at a detectable level.

Thus, it has been shown that evolution of quite different patellamide like products has only required a switch in small cassettes encoding 7-8 amino acids, while the remainder of the pathways were intact. Examination of 16S and selected ITS regions indicated that these *Prochloron* strains from numerous animals of different species were quite closely related (>99% ITS identity). Thus, within very closely related *Prochloron* strains, the patellamide pathway has diverged by rapid recombination. The observation of natural variation in pat have allowed for the specific, testable predictions regarding the engineering of the pathway to make new compounds. An entire patellamide-coding region was mutated to a wholly unnatural pathway and a new, cyclic peptide was obtained (described below). These results reinforce the power of studying symbiosis to understand evolution and engineering in natural products pathways.

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular patellamide is disclosed and discussed and a number of modifications that can be made to a number of molecules of the patellamide are discussed, specifically contemplated is each and every combination and permutation of those and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein are sets of recombinant proteins that catalyze the N—C terminal cyclization of peptides via amide bonds. This cyclization event does not depend upon the sequence of the cyclized peptide; rather, recognition sequences in a prepeptide surrounding the peptide of interest dictate the cyclization. Disclosed herein are various prepeptides (also referred to as recognition sequences). While the polymer, such as a peptide, to be cyclized (also referred to as the coding sequence) can vary greatly and still be cyclized, and can, in fact, be any peptide capable of being cyclized, the recognition sequence is much more specific.

As discussed above, any type of polymer, including peptides, can be cyclized using the recognition sequences disclosed herein, including organic polymers such as biopolymers that contain amino acid or nucleotide monomers, or a mixture of different types of monomers. Accordingly, polypeptides, polynucleotides, or a polymer containing both amino acid and nucleotide monomers, for example, may be cyclized using the subject methods. In many embodiments of the invention, the polymer used is a biopolymer containing amino acids, i.e., a polypeptide. Polymers that may be employed herein may not contain any peptide bonds. However, in certain embodiments, the polymers may contain peptide bonds in between the first and second monomers of one or both ends of the polymer to be cyclized.

For example, below, the sequences in bold are the recognition sequences, and the intervening underlined sequences are cyclized by the described enzymes. The combination of coding sequence and recognition sequence is referred to throughout the application as a "fusion polypeptide." For example, this sequence was modified this sequence to the completely unnatural variant PatE:

(SEQ ID NO: 45)
MNKKNILPQQGQPVIRTAGQLSSQLAELSEEALGDAGLEASVTACITFCA

YDGVEPSITVCISVCAYDGE

The sequences in bold are the recognition sequences, and the intervening underlined sequences are cyclized by the described enzymes. This sequence was modified this sequence to the completely unnatural variant PatEBS:

(SEQ ID NO: 46)
MNKKNILPQQGQPVIRTAGQLSSQLAELSEEALGDAGLEASVTACITFCA

YDGVEPSQGGRGDWPAYDGE where the second underlined sequence has been changed. This compound was isolated from *E. coli* broth cultures. This modification proves that the enzymes only rely on the bold recognition sequences, not on the underlined "coding sequences". Further evidence in favor of this is that the peptide PatEBS2 was synthesized:

(SEQ ID NO: 47)
MNKKNILPQQGQPVIRTAGQLSSQLAELSEEALGDAGLEASVTACITFCA

YDGVEQSQGGRGDWPAYDGE where the middle bold sequence, AYDGVEPS, has been mutated to AYDGVEQS. With a modification in the recognition sequence, cyclic peptides were no longer produced.

The advantage of amide-cyclized peptides is two-fold. First, conformational freedom is greatly restricted, leading to much better binding constants (more potent drugs or biomolecules). Second, amide-cyclized peptides have favorable pharmacological properties, such as resistance to proteases and advantages in delivery.

This cyclization may take place either in vitro with purified enzymes or in *Escherichia coli* expression constructs, or in other vectors and systems as described herein. The cyclization can also take place in in vivo systems, as described below.

Disclosed herein are isolated peptides that can act as "recognition sequences", and function as prepeptides to allow for the formation of cyclized peptides. For example, disclosed herein is an isolated peptide comprising an amino acid segment comprising the amino acid sequence of SEQ ID NO: 1 (GLEASN$^1$AYDGVEPSN$^2$AYDGE) where N is the coding sequence and can be any length, as discussed above. For example, the coding sequence can be 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 amino acids in length, or any amount in between, for example. There are numerous examples given throughout of various peptides that can be cyclized by the recognition sequences disclosed herein.

The isolated peptide can also comprise an amino acid segment comprising the amino acid sequence of SEQ ID NO: 2 (GLEASN$^1$AYDGVEPS, where N is the coding sequence and can be any length). Also disclosed is an isolated peptide comprising an amino acid segment comprising the amino acid sequence of SEQ ID NO: 3 (AYDGVEPSN$^2$AYDGE where N is the coding sequence and can be any length).

As discussed in greater detail below, the isolated peptide can comprise an amino acid sequence at least about 90% identical to the amino acid sequence of SEQ ID NO: 1, or the amino acid sequence of SEQ ID NO: 1 can have one or more conservative amino acid substitutions. For example, recognition sequences are more highly conserved, but can contain modifications such as LEAS/VEPS/PGPS in the first position of patE1, patE2, and triG, respectively.

Examples of recognition sequences can be found in SEQ ID NO: 4 (GLEASVTACITFCAYDGVEPSCTLCCTL-CAYDGE), which encodes both Patellamide C and ulithia-cyclamide, and in SEQ ID NO: 5 (GLEASVTACITF-CAYDGVEPSQGGRGDWPAYDGE), which encodes Patellamide C and eptidemnamide.

A further example can be found in SEQ ID NO: 6 (GLEAS-VTACITFCAYDGVEPSITVCISVCAYDGE), which encodes Patellamide A and Patellamide C.

As discussed above, recognition sequences can also be found in the *Trichodesmium* species. For example, disclosed is SEQ ID NO: 7 (MGKKNIQPNSSQPVFRSLVARPA-LEELREENLTEGNQGHGPLANGPGPSGDGL HPRLCSCSYDGDDE), which encodes the cyclic peptide trichamide. This sequence can be further shortened and still produce trichamide, for example, using SEQ ID NO: 8 (GPGPSGDGLHPRLCSCSYDGDDE).

Also disclosed is the amino acid sequence of SEQ ID NO: 9 (GPGPSNSYDGDDE), wherein N can be any length, and the remaining sequence is a recognition sequence which allows for the cyclization of whichever peptide is placed in the "N" position Also disclosed herein is an isolated peptide comprising an amino acid segment comprising the amino acid sequence of SEQ ID NO: 50 (GVDASN$^1$SYDGVDASN$^2$SYDD) where N is the coding sequence and can be any length, as discussed above. For example, the coding sequence can be 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 amino acids in length, or any amount in between, for example. There are numerous examples given throughout of various peptides that can be cyclized by the recognition sequences disclosed herein.

The isolated peptide can also comprise an amino acid segment comprising the amino acid sequence of SEQ ID NO: 52 (GVDASN$^1$SYDGVDAS, where N is the coding sequence and can be any length). Also disclosed is an isolated peptide comprising an amino acid segment comprising the amino acid sequence of SEQ ID NO: 53 (SYDGVDASN$^2$SYDD where N is the coding sequence and can be any length).

Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithmns. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. Methods Enzymol 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Nucleic Acids

There are a variety of molecules disclosed herein that are nucleic acid based, including for example the nucleic acids that encode, for example, patellatnides and trichamide as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups ($NH_2$ or 0) at the C6 position of purine nucleotides.

b) Sequences

There are a variety of sequences related to, for example, patellamides and trichamides as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. The cyclic peptides disclosed herein can be encoded by functional nucleic acids, and indeed can be expressed in vivo. These functional nucleic acids encoding cyclic peptides and the necessary recognition sequences to cyclize them can have a wide variety of applications, as discussed elsewhere herein.

Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with kds from the target molecule of less than $10^{-12}$ M. It is preferred that the aptamers bind the target molecule with a $k_d$ less than $10^{-6}$, $10^{-8}$, $10^{-10}$ or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular, reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616, 466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650, 316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci.* USA 89:8006-8010 (1992); WO 93/22434 by Yale; WO 95/24489 by Yale; Yuan and Altman, *EMBO J.* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

Vectors and Fusion Polypeptides

Disclosed herein are vectors comprising a nucleotide sequence encoding a fusion polypeptide. These vectors can be used to produce a cyclized peptide of interest, are useful with libraries and combinatorial chemistry techniques (discussed below), and are useful with in vivo systems.

For example, disclosed herein is a vector comprising, from N-terminus to C-terminus: a) a C-terminal domain comprising SEQ ID NO: 10 (GLEAS); b) a peptide; c) an N-terminal domain comprising SEQ ID NO: 11 (AYDGVEPS); wherein the fusion polypeptide is able to cyclize the peptide to produce a cyclic peptide in a mammalian cell.

Also disclosed is a vector comprising a nucleotide sequence encoding a fusion polypeptide comprising, from N-terminus to C-terminus: a) a C-terminal domain comprising SEQ ID NO: 11 (AYDGVEPS); b) a peptide; c) an N-terminal domain comprising SEQ ID NO: 12 (AYDGE); wherein the fusion polypeptide is able to cyclize the peptide to produce a cyclic peptide in a cell. This cell can be prokaryotic, such as *E. coli*, or eukaryotic, such as a mammalian cell.

Also disclosed herein is a vector comprising a nucleotide sequence encoding a fusion polypeptide comprising, from N-terminus to C-terminus: a) a C-terminal domain comprising SEQ ID NO: 10 (GLEAS); b) a peptide; c) an N-terminal domain comprising SEQ ID NO: 12 (AYDGE); wherein the fusion polypeptide is able to cyclize the peptide to produce a cyclic peptide in a cell. This cell can be prokaryotic, such as *E. coli*, or eukaryotic, such as a mammalian cell.

Also disclosed herein is a vector comprising a nucleotide sequence encoding a fusion polypeptide comprising, from N-terminus to C-terminus: a) a C-terminal domain comprising SEQ ID NO: 13 (GPGPS); b) a peptide; c) an N-terminal domain comprising SEQ ID NO: 14 (SYDGDDE); wherein the fusion polypeptide is able to cyclize the peptide to produce a cyclic peptide in a cell. This cell can be prokaryotic, such as *E. coli*, or eukaryotic, such as a mammalian cell.

The vectors disclosed above can comprise a random peptide, which are discussed in greater detail below. The peptide of interest (the coding sequence) can be derived from a cDNA library. For example, each vector in the library can encode a different fusion polypeptide. In a further example, the peptide of interest of each different fusion polypeptide can be different. The peptide of interest can be a random peptide at least 3 amino acids in length, as discussed below.

Also disclosed is a cell comprising the vectors discussed above, or progeny thereof. This cell can be prokaryotic, or eukaryotic, such as a mammalian cell. Examples of such cells include a tumor cell, a liver cell, a hepatocyte, a mast cell and a lymphocyte cell. The cell can also be a human cell.

There are a number of compositions and methods which can be used to deliver nucleic acids, such as those encoding the cyclic peptides disclosed herein, to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as those encoding cyclic peptides, into the cell without degradation and include a promoter yielding expression of the gene in the cells into which it is delivered. In some embodiments the peptides are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRX Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell. Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell. Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fingi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin Peptides a) Protein Variants As discussed herein, the coding sequence of the peptides disclosed herein can vary widely and still be cyclized. Furthermore, the recognition sequences, which must have more specificity but which can still have some degree of variance and remain functional, are also disclosed herein. For example, there are numerous variants of the coding sequences that are known and herein contemplated. In addition, to the known functional strain variants there are derivatives of the these proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala (A) |
| allosoleucine | AIle |
| arginine | Arg (R) |
| asparagine | Asn (N) |
| aspartic acid | Asp (D) |
| cysteine | Cys (C) |
| glutamic acid | Glu (E) |

TABLE 1-continued

Amino Acid Abbreviations

| Amino Acid | Abbreviations |
|---|---|
| glutamine | Gln (K) |
| glycine | Gly (G) |
| histidine | His (H) |
| isolelucine | Ile (I) |
| leucine | Leu (L) |
| lysine | Lys (K) |
| phenylalanine | Phe (F) |
| proline | Pro (P) |
| pyroglutamic acid | PGlu |
| serine | Ser (S} |
| threonine | Thr (T) |
| tyrosine | Tyr (Y) |
| tryptophan | Trp (W) |
| valine | Val (V_ |

TABLE 2

Amino Acid Substitutions
Original Residue Exemplary Conservative Substitutions, others are known in the art.

Ala; ser
Arg; lys, gln
Asn; gln; his
Asp; glu
Cys; ser
Gln; asn, lys
Glu; asp
Gly; pro
His; asn; gln
Ile; leu; val
Leu; ile; val
Lys; arg; gln
Met; leu; ile
Phe; met; leu; tyr
Ser; thr
Thr; ser
Trp; tyr
Tyr; trp; phe
Val; ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences.

Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is understood that while no amino acid sequence indicates what particular DNA sequence encodes that protein within an organism, where particular variants of a disclosed protein are disclosed herein, the known nucleic acid sequence that encodes that protein in the particular sequence from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $-CH_2NH-$, $-CH_2S-$, $-CH_2-CH_2-$, $-CH=CH-$ (cis and trans), $-COCH_2-$, $-CH(OH)CH_2-$, and $-CHH_2SO-$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($-CH_2NH-$, $CH_2CH_2-$); Spatola et al. Life Sci 38:1243-1249 (1986) ($-CH H_2-S$); Hann J. Chem. Soc Perkin Trans. I 307-314 (1982) ($-CH-CH-$, cis and trans); Almquist et al. J. Med. Chem. 23:1392-1398 (1980) ($-COCH_2-$); Jennings-White et al. Tetrahedron Lett 23:2533 (1982) ($-COCH_2-$); Szelke et al. European Appln, EP 45665 CA (1982): 97:39405 (1982) ($-CH(OH)CH_2-$); Holladay et al. Tetrahedron. Lett 24:4401-4404 (1983) ($-C(OH)CH_2-$); and Hruby Life Sci 31:189-199 (1982) ($-CH_2-S-$); each of which is incorporated herein by reference. A particularly preferred non-peptide linkage is $-CH_2NH-$. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with the cyclized peptide. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies (and fragments thereof) can also be produced using phage display libraries (Hoogenboom et al., *J. Mol. Biol.*, 227:381, 1991; Marks et al., *J. Mol. Biol.*, 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature*, 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature*, 321:522-525 (1986), Riechmann et al., *Nature*, 332:323-327 (1988), Verhoeyen et al., *Science*, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly neutralizing antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

The disclosed compositions and methods can also be used for example as tools to isolate and test new drug candidates for a variety of diseases.

Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

Compositions Identified by Screening with Disclosed Compositions/Combinatorial Chemistry a) Combinatorial Chemistry/Libraries The fusion polypeptides of the invention can comprise random peptides. By "random peptides" herein is meant that each peptide consists of essentially random amino acids. Since generally these random peptides (or nucleic acids, discussed below) are chemically synthesized, they may incorporate any amino acid at any position. The synthetic process can be designed to generate randomized proteins to allow the formation of all or most of the possible combinations over the length of the sequence, thus forming a library of randomized peptides.

This invention provides libraries of fusion polypeptides. By "library" herein is meant a sufficiently structurally diverse population of randomized expression products to effect a probabilistically sufficient range of cellular responses to provide one or more cells exhibiting a desired response. Accordingly, an interaction library must be large enough so that at least one of its members will have a structure that gives it affinity for some molecule, protein, or other factor whose activity is of interest. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$-$10^8$ is sufficient to find structures with affinity for the target. A library of all combinations of a peptide 7 to 20 amino acids in length, such as proposed here for expression in retroviruses, has the potential to code for 20$^7$ ($10^9$) to 20$^{20}$. Thus, with libraries of $10^7$-$10^8$ per ml of retroviral particles the present methods allow a "working" subset of a theoretically complete interaction library for 7 amino acids, and a subset of shapes for the 20$^{20}$ library. Thus, in a preferred embodiment, at least $10^6$, preferably at least $10^7$, more preferably at least $10^8$ and most preferably at least $10^9$ different expression products are simultaneously analyzed in the subject methods. Preferred methods maximize library size and diversity.

In a preferred embodiment, libraries of all combinations of a peptide 3 to 30 amino acids in length are synthesized and analyzed as outlined herein. Libraries of smaller cyclic peptides, i.e., 3 to 4 amino acid in length, are advantageous because they are more constrained and thus there is a better chance that these libraries possess desirable pharmacokinetics properties as a consequence of their smaller size. Accordingly, the libraries of the present invention may be one of any of the following lengths: 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, 26 amino acids, 27 amino acids, 28 amino acids, 29 amino acids and 30 amino acids in length.

The invention further provides fusion nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way which does not change the amino acid sequence of the fusion protein.

Using the nucleic acids of the present invention which encode a fusion protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the fusion protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, to polyadenylation signals, and enhancers.

The fusion nucleic acids are introduced into cells to screen for cyclic peptides capable of altering the phenotype of a cell. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include liposome fusion, lipofectin®, electroporation, viral infection, etc. The fusion nucleic acids may stably integrate into the genome of the host cell, or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

The fusion nucleic acids can be part of a retroviral particle which infects the cells, as described above. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

The fusion nucleic acids can be introduced into cells using retroviral vectors. This is described in more detail above, however, is reviewed briefly again. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153-159 (1993), hereby incorporated by reference). Such helper-defective packaging lines are capable of producing all the necessary trans proteins-gag, pol, and env- that are required for packaging, processing, reverse transcription, and integration of recombinant genomes. Those RNA molecules that have in cis the psi packaging signal are packaged into maturing virions. Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al, supra: Pear et al., PNAS USA 90(18): 8392-6 (1993); Kitamura et al., PNAS USA 92:9146-9150 (1995); Kinsella et al., Human Gene Therapy 7:1405-1413; Hofmann et al., PNAS USA 93:5185-5190; Choate et al., Human Gene Therapy 7:2247 (1996); and WO 94/19478; and references cited therein, all of which are incorporated by reference.

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed in SEQ ID NOS: 1-13 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function.

It is understood that the disclosed methods for identifying molecules can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example an extracellular portion, is attached to a DNA binding domain of a transcriptional activation protein, such as Gal 4. By performing the Two-hybrid technique on this type of system, molecules that bind the extracellular portion can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions are also disclosed. Thus, the products produced using the molecular modeling approaches that involve the disclosed compositions, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Ouantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario.

Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

Kits

Disclosed herein are kits that are drawn to reagents that can be used in practicing the methods disclosed herein. For example, the kits can comprise reagents for generating libraries of cyclic peptides. The kits can include any reagent or combination of reagent discussed herein or that would be understood to be required or beneficial in the practice of the disclosed methods. For example, the kits could include the recognition sequences, such as those found in SEQ ID NOS: 1-13, as well as the buffers and enzymes required to use the sequences as intended.

Compositions with Similar Functions

It is understood that the compositions disclosed herein have certain functions, such as cyclizing peptides. Disclosed herein are certain structural requirements for performing the disclosed functions, and it is understood that there are a variety of structures which can perform the same function which are related to the disclosed structures, and that these structures will ultimately achieve the same result, for example cyclization. These compositions are also contemplated herein.

D. Methods of Making the Compositions

The compositions disclosed herein and the compositions necessary to perform the disclosed methods can be made using any method known to those of skill in the art for that particular reagent or compound unless otherwise specifically noted.

Nucleic Acid Synthesis

For example, the nucleic acids, such as, the oligonucleotides to be used in vectors can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

Peptide Synthesis

One method of producing the disclosed peptides, such as SEQ ID NO: 1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Process Claims for Making the Compositions

Disclosed are processes for making the compositions as well as making the intermediates leading to the compositions. For example, disclosed are nucleic acids in SEQ ID NOs: 1-13. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth herein and a sequence controlling the expression of the nucleic acid.

Also disclosed are nucleic acid molecules produced by the process comprising linking in an operative way a nucleic acid molecule comprising a sequence having 80% identity to the given sequence, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth herein and a sequence controlling the expression of the nucleic acid.

Disclosed are nucleic acid molecules produced by the process comprising linking in an operative way a nucleic acid molecule comprising a sequence encoding a peptide set forth herein and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

E. Methods of Using the Compositions

Methods of Using the Compositions as Research Tools

The disclosed compositions can be used in a variety of ways as research tools. For example, the disclosed polypeptide sequences can be used to identify compositions useful as pharmaceuticals.

For example, disclosed herein are methods for cyclizing a polypeptide comprising inserting the polypeptide to be cyclized in the coding region of a fusion polypeptide. For example, SEQ ID NO: 1, GLEASN$^1$AYDGVEPSN$^2$AYDGE, shows two "N" regions, "N$^1$" and "N$^2$". Into either, or both, of these regions can be inserted a coding sequence, such as a sequence encoding a peptide to by cyclized. The entire sequence is known as a fusion polypeptide.

Another example comprises a method for cyclizing a polypeptide, the polypeptide to be cyclized is inserted into the "N" position of SEQ ID NO: 2. The same principal applies to SEQ ID NOS: 3 and 9 as well.

Although the coding region is often referred to herein as a peptide, it can be any polymer capable of being cyclized. It is known in the art that any type of polymer can be cyclized using the methods disclosed herein, including organic polymers such as biopolymers that contain amino acid or nucleotide monomers, or a mixture of different types of monomers. Accordingly, polypeptides, polynucleotides, or a polymer containing both amino acid and nucleotide monomers, for example, may be cyclized using the subject methods. In many embodiments of the invention, the polymer used is a biopolymer containing amino acids, i.e., a polypeptide. Polymers that may be employed in the subject methods may not contain any peptide bonds. However, in certain embodiments, the polymers may contain peptide bonds in between the first and second monomers of one or both ends of the polymer to be cyclized.

A polymer of interest may be at least 2, 3, 4, 5, 6, 7, 8, 9, 10, 11 or 12 monomers, or more than 12 monomers in length, usually up to about 20, 30, 40, 50 or 100 or 1000 or more monomers in length. Accordingly, a peptide employed in the subject methods may contain at least 2, 3, 4, 5, 6, 7, 8, 9, 10, 11 or 12 amino acids, or more than 12 amino acids, usually up to about 20, 30, 40 or 50 amino acids (e.g., non-naturally occurring amino acids, naturally occurring amino acids or a mixture thereof. Polymers of particular interest are 2-50, 3-40, 4-30, 3-8, 5-20 or 6-10 monomers in length, and typically range from 500-5000 Da, 600-4000 Da, 700-2000 Da in molecular weight.

The compositions can be used for example as targets in combinatorial chemistry protocols or other screening protocols to isolate molecules that possess desired functional properties, as discussed above.

The disclosed compositions can also be used diagnostic tools related to diseases. The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

Method of Treating Cancer

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

A Minimal Gene Set for In Vivo Production of Cyclic Peptide Libraries a) Bacterial Strains, Plasmids, Materials and Instrumentation Chemically competent TOP10, DH5α and BL21(DE3) *E. coli* were available from Invitrogen. DUET vectors pCDF, pRSF, pET, and pACYC were purchased from Novagen. Restriction endonucleases were obtained from NEB. DNA ligase was from Takara. Synthetic oligonucleotides were obtained from the DNA/Peptide Core Facility at the University of Utah and used without additional purification. PCR was performed using PlatinumTaq HiFi DNA polymerase from Invitrogen. Isolation of plasmid DNA was by the QIAprep Spin Miniprep Kit Protocol from Qiagen. Extraction of plasmid DNA from agarose gels was done using the QIAquick Gel Extraction Kit, also available from Qiagen.

b) Preparation of Pat A-G Overexpression Constructs a. Source DNA. A Palau reef sample of the ascidian, *Lissoclinum patella*, was used to amplify the whole pat cluster, as previously described. pat was cloned into the pCR2.1-TOPO vector (Invitrogen) to create TOPO-pat (Schmidt, E. W.; Nelson, J. T.; Rasko, D. A.; Sudek, S.; Eisen, J. A.; Haygood, M. G.; Ravel, J. *Proc. Nat. Acad. Sci. USA* 2005, 102, 7315-7320).

Cloning of genes. The following general strategy was used. PCR primers were designed to contain BspHI/NotI or BspHI/EagI restriction sites for ligation into the DUET vector NcoI/NotI sites (Table 3). For cloning into the second DUET multiple cloning site, KpnI/NdeI sites were included in primers. PCR products were obtained from TOPO-pat using standard conditions, then ligated directly into pCR2.1-TOPO vector and transformed into TOP10 *E. coli* cells according to the manufacturer's protocol. These cells were grown in LB media with ampicillin (50 µg/mL). Products were subsequently subcloned into DUET vectors using suitable restriction endonucleases and transformed into DH5α. All cloned products were completely sequenced to verify the integrity of inserts.

TABLE 3

| Gene | Insert Size (kb) | Forward Primer | Destination Vector | Rest. Site |
|---|---|---|---|---|
| Pat A | 2.1 | ATCATGAATAGAGATATTTTGCGAAC (SEQ ID NO: 21) | pACYC-Duet | BspHI |
| Pat B | 0.2 | GAATCATGAGACTTCCGCTACTGTC (SEQ ID NO: 22) | pET-Duet | BspHI |
| Pat C | 0.2 | AAACATATGATGGTCACTAACAACCC (SEQ ID NO: 23) | pACYC-Duet | NdeI |
| Pat D | 2.4 | TTCATGAACCCAACCGCGCTCCAAATTAAG (SEQ ID NO: 24) | pCDF-Duet | BspHI |
| Pat E | 0.2 | CCAACCAACATATGAACAAGAAGAACATTCTACCCC (SEQ ID NO: 25) | pRSF-Duet | NdeI |
| Pat F | 1 | AACATATGGACTTAAATTGACAGGCTTC (SEQ ID NO: 26) | pET-Duet | NdeI |
| Pat G | 3.6 | CCATATGATCACGATAGACTACCCTTTC (SEQ ID NO: 27) | pCDF-Duet | NdeI |

| Gene | Reverse Primer | Rest. Site |
|---|---|---|
| Pat A | TCGGCCGTTCCTTAGTAAGAAGAAGACCAAG (SEQ ID NO: 28) | EagI |
| Pat B | AAATGCGGCCGCTTAATCAGAATAAGCGTCCCATAC (SEQ ID NO: 29) | NotI |
| Pat C | AAAGGTACCGAAAGAAGTAGCCTTAGAGTTAAG (SEQ ID NO: 30) | KpnI |
| Pat D | GCCGCGGCCGCAAACTTGAAAATGCTTAAAACG (SEQ ID NO: 31) | NotI |
| Pat E | TTCTTATTGGTACCCTTATTCACCATC (SEQ ID NO: 32) | KpnI |
| Pat F | ATGACTAGGTACCTGAGTCAATGCAAATG (SEQ ID NO: 33) | KpnI |

TABLE 3-continued

| Pat G | CGGTACCCCAATAACTACTTTGAGACGGTG (SEQ ID NO: 34) | KpnI | c) Expression and Purification of Secondary Metabolites

Expression plasmids were transformed into E. coli BL21 (DE3) and grown in minimal auto-inducing media using the method of Studier (Studier, F. W. Protein Expr. Purif. 2005, 41, 207-34). Antibiotics were present at the following concentrations for the corresponding plasmids: pACYC-DUET, chloramphenicol, 12.5 µg/mL; pCDF-DUET, streptomycin, 50 µg/mL; pRSF-DUET, kanamycin, 30 µg/mL; pET-DUET, ampicillin, 50 µg/mL. After 18 hours, cultures were harvested by centrifugation for 20 min at 5,000 g.

Purification of recombinant cyclic peptides was achieved essentially as described above, Briefly, HP20SS (~10 g) resin was added to each 50 mL of culture supernatant and shaken vigorously for 1 h. The resin was filtered to remove media and then washed with 25% methanol in water (100 mL). Crude compound fractions were eluted by sequential washes of methanol (2×50 mL) and acetone (2×50 mL). The organic fractions were concentrated by rotary evaporation and re-suspended in a minimal volume of ethyl acetate. The organic fraction was washed with ddH$_2$O (3×10 mL). The organic layer was then concentrated once again and the resulting crude extract subjected to analysis.

d) Analysis of Secondary Metabolite Production by HPLC-MS and NMR

HPLC-electrospray ionization-MS analysis was performed on a ThermoFinnigan LCQ Classic ion-trap mass spectrometer. For HPLC, an analytical C18 column (Gemini, Phenomenex) was used with a methanol-water gradient. An initial 50:50 mixture of methanol and water (each containing 0.1% formic acid) was subjected to a gradient to 95% methanol over 15 minutes, followed by 10 minutes at 95% methanol. Electrospray ionization MS was performed in the positive mode. For positive controls, authentic standards of ulithiacyclamide were injected or co-injected on the HPLC-ESI-MS instrument. Negative controls consisted either of blank runs or runs from fermentations lacking the patE gene.

e) Synthesis of PatEdm

A cloning strategy was designed in which all eight amino acids were simultaneously swapped for new amino acids, while the "recognition" sequences flanking the patellamide coding sequences were maintained intact. pRSF-patE was used as a template for the QuickChange Multi Site-Directed Mutagenesis kit (Stratagene) following the manufacturer's protocols. The following primers were used to affect mutation: EBSBf:

(SEQ ID NO: 15)
5'GCATCACTTTTTGCGCTTATGATGGTGTGGAGCCATCTGAGGGCGGAC

GCGGTGACTGGCCTGCTTACGATGGTGAATAA;

EBSBr:

(SEQ ID NO: 16)
5'TTATTCACCATCGTAAGCAGGCCAGTCACCGCGTCCGCCCTGAGATGG

CTCCACACCATCATAAGCGCAAAAAGTGATGC.

Clones were sequenced to find plasmids containing intact patEdm with no mutations. In addition, a mutant, designated patEdm*, was found in which a key recognition sequence amino acid, P$^{56}$, was mutated to Q. pRSF-patEdm and pRSF-patEdm* were cloned into a strain of E. coli BL21(DE3) containing the minimal cyclization gene set (pACYC-patA, pCDF-patD-patG, and pET-patB-patF). This strain was cultivated and extracted as described above.

2. Example 2

Trichamide, a Cyclic Peptide from the Bloom-Forming Cyanobacterium Trichodesmium erythraeum Predicted from the Genome Sequence a) Materials and Methods (1) Bioinformatics Most of the T. erythraeum IMS101 genome was shotgun sequenced by the Joint Genome Institute (JGI) and is available in GenBank (www.ncbi.nlm.nih.gov). The contig with accession number NZ_AABKO4000003 contains the pat homologs listed before. Nucleotides 785,500 to 803,500 of this contig were downloaded and manually annotated in Artemis (Sanger Institute). Predicted ORFs were compared to the JGI auto-annotation and putative functions assigned by BLASTP on GenBank.

(2) Culturing

T. erythraeum IMS101 [Prufert-Bebout et al. 1993. Appl. Environ. Microbiol. 59: 1367-1375] was obtained. The culture is non-axenic, i.e. does contain other heterotrophic bacteria. Cultures were grown in R medium at 25° C. under 12 hour light-dark photocycle with slow stirring as well as daily inversion of the culture flasks. R medium: 25% ddH$_2$O and 75% natural sea water from Scripps pier are mixed and amended with 8 µM KH$_2$PO$_4$, 2.5 µM EDTA, 0.1 µM ferric citrate, 0.1 µM MnCl$_2$, 10 nM Na$_2$MoO$_4$, 10 nM ZnSO$_4$, 0.1 nM CoCl$_2$, 0.1 nM NiCl$_2$, and 0.1 nM Na$_2$SeO$_4$. All components are 0.2 µm filter-sterilized. T. erythraeum requires a 10% inoculum to start cultures; accordingly, 800 ml of culture were used in 8 liters of R medium. After 12-14 days, the culture was vacuum filtered through a 5 µm polycarbonate filter. T. erythraeum colonies remain on the filter, while most other bacteria do not. The cell material was rinsed off the filters into a 50 ml Falcon tube with ddH$_2$O, immediately frozen at −80° C. and later lyophilized. The average yield was ~10 mg dried cells per liter culture volume.

(3) Extraction and Purification

Lyophilized cyanobacterial pellets were extracted 3× with a ~100-fold excess of methanol. The methanolic extract was dried, yielding a crude extract that was used for initial electron spray ionization mass spectrometry (ESI-MS). For Fourier-transform MS (FT-MS), the crude extract was purified with a C$_{18}$ ZipTip (Millipore).

A portion of the crude methanolic extract (23 mg) was further purified by partitioning between ethyl acetate and water. The aqueous part was fractionated over a HP20SS column with 25, 50, 75 and 100% acetone. As determined by ESI-MS, the 25 and 50% acetone (aq.) fractions contained the 1099 peak and were combined. This combined fraction was run on a Phenomenex C$_{18}$ analytical column with the following protocol (all solvents contained 0.01% trifluoroacetic acid): 5 min of water, 5-35 min gradient from 0-100% acetonitrile, 10 min of 100% acetonitrile. Fractions were collected in minute intervals. Only fractions eluting at 16-17 and 17-18 minutes contained a 1099 peak as determined by ESI-MS. These fractions did not contain a single compound, since additional peaks beside 1099 were present in the MS. The amount of material in the two HPLC fractions was too low to measure.

In an improved procedure, a methanolic extract (57 mg) was partially purified by step gradient on a column containing 7 g $C_{18}$, using solvents containing 0.01% trifluoroacetic acid. Fractions were eluted with water, followed by 25%, 50% and 100% acetonitrile (aq). The 100% elution fraction was further purified on a Phenomenex $C_{18}$ column as described before. A single peak with the correct diode array profile cleanly eluted at 16.6 min. By ESI-MS analysis, this HPLC-peak contained the 1099 ion. The concentration of trichamide was below a measurable limit and was thus estimated by comparison of the diode array absorbance at 240 nm with those for standards of ulithiacyclamide at varying concentrations. This intensity depends mainly upon the concentration of thiazole, since both ulithiacyclamide and trichamide have no other chromophores at this wavelength. By this method, the total amount of trichamide isolated was estimated to be 25-50 µg.

(4) Mass Spectrometry

Crude extracts and partially purified fractions were monitored by ESI-MS and by FT-MS on a ThermoFinnigan LTQ-FT at 100,000 resolution (i.e. mass 400). FT-MS/MS experiments were run with collision-induced dissociation (CID) and infrared multiphoton dissociation (IRMPD) techniques. Predicted masses were calculated using the following values: C=12, H=1.007825, N=14.003074, O=15.994914, S=31.97207.

b) Results and Discussion (1) Biosynthetic Genes

Using genomic data available from GenBank, a 12.5 kb gene cluster proposed to be responsible for the biosynthesis of trichamide (hence named tri cluster) has been annotated. The % GC is 40, higher than the average % GC of *T. eryth-raeum* at 34. On both sides it is bordered by tRNA-synthetase genes, potentially implicating horizontal gene transfer. The *T. erythraeum* genome is not closed, currently residing in 52 contigs at GenBank. The contig containing the tri genes (GenBank accession: NZ_AABK04000003) is 842 kb long and also contains a number of ribosomal proteins. A BLAST analysis of the ribosomal proteins finds similarities in other cyanobacteria, so it is assumed that this contig is indeed from *T. erythraeum* and not from a possible contamination by heterotrophic bacteria.

Figure 4:
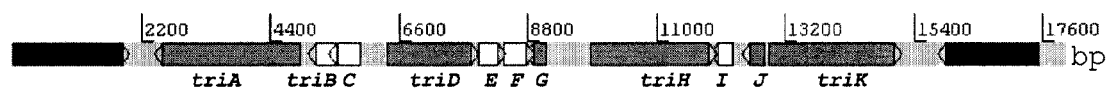
FIG. 4 shows the tri gene cluster. Arrows denote ORFs and their direction, black ORFs are tRNA synthetases, white ORFs are conserved hypothetical without homolog in the pat cluster, green ORFs are pat homologs, the precursor peptide gene is in orange.

The tri cluster contains 11 ORFs designated triA-K (FIG. 4 and Table 4). Four of these (triBCEF) are short and have sequence identity only to conserved hypothetical proteins, while triI is only hypothetical with no significant sequence identities. Some of these ORFs may not be actively transcribed.

TABLE 4 the tri cluster proteins and their homologs.

| Protein | length (aa) | Homolog (GenBank accession) | % identity/ % similarity | Predicted Function | GenBank accession |
|---|---|---|---|---|---|
| TriA | 769 | PatD (AAY21153) | 57/70 | Adenylation/ Heterocyclization | ZP_00672901 |
| TriB | 112 | Conserved hypothetical (NP_942321) | 53/70 | — | ZP_00672900 |
| TriC | 124 | Conserved hypothetical (BAB73591) | 60/78 | — | ZP_00672899 |
| TriD | 475 | PatG, N-terminal (AAY21156) | 45/59 | oxidase | ZP_00672897 |
| TriE | 106 | transposase-like (ZP_00345329) | 79/85 | — | ZP_00672896 |
| TriF | 112 | Conserved hypothetical (ZP_00675293) | 78/91 | — | ZP_00672895 |
| TriG | 67 | None | — | Precursor protein | 794178..381 of NZ_AABK04000003 |
| TriH | 666 | PatA (AAY21150) | 60/72 | Subtilisin-like protease | ZP_00672894 |
| TriI | 72 | — | — | — | ZP_00672893 |
| TriJ | 71 | PatB (AAY21151) | 52/70 | — | ZP_00672892 |
| TriK | 702 | PatG, C-terminal (AAY21156) | 48/64 | Subtilisin-like protease | ZP_00672891 |

The product of triG is the putative precursor protein. It was identified by two 5 amino acid motifs (GPGPS, SYDGD) (SEQ ID NOS: 17 and 18) (*SEthat closely resemble the proposed cyclization signal found before and after the patellamide A and C sequences in the precursor protein of patellamide biosynthesis, PatE (FIG. 5). Analogous to patellamide biosynthesis, these motifs would define the borders of the eleven amino acid peptide, GDGLHPRLCSC (SEQ ID NO: 19). TriG also contains a leader sequence of 43 amino acids without similarities in GenBank except that the first 5 amino acids are identical to those of PatE.

TriA has high similarity to patD, which is proposed to be involved in heterocyclization of cysteine and/or threonine/serine into thiazoline and oxazoline rings. The putative function was assigned on the basis of low sequence identity to previously characterized proteins: for the N-terminal part the adenylating enzyme MccB from microcin biosynthesis [Gonzalez-Pastor et al. J. Bacteriol. 177: 7131-7140], for the C-terminal part a possible hydrolase, SagD from *Streptomyces iniae* [Fuller et al. Infect. Immun. 70: 5730-5739].

TriD has high similarity to the N-terminal part of PatG and to oxidases. It was predicted that this part of PatG would oxidize the intermediate thiazoline rings into thiazoles.

BLASTP analysis of TriH and K gives homology to sub-tilisin-like proteases. They have high similarity to PatA and the C-terminal part of PatG. It was predicted that these proteases would be involved in the maturation of PatE by cleaving the product from leader and trailer sequence and assume the same function in trichamide biosynthesis. It is interesting to note that TriH and TriK have 48% identity to each other.

TriJ has 50/72% similarity/identity to PatB. There is no other homolog to either of the two proteins in GenBank. PatB is not required for biosynthesis but seems to improve patel-lamide yield in heterologous expression experiments with the pat cluster. The high identity between TriJ and PatB over their entire length and presence in both clusters does suggest that they serve a role in peptide biosynthesis.

There are few differences between the pat and tri clusters: PatG has two domains: one for oxidation and one for proteolytic cleavage. In *T. erythraeum* these functionalities are separated into two proteins, TriD and TriH, respectively. The only pat gene without a homolog in the tri cluster (excluding very short putative ORFs) is patF, which has no significant homologies in GenBank. Overall, the pat and tri clusters have striking similarities. The biosynthetic genes have between 45-60% identity, and both gene clusters consist of a heterocyclization enzyme, an oxidase, two proteases and patB/triJ, a gene of unknown functionality. Also, while there is variability in the length of the precursor protein, both in terms of the leader sequence as well as in product sequence (8 amino acids for patellamide, 11 for trichamide), the five amino acid cyclization signals before and after the peptide are highly conserved.

Based upon these similarities in biosynthesis genes, the presence of a patellamide-like compound, trichamide, a cyclic, thiazole-containing peptide in *T. erythraeum* was predicted. Depending on the pattern of cyclization of the peptide and/or heterocyclization of serine and cysteine moieties, the possible molecular weight of the compound is between 1079 and 1157.

(2) Mass Spectrometry

Initial screening of a crude extract of *T. erythraeum* with MALDI-TOF MS revealed the presence of a major peak at 1099. A molecule with this mass can be constructed from the precursor peptide sequence GDGLHPRLCSC (SEQ ID NO: 19) by heterocyclization and oxidation of two of the three possible amino acids—cysteine, serine, cysteine—to thiazoles or oxazoles and cyclization of the entire peptide. Alternatively, this mass is also consistent with heterocyclization of the remaining amino acid to a thiazoline or oxazoline moiety in a linear peptide.

A high-resolution experiment on a Fourier-Transform MS/MS system gave a molecular ion at (M+H)*2 550.23166, only 0.022 ppm different from the theoretical value of (M+H)*2 550.231648 for the predicted structure, validating the presence of a molecule containing the trichamide molecular formula $C_{46}H_{66}N_{16}O_{12}S_2$.

Further MS/MS fragmentation experiments of mass 550.2 using collision-induced dissociation (CID) and infrared multiphoton dissociation (IRMPD) techniques revealed fragmentation patterns in congruence only with a cyclic peptide (Table 5). With the exception of ion A, all masses are within ~3 ppm of their predicted values. This leaves three possible heterocyclization patterns that have identical mass: 1) thiazole-serine-thiazole; 2) thiazole-oxazole-cysteine; and 3) cysteine-oxazole-thiazole. The data are consistent with 1) on the basis of three arguments: First, heterocyclization of adjacent amino acids has no precedent in the patellamide structural literature; in fact when two cysteine residues are adjacent in the patellamide family as in the ulithiacyclamides [Fu X., T. Do, F. J. Schmitz, V. Andrusevich, M. H. Engel. 1998. New cyclic peptides from the ascidian *Lissoclinum patella*. J. Nat. Prod. 61:1547-1551], only one is cyclized. Second, the patel-lamide class of compounds does not contain oxazoles, but only oxazolines. Third, it is highly unlikely that an enzyme would specifically modify one cysteine but not the other.

TABLE 5

Mass spectrometry. Proposed peptide structure are in one-letter amino acid code, Thia = cysteine modified to thiazole. Artifacts intrinsic to the machine and visible in other spectra of unrelated molecules constitute the other major peaks in the spectrum and are not tabulated here.

|  | ion | proposed structure | observed mass | theoretical mass | difference (ppm) |
|---|---|---|---|---|---|
| FT-MS | I | M + H * 2, GDGLHPRL-Thia-S-Thia | 550.23166 | 550.231648 | 0.022 |
|  | II | M + H * 2, $^{34}$S | 551.22845 | 551.22955 | 2.0 |
|  | III | M + H, $^{13}C_2$ | 551.23627 | 551.2350025 | 2.3 |
| CID-MS/MS of 550.2 | A | M + H * 2 of ion F | 481.20212 | 481.19883 | 6.8 |
|  | B | M + H * 2 of parent ion minus C=O | 536.23520 | 536.23520 | 0.0 |
|  | C | M + H, PRL-Thia-S-Thia-GD | 792.29387 | 792.29213 | 2.2 |
|  | D | M + H, PRL-Thia-S-Thia-GDG | 849.31559 | 849.31359 | 2.4 |
|  | E | M + H, PRL-Thia-S-Thia-GDGL | 962.39975 | 962.39766 | 2.2 |
|  | F | M + H, HPRL-Thia-S-Thia-GDG | 986.37429 | 986.37250 | 1.8 |
| IRMPD-MS/MS of 550.2 | G | M + H * 4 of parent ion | 275.11674 | 275.115824 | 3.3 |
|  | H | M + H, G-L-H | 308.17152 | 308.17220 | 2.2 |
|  | I | M + H * 2 of parent ion | 550.23035 | 550.231648 | 2.4 |
|  | J | M + H, RL-Thia-S-Thia-GD | 695.23870 | 695.239367 | 1.0 |
|  | K | as ion C | 792.29121 | 792.29213 | 1.2 |
|  | L | M + H, L-Thia-S-Thia-GDGLH | 846.30172 | 846.302694 | 1.2 |
|  | M | as ion E | 962.39676 | 962.39766 | 0.9 |

Figure 6:
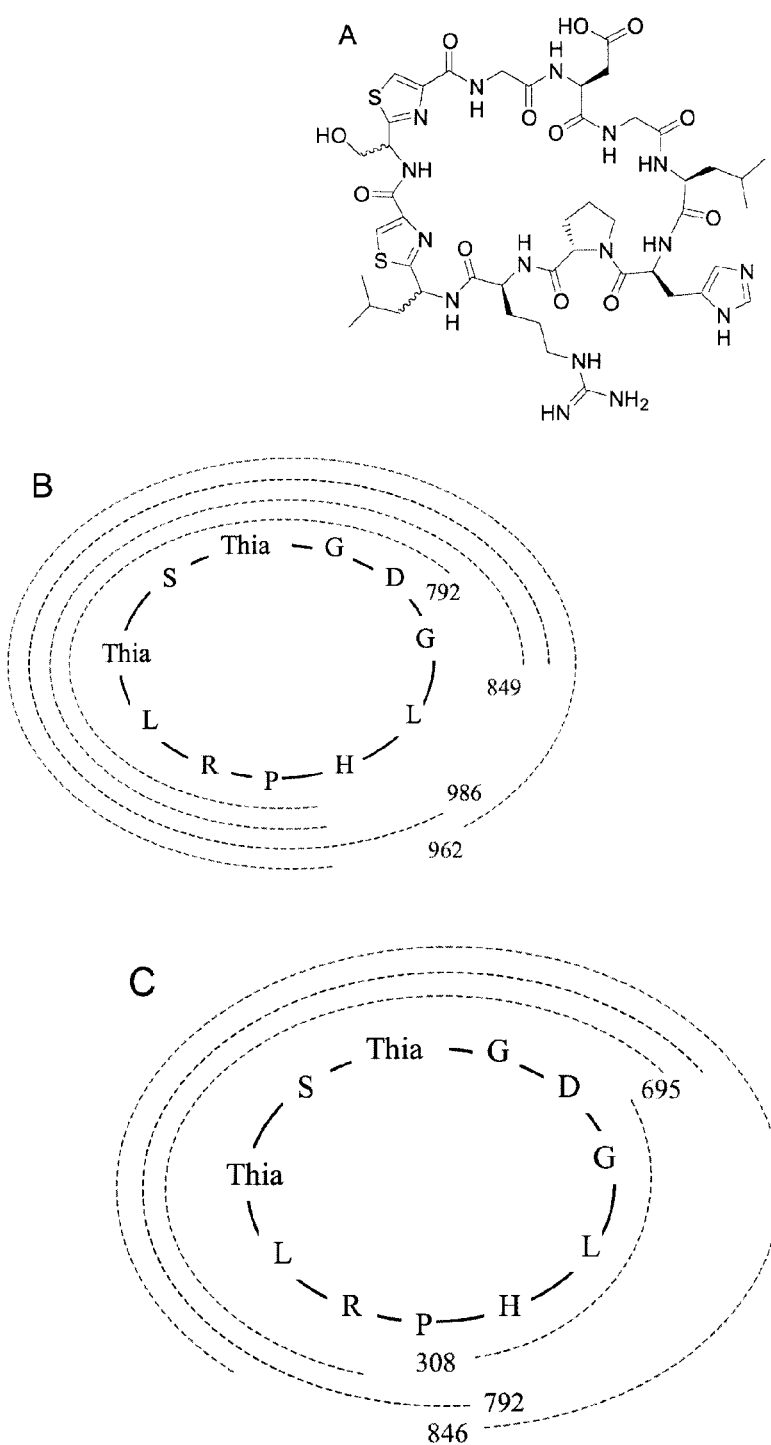

Because of the ribosomal mode of synthesis and in accordance with the patellamides, all of the amino acids in this molecule should adopt the L-configuration. Exceptions to this rule may be serine and leucine 2, which are adjacent to thiazole. These stereocenters readily undergo epimerization, and they are often found in either the D or L form in patella-mides. The proposed structure of trichamide is shown in FIG. 6.

6. Biosynthetic Pathway

Closely paralleling patellamide biosynthesis, the following pathway is shown for trichamide biosynthesis (FIG. 7).

TriG is the precursor protein and forms the substrate for posttranslational modification by TriA, D, H and K. First, TriA modifies the cysteine moieties of TriG to form thiazoline groups. This could be an ATP consuming process as in microcin heterocyclization [Milne J. C., A. C. Eliot, N. L. Kelleher, C. T. Walsh. 1998. ATP/GTP hydrolysis is required for oxazole and thiazole biosynthesis in the peptide antibiotic microcin B17. Biochemistry 37: 13250-13261], needing the ATP hydrolysing functionality of the N-terminal part of TriA, while the reaction itself would be catalyzed by the uncharacterized C-terminal part. Next, TriD oxidizes thiazolines to thiazoles. TriA and TriK cleave the propeptide guided by the conserved motifs GXXXS and XYDG (SEQ ID NOS: 35 and 36). It appears that one protease cleaves the peptide bond after the header sequence leading to a free amide group. The other protease cuts the back end and catalyze a transpeptidation reaction between the two ends of the peptide leading to the mature cyclic form in a mechanism similar to the well characterized peptidoglycan cyclization by a serine protease, penicillin binding protein (Scheffer D., M. G. Pinho. 2005. Bacterial cell wall synthesis: New insights from localization studies. Microbiol. Mol. Biol. Rev. 69: 585-607). It is possible that the significant similarities between the two proteases allow them to form a dimer, which catalyzes both the hydrolysis of two peptide bonds and the cyclization in concert. It is interesting to note that the biosynthetic cluster of the linear peptide goadsporin [Onaka H., M. Nakaho, K. Hayashi, Y. Igarashi, T. Furumai. 2005. Cloning and characterization of the goadsporin biosynthetic gene cluster from *Streptomyces* sp. TP-A0584. Microbiology 151: 3923-3933] does not contain the two subtilisin-like proteases found in the tri and pat clusters, in agreement with an involvement of TriHK in cyclization. Recently Milne et al. published a computational study in which preorganization of patellamides were predicted to lead to cyclization and an enzyme would thus not be required [Milne B. F., P. F. Long, A. Starcevic, D. Hranueli, M. Jaspars. 2006. Spontaneity in the patellamide biosynthetic pathway. Org. Biomol. Chem. DOI: 10.1039/b515938e]. The differences in size and sequence and the maintenance of dedicated proteases in patellamides and trichamide argue against this possibility. Finally, the absence of a PatF homolog in *T. erythraeum* and the requirement of PatF in patellamide biosynthesis implicate PatF in oxazoline formation, which is not part of the trichamide pathway.

Patellamide and trichamide biosynthesis can be examples of a more common pathway to small peptides. Besides the aforementioned goadsporin from *Streptomyces* sp. TP-A0584, at the time of this writing clustered ORFs with 35-40% identity to TriA and D are present in the genomes of phylogenetically distant bacteria: plut_0880 and 0878 in *Pelodictyon luteolum*, Chlorobia (GenBank accession: CP000096), swolDRAFT_1502 and 1501 in *Syntrophomonas wolfei*, Chlostridia (GenBank accession: NZ_AAJGOO000002), and blr4538 and 4539 in *Bradyrhizobium japonicum*, Rhizobiales [21] (GenBank accession: BA000040).

(4) Trichamide Function

Trichamide is hydrophilic, partitioning to the aqueous fraction relative to ethyl acetate. In addition, it is found only in the cells and is not excreted in significant quantities to the growth medium. These properties suggest an antipredation defense function, rather than anticompetitor or communication functions. To test biological activities, *T. erythraeum* crude methanolic extracts were tested for general cytotoxicity (HCT-116 at 10 μg/ml and CEM-TART at 5 and 50 μg/ml) and anti-HIV (1 and 10 μg/ml), antifungal (*Candida albicans* at 10 μg/ml) or antimicrobial (*Staphylococcus aureus* and *Enterococcus faecium* at 10 μg/ml) effects. No significant activity was found in these assays (data not shown). A number of algal blooms have neurotoxic effects and neurotoxicity of environmental *Trichodesmium* sp. in mice has previously been reported. The crude methanolic extract of *T. erythraeum* IMS101 also exhibited neurotoxicity in a mouse assay, but purified trichamide was not the active component. Guo and Tester have found that healthy *Trichodesmium* sp. cells do not affect the copepod *Acartia tonsa*, while aged or lysed *Trichodesmium* cells are toxic. This result is consistent with the properties of trichamide, which suggest that the compound is maintained inside healthy cells, but would be released into seawater from lysed cells.

3. Example 3

Rapid Recombination of Secondary Metabolic Pathways in Marine Symbiotic Bacteria a) Methods Collection and processing of samples. Ascidians were collected in Palau in 2002, the Madang region of Papua New Guinea in 2003, and the Milne Bay region of Papua New Guinea in 2005. Ascidians were monitored for the presence of *Prochloron* spp. by visual inspection and light microscopy. *Prochloron* cells have a characteristic large (10-20 □m), spherical shape and have a deep green color due to the presence of both chlorophylls a and b and the lack of accessory pigments. *Prochloron*-containing ascidians were stored frozen (for chemical analysis), or in RNALater or ethanol for later DNA analysis. Some samples, with the exception of size-limited samples, could be enriched for *Prochloron* cells by simple expression of the bacteria from the organisms followed by gentle centrifugation. Such enriched *Prochloron* samples were stored in RNALater or processed to obtain purified DNA as previously described. RNALater-stored, whole ascidian samples were ground in liquid nitrogen and processed using the Qiagen DNA Spin Kit. The presence of purified DNA was monitored by agarose gel electrophoresis.

Analysis of pate variability. Samples were diluted into 3 concentrations (1×, ⅒× and ⅟₁₀₀×), then PCR amplification of the 3 concentrations was done using pate specific primers and HiFi Platinum Taq Polymerase (Invitrogen). Products were visualized with agarose gel electrophoresis. Bands of the appropriate size were excised and gel-extracted using the QIAquick Gel Extraction Kit (Qiagen), and amplified pate were direct sequenced by the Sequencing Core Facility of the University of Utah. Sequences were analyzed using Sequencher and BLAST searches. Multiple pate variants from the same strain were de-convoluted by visual inspection, leading to the initial identification of patE2-patE6. The presence of the new pate genes was confirmed by PCR using specific primers.

Pathway analysis. PCR amplification was used to test the conservation of regions flanking new pate genes. Oligonucleotides patEF and patFR were used to amplify the two-gene fragment, patE-patF, while patDF and patER were used to amplify patD-patE. Other primers were used also to amplify shorter fragments linking patD to pate. All products with the right size were direct sequenced in both directions and compared to the patellamide cluster DNA sequence.

Taxonomic analysis. Specific primers were used to amplify a portion of the cao gene, as previously described, and the products were treated essentially the same way as the patE products.

Quantitative pathway analysis. Quantitative PCR was carried out on samples 05-019 and 03-005 using Light Cycler FastStart DNA Master$^{PLUS}$ SYBR green I (Roche) and analyzed by the standard curve method. Specific primers were designed for patE1, patE2, and patE3. Samples and controls were run in duplicate.

Chemical analysis of the samples. nine samples (05-019, 05-023, 05-028, 05-042, 03-001, 03-002, 03-009, 03-012, 03-020) were processed in essentially the same manner. First, a piece of ~10 g of the whole organism was diced and extracted twice with methanol (50 mL). Extracts were then combined, dried on a rotary evaporator, and partitioned between ethyl acetate and water. Following rotary evaporation, the ethyl acetate fraction was further partitioned between hexane and methanol. The dried methanol fraction was analyzed by $^1$H NMR (400 MHz) and ESI mass spectrometry. Peaks representing known compounds could be clearly discerned by comparison to literature data and purified standards. To further confirm the presence of key compounds, ulithiacyclamide, patellamide A, patellamide C, lissoclinamides 2-4, and ulicyclamide were purified to homogeneity using literature methods. Sample 05-019, for example, yielded lissoclinamides 2-4 and ulicyclamide, as confirmed by $^1$H NMR and mass spectrometry.

4. Example 4

Patellamide A and C Biosynthesis by a Microcin-Like Pathway in Prochloron didemni, the Cyanobacterial Symbiont of Lissoclinum patella a) Materials and Methods (1) Purification of Prochloron DNA L. patella was collected in the Republic of Palau in 2002. One ascidian colony (25 cm$^2$) was washed with sterile seawater and gently pressed to release Prochloron, which were purified by centrifugation. Within 15 minutes of harvesting, Prochloron DNA was obtained from freshly released cells using the Genomic-Tip kit (Qiagen), following the bacterial DNA purification protocol. P. didemni was enriched to >95% homogeneity, as evidenced by light microscopy and denaturing gradient gel electrophoresis of the 16S rRNA gene. The DNA obtained was ~40 kbp, as indicated by gel electrophoresis. Two strains were obtained in this collection, both from single colonies of L. patella. One strain, designated "reef", was collected from a fringe reef near Blue Corner, while the "Omodes" sample was collected in the Omodes seagrass bed near Koror Island.

(2) Genome Sequencing and Analysis

Two libraries were constructed from 12 μg of genomic DNA extracted from the "reef" sample with insert size of 2-5 kb and 6-8 kb. A total of 31,473 sequencing reads were obtained with an average length of 857 bp, corresponding to about 3× coverage of the predicted genome size (5 Mb). The genome was assembled using the Celera Assembler (Huson, H. D., Reinert, K., Kravitz, Z. A., Remington, K. A., Delcher, A. L., Dew, I. M., Flanigan, M., Halpern, A. L., Lai, Z., Mobarry, C. M., Sutton, G. G. & Myers, E. W. (2001) Bioinformatics 17, S132-139) into 734 scaffolds ranging in size from 1 to 77 kb. The scaffolds were randomly concatenated into a pseudomolecule, which was processed with the gene finder Glimmer (Delcher, A. L., Hannon, D., Kasif, S., White, O. & Salzberg, S. L. (1999) Nucleic Acids Res. 27, 4636-4641). Auto-annotation was performed as previously described (Tettelin et al. (2001) Science 293, 498-506) using a combination of Hidden Markov Models [TIGRFAM (Haft, D. H., Loftus, B. J., Richardson, D. L., Yang, F., Eisen, J. A., Paulsen, I. T. & White, O. (2001) Nucleic Acids Res. 29, 41-43) and PFAM (Bateman, A., Birney, E., Cerruti, L., Durbin, R., Etwiller, L., Eddy, S. R., Griffiths-Jones, S., Howe, K. L., Marshall, M. & Sonnhammer, E. L. (2002) Nucleic Acids Res. 30, 276-280] and BLAST analysis for predictive assignment of protein function.

The pre-patellamide peptide was identified using TBLASTN by querying each of the 8 linear amino acid combinations of the cyclic peptide patellamide A in the genome scaffolds nucleotide sequence. Manual curation of the cluster's annotation was performed using the open source MANATEE system (www.tigr.org/software/).

(3) Fosmid Library Construction

Genomic DNA was prepared from Prochloron gDNA "reef" sample using the Genomic-Tip kit to yield DNA fragments of about 40 kbp in size. This DNA was directly ligated to the pCC1FOS vector (Epicentre) following the manufacturer's instructions. The titer from this method was very low, and the entire packaging extract was used to generate a 600-clone library. This library was representative of the sample and did not contain colonies with identical inserts, as judged by screening for a known Prochloron gene (Tomitani, A., Okada, K., Miyashita, H., Matthijs, H. C. P., Ohno, T. & Tanaka, A. (1999) Nature 400, 159-162), and from fosmid end-sequencing.

(4) Cloning of pat Biosynthetic Cluster

The cluster was amplified from Prochloron gDNA "reef" by PCR using primers Lanti1f (CGTGAAAAT-TGCTCTTTGAATAAAGG) (SEQ ID NO: 20) and Lanti2r (ACGGCAAAGGGAGTTTAAACGG) (SEQ ID NO: 37) with PlatinumTaq HiFi (Invitrogen) and cloned into pCR2.1-TOPO (Invitrogen). Fosmids containing pat were identified from a pCC1FOS arrayed library using the previously reported methods with primers Lanti1f, Lanti2r, Lantimid1r (CGCAGCTACGAGCAAAACATTG) (SEQ ID NO: 38) and Lantimid1f (CCACAGTTGAGGCCAGCAC) (SEQ ID NO: 39). The two sets of primers were also applied to whole genomic DNA samples extracted from the patellamide A/C-producing strain of Prochloron ("reef"), and from the non-producing strain ("Omodes").

(5) Chemical Analysis

Patellamides A and C were isolated from whole L. patella, purified to homogeneity, and identified as previously described. Briefly, the compounds were extracted with methanol and purified by partitioning followed by silica gel chromatography. Fosmid clones containing pat were grown in 1 L of LB-chloramphenicol (12.5 mg/L) to an OD$_{600}$ of 0.1-0.3. Induction to high-copy number of the fosmid was performed according to the manufacturer's instructions and followed by an additional 24-48 hour incubation at 37° C. The pCR2.1-pat plasmid was transferred to E. coli BL21(DE3) pLys cells (Stratagene). Fresh colonies were grown in 1 L of LB-ampicillin (50 mg/nL) for approximately 24 hours at 37° C. with 1 mM IPTG.

To each 1 L culture broth, HP20SS (~50 g, Supelco) resin was added, and the mixture was incubated for 1-2 hours. The resin was filtered and rinsed with dH$_2$O (2×100 mL) and 25% aqueous methanol (2×100 mL). The resin was then rinsed twice with methanol (100 mL) and acetone (100 mL), and the organic fractions were combined and dried by rotary evaporation. The extract was partitioned between chloroform and 25% aqueous methanol. The chloroform layer was evaporated to dryness and further extracted with equal volumes of hexanes and methanol. The methanol fractions were dried, resuspended in methanol (250 μL), and used directly for HPLC-ESI MS analysis. In addition, a standard was prepared in which 25 mL of culture broth containing HP20SS resin was set aside prior to filtration. To this broth was added a mixture of patellamides A and C (10 μg each), and the resulting mixture was treated by filtration and partition as described above.

HPLC-ESI MS analysis was performed on a ThermoFinnigan LCQ Classic ion trap mass spectrometer. For HPLC, an analytical C18 column (Microsorb-MV, Varian) was used with a methanol-water gradient. An initial 50-50 mixture of methanol and water (each containing 0.1% formic acid) was subjected to a gradient to 95% methanol over 15 minutes, followed by 10 minutes at 95% methanol. ESI-MS was performed in the positive mode, and selective reaction monitoring (SRM) was applied to patellamide peaks at m/z=743 and 763.

b) Results and Discussion (1) Prochloron Preparation and Purity

Prochloron cells were prepared from whole L. patella and determined to be >95% pure, as previously described. This 95% purity represents a conservative estimate.

(2) Chemical Analysis of L. patella "Reef" and "Omodes"

It was previously reported that the "reef" sample contained patellamides A and C (Ireland, C. M., Durso, A. R., Newman, R. A. & Hacker, M. P. (1982) J. Org. Chem. 47, 1807-1811) in nearly equimolar amounts. Other patellamides were not detected as major products in the crude extract. The "Omodes" sample did not contain detectable patellamides, and this was one of the criteria used to select "reef" for whole genome sequencing.

(3) Identification of pat Genes

Previously, an exhaustive PCR-based search for NRPS adenylation domains yielded only a single NRPS gene, prnA (GenBank accession number AY590470). Detailed analysis of PrnA revealed that it has the wrong domain architecture for patellamide biosynthesis. Furthermore, it has been found in some patellamide-producing strains but not others. It was suggested that these results could indicate that prnA is not responsible for patellamide production; alternatively, prnA-like genes could be highly variable and thus were not detected in all peptide-producers. The preliminary analysis of the draft genome sequence of P. didemni showed that prnA contained the only NRPS adenylation domain identified, bearing out the PCR data. Thus, a ribosomal synthesis of patellamides was a strong possibility. We performed a TBLASTN search of the draft genome sequence, querying for all eight possible peptides that could lead to the formation of the cyclic patellamide A. A single coding sequence (CDS) was identified, and strikingly this CDS also contained the required sequence for patellamide C. Because of the low probability that these sequences could co-occur by chance, this gene was identified as a candidate for the patellamide precursor peptide, patE (FIG. 16). No other oligopeptide 8-mers with identical sequence to patellamide A or C could be identified in GenBank, and the entire patE precursor peptide was not closely related to any other known or predicted CDS. Because of the low probability that these sequences could co-occur by chance, this gene was identified as a candidate for the patellamide precursor peptide, patE (FIG. 16). The presence of two peptide products on a single CDS suggests that synergy may be important to the patellamide mechanism of action (Chatterjee, C., Paul, M., Xie, L. & van der Donk, W. A. (2005) Chem. Rev. 105, 633-684).

Surrounding patE, there were several other CDS with intriguing sequences, comprising the patA-G genes in a ~11 kbp cluster (FIG. 17; Table 6). In particular, a protease (patA), a possible adenylating enzyme-hydrolase hybrid (patD), and an oxidoreductase-protease hybrid (patG) immediately surround patE. Three other CDS with very low or no similarity to other proteins of known function (patB, patC, and patF) are also found in this cluster. On one side, this cluster ends with a gene that can be clearly assigned to primary metabolism (a DNA photolyase homolog), while on the other side a putative structural gene was identified extending approximately 1 kbp upstream of patA. These genes and the organization of the cluster are reminiscent of lantibiotic and microcin biosynthetic machinery, which has been characterized in other bacteria (Garneau, S., Martin, N. I. & Vederas, J. C. (2002) Biochemie 84, 577-592; Jack, R. W. & Jung, G. (2000) Curr. Opin. Chem. Biol. 4, 310-317). In particular, the microcin B17 peptide contains heterocycles (Yorgey, P., Lee, J., Kordel, J., Vivas, E., Warner, P., Jebaratnam, D. & Kolter, R. (1994) Proc. Natl. Acad. Sci. USA 91, 4519-4523), while microcin J25 (Wilson, K. A., Kalkunt, M., Ottesen, J., Yuzenkova, J., Chait, B. T., Landick, R., Muir, T., Severinov, K. & Darst, S. A. (2003) J. Am. Chem. Soc. 125, 12475-12483) is cyclic.

TABLE 6 orfs from the pat cluster.

| Protein | Amino acids | Proposed Function | Sequence similarity | Identity/ Similarity | GenBank Accession # |
|---|---|---|---|---|---|
| PatA | 702 | Subtilisin-like protease | Hypothetical; T. erythraeum | 57/69% | ZP_00326030.1 |
| PatB | 78 | Unknown | Hypothetical; T. erythraeum | 52/70% | ZP_00326032.1 |
| PatC | 64 | Unknown | None | — | — |
| PatD | 784 | Adenylation/ heterocyclization | Hypothetical; T. erythraeum | 57/70% | ZP_00326023.1 |
| PatE | 71 | Patellamide precursor protein | None | — | — |
| PatF | 320 | Unknown | None | — | — |
| PatG | 1187 | Thiazoline oxidase/ subtilisin-like protease | 2 Hypothetical proteins; T. erythraeum | 43/57% (N-terminus) 48/63% (C-terminus) | ZP_00326026.1 (N-terminus) ZP_00326033.1 (C-terminus) |

(4) Functional Expression of pat Genes

Using PCR, four fosmid clones containing patE were identified in a 576-clone arrayed library (FIG. 18). From analysis of the fosmid end sequences, three of these (designated 21A, 28C, and 55F) were found to contain the complete pathway. Additionally, the region encompassing patA-patG, including putative regulatory regions, was amplified by PCR from whole "reef" genomic DNA and cloned into the pCR2.1-TOPO vector Invitrogen). 1 L cultures from these fosmids and PCR clones were extracted and partially purified. Positive controls were established by adding patellamides A and C (0.4 mg/L each) directly to *E. coli* culture broths containing vectors, then extracting these cultures in the same way that other samples were processed. An HPLC-ESI MS approach was used to identify patellamides in our extracts.

Two standards were used to set up MS conditions. In the first, pure patellamides A and C, positively identified by NMR ($^1$H and $^{13}$C) and mass spectrometry, were used for direct infusion and HPLC-MS experiments. In the second, a standard containing an initial 0.4 mg/L of each patellamide was used for HPLC-MS. From both standards, molecular ions for patellamides A and C could readily be recognized in the mass spectrum (FIG. 18). Partially purified samples from fosmid and PCR clones were then injected. In all cases, blank or negative runs followed the injection of standards and did not contain the relevant ions. Ions of the appropriate mass could be identified at the correct elution time from these samples, but the signal-to-noise ratio was not sufficient to conclusively prove the presence of patellamides. To confirm that these peaks resulted from patellamides, SRM was employed, a commonly used technique in which sought ions are captured and fragmented by MS-MS. The mass spectrometer then scans only for a single daughter ion. This technique is both extremely sensitive and less subject to error because three pieces of data are obtained from a single experiment (elution time; presence of the parent ion; and fragmentation to a very specific daughter ion). Using this technique, patellamide A could be observed in the standard by monitoring for a major daughter ion at m/z=725 (FIG. 18). In addition, patellamide C was seen in the standard by monitoring for the daughter ion at m/z=680, although with much less sensitivity than for patellamide A. The patellamide A peak at m/z=725 was observed in PCR clones and in fosmid extracts in a peak centered at 20.7 min (FIG. 18), indicating that patellamide A can be heterologously produced in *E. coli*. In particular, a 2 L fermentation of a PCR clone led to a very clear identification of patellamide A, as shown in FIG. 18. It is estimated that at most 20 µg/L of patellamide A are produced under these conditions.

These data unambiguously confirm that the patA-G gene cluster is responsible for patellamide biosynthesis in *P. didemni*. Because patellamide A is produced by clones containing the ~11 kbp PCR product, we have also correctly identified the limits of the biosynthetic gene cluster.

(5) Correlation of the Presence of the pat Gene Cluster with Patellamide Production While the pat pathway could be amplified using DNA from the patellamide-producing "reef" strain, no products were amplified from the non-producing "Omodes" strain. DNA quantity and quality from these two strains were identical, as judged by multiple PCR techniques, denaturing gradient gel electrophoresis of 16S rDNA, UV spectroscopy, and quantitative gel electrophoresis. Thus, the patellamide cluster was found in a producing strain but was not present in a non-producer. Because these two strains appear to be very similar by sequencing of several gene classes (chlorophyll a oxidase, 16S rDNA, and the prn NRPS operon), it is possible that pat and similar clusters in *Prochloron* originate via horizontal gene transfer, as has been proposed for other lantibiotic pathways (Fomenko, D. E., Metlitskaya, A. Z., Peduzzi, J., Goulard, C., Katrukha, G. S., Gening, L. V., Rebuffat, S. & Khmel, I. A. (2004) *Antimicrob. Agents Chemother.* 47, 2868-2874). In fact, the cao and 16S rDNA genes are identical between *Prochloron* strains, while prn is >98% identical. Further research is required to determine the origin and role of these pathways in *Prochloron*.

(6) PatE, a Precursor Peptide Encoding Patellamides A and C patE encodes a peptide of 71 amino acids, the first 37 of which are proposed to serve as a leader sequence for processing (FIG. 16). Of the remaining 34 amino acids, 16 directly encode the patellamide C and A sequences, while 18 make up motifs that we propose direct the cyclization of patellamides. The patellamide C peptide is located 8 amino acids upstream of the patellamide A sequence. Prior to both peptides, there is a 5-amino acid conserved region consisting of the consensus G(L/V)E(A/P)S (SEQ ID NO: 40). The sequence AYDGE (SEQ ID NO: 12) terminates the patellamide A sequence and directly precedes the stop codon. Between the two patellamides, the 8 amino acid sequence AYDGVEPS (SEQ ID NO: 11) appears to encode for both a start and stop cyclization sequence, with the consensus stop sequence being AYDG(E/V) (SEQ ID NO: 41). These sequences are of biotechnological interest because they imply that diverse sequences could be synthesized to take advantage of these consensus regions, leading to the biosynthesis of a library of patellamides. It should be emphasized that the roles of these start/stop roles are putative further characterization is required. However, the microcin B17 prepeptide has been shown to be essential for proper post-translational modification (Madison, L. L., Vivas, E. I., Li, Y.-M., Walsh, C. T. & Kolter, R. (1997) *Mol. Microbiol.* 23, 161-168). Conserved residues in leader sequences are known to be important in the modification of some lantibiotics (van der Meer, J. R., Rollema, H. S., Siezen, R. J., Beerthuyzen, M. M., Kuipers, O. P. & de Vos, W. M. (1994) J. Biol. Chem. 269, 3555-3562; Xie, L., Miller, L. M., Chatterjee, C., Averin, O., Kelleher, N. L. & van der Donk, W. A. (2004) *Science* 303, 679-682), and a consensus sequence (GAEPR) (SEQ ID NO: 42) found in these prepeptides bears a striking resemblance to the PatE start consensus motif, G(LN)E(A/P)S (SEQ ID NO 40). Class I lantibiotics appear to usually possess a Pro residue at the –2 position, although in the case of nisin this Pro could be substituted with Gly and Val without impacting production. Another general feature of class I lantibiotic leader peptides also found in PatE is a high proportion of charged residues.

Lantibiotics also contain C-terminal propetide sequences that are cleaved by proteases, often in tandem with secretion from the cell.

(7) The Patellamide Post-Translational Machinery

The pat cluster encompasses 7 genes, patA-G, which are all transcribed in the same direction and may comprise an operon. Sequence analysis of these genes allows the proposal of a biosynthetic pathway to patellamides (FIG. 19). PatA, PatD, and PatG (Table 6) are most similar to predicted proteins found clustered in the genome of *Trichodesmium erythraeum* IMS101 (GenBank accession number AABK00000000). In addition, PatB also is most related to a *T. erythraeum* gene, although the *T. erythraeum* PatB homolog is not closely clustered with the PatA, PatD, and PatG homologs. The significance of this clustering in *T. erythraeum* is discussed in the next section.

The PatA N-terminal region is similar to subtilisin-like proteases, which are usually involved in the recognition of signature sequences in hormone precursor peptides and the cleavage of these peptides near a signature motif (Schnell, N., Entian, K.-D., Schneider, U., Götz, F., Zlhner, H., Kellner, R. & Jung, G. (1988) *Nature* 333, 276-278; van der Meer, J. R., Polman, J., Beerthuyzen, M. M., Siezen, R. J., Kuipers, O. P. & De Vos, W. M. (1993) J. Bacteriol. 175, 2578-2588). The C-terminal region of the predicted protein shares no domain homology with proteins of known function, although it is related to hypothetical protein Orf4 from the cyanobacterium

*Fremyella diplosiphon* (Balabas, B. E., Montgomery, B. L., Ong, L. E. & Kehoe, D. M. (2003) *Mol. Microbiol.* 50, 781-793). The predicted protein has a proline-rich region (aa 343-401), although the significance of this motif is unknown. Over its entire length, it is 59% identical to *T. erythraeum* subtilisin-like serine protease ZP_00326030.1. Because of the protease sequence homology, it is proposed that PatA is involved in cleavage of the PatE precursor peptide.

PatD, like PatA, appears to contain 2 domains. The N-terminal domain (PatD1) shares weak similarity with adenylating enzymes, such as acyl-CoA ligases, and with MccB, the adenylating enzyme responsible for the biosynthesis of the microcins C51 and C7 (Gonzalez-Pastor, J. E., San Millan, J. L., Castilla, M. A. & Moreno, F. (1995) *J. Bacteriol.* 177, 7131-7140). The PatD C-terminus (PatD2) is similar to YcaO-like conserved domains of unknown function, but also to SagD from *Streptococcus iniae* that may serve as a hydrolase (Fuller, J. D., Camus, A. C., Duncan, C. L., Nizet, V., Bast, D. J., Thune, R. L., Low, D. E. & De Azavedo, J. C. (2002) *Infect. Immun.* 70, 5730-5739). PatD2 shows similarity to TtufA, a protein involved in the synthesis of the ribosomally derived trifolitoxin (Breil, B., Borneman, J. & Triplett, E. W. (1996) *J. Bacteriol.* 178, 4150-4156). The entire PatD peptide sequence is similar to only a handful of proteins, including the *T. erythraeum* homolog, a protein annotated as AknN (a hydrolase) from *Streptomyces galilaeus*, and Orf12, a predicted protein of unknown function from the granaticin biosynthetic pathway (Ichinose, K., Bedford, D. J., Tomus, D., Bechthold, A., Bibb, M. J., Revill, W. P., Floss, H. G. & Hopwood, D. A. (1998) *Chem. Biol.* 5, 647-659). Two possible roles are thus proposed for PatD. PatD2 may be involved in the cyclization of the cysteine and threonine residues of PatE, leading to thiazoline and oxazoline ring formation. PatD1 could activate cleaved patellamide precursors as adenylates, which would then cyclize to form the final patellamide structures. Alternatively, the ATP-binding region could have an as-yet unknown function. For example, it is known that the microcin B17 heterocyclization complex includes an ATP-requiring enzyme, McbD, which is of unknown function (Milne, J. C., Roy, R. S., Eliot, A. C., Kelleher, N. L., Wokhlu, A., Nickels, B. & Walsh, C. T. (1999) *Biochemistry* 38, 4768-4781). PatD1 does not show significant sequence homology to McbD, but it is often the case in microcin machinery that distantly related peptides serve similar functions.

PatG is a large, multi-domain predicted protein. An N-terminal domain has homology to NAD(P)H oxidoreductases (PatG1). Intriguingly, the amino-terminal region is distantly related to McbC from microcin B17 biosynthesis. McbC functions to oxidize thiazoline rings to the thiazole oxidation state, and it is likely that this is also the function of this region of PatG. This domain is also similar to an oxidase in the pathway to trifolitoxin, another thiazole-containing microcin. The C-terminal half of PatG (PatG2) is highly similar to PatA, containing subtilisin-like protease and *F. diplosiphon* Orf4-like regions. From this domain architecture, it appears that PatG is involved in oxidation and maturation of PatE.

PatB, PatC, and PatF do not have obvious roles in patellamide biosynthesis. In addition, the protein responsible for epimerization is not evident from the sequence analysis, although it seems likely that epimerization could occur in tandem with heterocycle oxidation. The stereocenters adjacent to thiazole rings are highly labile and could also be subject to non-enzymatic epimerization. The D-Ala residues are not derived from Ser, as they are in some lantibiotic pathways (Banerjee, S. & Hansen, J. N. (1988) *J. Biol. Chem.* 263, 9508-9514).

(8) Related Pathways

The closest homologs of the pat cluster are CDS of unknown function from the draft genome sequence of *T. erythraeum* IMS101. patA, patD, and patG are most similar to four clustered CDS found in *T. erythraeum* (see Table 6). In fact, the patG homolog in *T. erythraeum* is split into two separate CDS, comprising an oxidoreductase and a protease. In addition, a short peptide is present in this cluster that shares some structural features with patE. Furthermore, a transposase is found within the *T. erythraeum* gene cluster, possibly indicating that this cluster may move between strains by horizontal transfer. Several other CDS of unknown function and not homologous to pat genes lie within the identified cluster. In addition, streptolysin S has been known as an important mediator of pathogensis in the "flesh-eating" *Streptococcus* spp. since its discovery 50 years ago (Kline, T. C. & Lewin, R. A. (1999) *Symbiosis* 26, 193-198), yet its structure has not been elucidated. The presence of a McbC-like oxidase and a PatD2-like hydrolase (SagD) in the streptolysin S biosynthetic gene cluster (43) indicate that streptolysin S likely contains thiazole rings. Indeed, the predicted streptolysin S prepropeptide contains numerous cysteine residues that could be cyclized.

(9) Symbiosis and Secondary Metabolism

Some didemnid ascidians (including *L. patella*) contained bioactive secondary metabolites, while others did not contain these compounds. All of the ascidians contained *Prochloron*, but not all of the *Prochloron* contain pat-like pathways. Patellamides are often produced in large amounts (up to several percent of animal dry weight), and presumably some selection pressure must be necessary to maintain such a large-scale synthesis. Interestingly, because many *Prochloron* strains lack these pathways, other unknown selection mechanisms must be important to maintain symbiosis, and there are no obvious visible morphological differences between peptide producer and nonproducer ascidians.

Nutrient exchange has been demonstrated to be important for some didemnid-*Prochloron* associations. Photosynthesis by *Prochloron* has been shown to provide 60-100% of the organic carbon theoretically needed by the host (Koike, I., Yamamuro, M. & Pollard, P. C. (1993) *Aust. J. Mar. Fresh. Res.* 44, 173-182), and there is evidence for nitrogen cycling between host and symbiont in addition to nitrogen fixation. *L. patella* actively optimizes growth conditions for its symbiont by moving to regions with proper illumination and by modifying the structure of the tunic covering the upper surface of the colony (Swift, H. & Robertson, D. L. (1991) *Symbiosis* 10, 95-113).

G. Sequences

```
SEQ ID NO: 1
GLEASN¹AYDGVEPSN²AYDGE
(where N¹ or N² can be any length)

SEQ ID NO: 2
GLEASN¹AYDGVEPS
(where N¹ can be any length)

SEQ ID NO: 3
AYDGVEPSN²AYDGE
(where N² can be any length)

SEQ ID NO: 4
PatC and ulithiacyclamide
GLEASVTACITFCAYDGVEPSCTLCCTLCAYDGE

SEQ ID NO: 5
PatC and eptidenmamide
GLEASVTACITFCAYDGVEPSQGGRGDWPAYDGE
```

SEQ ID NO: 6
PatA and PatC
GLEASVTACITFCAYDGVEPSITVCISVCAYDGE

SEQ ID NO: 7
Full-length Trichodesmium
MGKKNIQPNSSQPVFRSLVARPALEELREENLTEGNQGHGPLANGPGPSG

DGLHPRLCSCSYDGDDE

SEQ ID NO: 8
Abbreviated Trichodesmium
GPGPSGDGLHPRLCSCSYDGDDE

SEQ ID NO: 9
Trichodesmium Recognition Sequence
GPGPSNSYDGDDE

SEQ ID NO: 10
GLEAS

SEQ ID NO: 11
AYDGVEPS

SEQ ID NO: 12
AYDGE

SEQ ID NO: 13
GPGPS

SEQ ID NO: 14
SYDGDDE

SEQ ID NO: 15
5'GCATCACTTTTTGCGCTTATGATGGTGTGGAGCCATCTCAGGGCGGAC

GCGGTGACTGGCCTGCTTACGATGGTGAATAA;

SEQ ID NO: 16
5'TTATTCACCATCGTAAGCAGGCCAGTCACCGCGTCCGCCCTGAGATGG

CTCCACACCATCATAAGCGCAAAAAGTGATGC.

SEQ ID NO: 17
GPGPS

SEQ ID NO: 18
SYDGD

SEQ ID NO: 19
GDGLHPRLCSC

SEQ ID NO: 20
CGTGAAAATTGCTCTTTGAATAAAGG (SEE TABLE THREE FOR SEQ ID NOS: 21-34)

SEQ ID NO: 35
GXXXS

SEQ ID NO: 36
XYDG

SEQ ID NO: 37
ACGGCAAAGGGAGTTTAAACGG

SEQ ID NO: 38
CGCAGCTACGAGCAAAACATTG

SEQ ID NO: 39
CCACAGTTGAGGCCAGCAC

SEQ ID NO: 40
G(L/V)E(A/P)S

SEQ ID NO: 41
AYDG(E/V)

SEQ ID NO: 42
GAEPR

SEQ ID NO: 43 (PatE2)
MNKKN(X)$_{31}$GLEASVTACITFCAYDGVEPSCTLCCTLCAYDGE

SEQ ID NO: 44 (PatEdm)
MNKKN(X)$_{31}$GLEASVTACITFCAYDGVEPSQGGRGDWPAYDGE

SEQ ID NO: 45 (PatE)
MNKKNILPQQGQPVIRTAGQLSSQLAELSEEALGDAGLEASVTAGITFCA

YDGVEPSITVCISVCAYDGE

SEQ ID NO: 46 (PatEBS)
MNKKNILPQQGQPVIRTAGQLSSQLAELSEEALGDAGLEASVTACITFCA

YDGVEPSQGGRGDWPAYDGE

SEQ ID NO: 47
MNKKNILPQQGQPVIRTAGQLSSQLAELSEEALGDAGLEASVTACITFCA

YDGVEQSQGGRGDWPAYDGE

SEQ ID NO: 48 (PatEBS2)
MNKKNILPQQGQPVIRTAGQLSSQLAELSEEALGDAGLEASVTACITFCA

YDGVEQSQGGRGDWPAYDGE

SEQ ID NO: 49
GVDASTLPVPTLCSYDGVDASTVPTLCSYDD

SEQ ID NO: 50
GVDASN$^1$SYDGVDASN$^2$SYDD
(where N$^1$ or N$^2$ can be any length)

SEQ ID NO: 51
GVDASTFPVPTVCSYDGVDASTSPLAPLCSYDD

SEQ ID NO: 52
GVDASN$^1$SYDGVDAS
(where N$^1$ can be any length)

SEQ ID NO: 53
SYDGVDASN$^2$SYDD
(where N$^2$ can be any length)

---

What is claimed is:

1. A peptide comprising an amino acid segment comprising:
the amino acid sequence of GLEAS($N^1$)AYDGVEPS($N^2$) AYDGE,
an amino acid sequence at least about 90% identical to the amino acid sequence of GLEAS($N^1$)AYDGVEPS($N^2$) AYDGE, or
the amino acid sequence of GLEAS($N^1$)AYDGVEPS($N^2$) AYDGE having one or more conservative amino acid substitutions;
wherein $N^1$ and/or $N^2$ comprises an amino acid sequence,
wherein $N^1$ or $N^2$ do not comprise one or more of the amino acids A, C, I, F, L, P, S, T, or V.

2. The peptide of claim 1, wherein the amino acid sequence of $N^1$ comprises less than 100 amino acids.

3. The peptide of claim 1, wherein the amino acid sequence of $N^1$ comprises less than 50 amino acids.

4. The peptide of claim 1, wherein the amino acid sequence of $N^1$ comprises less than 20 amino acids.

5. The peptide of claim 1, wherein the amino acid sequence of $N^1$ comprises less than 10 amino acids.

6. The peptide of claim 1, wherein the amino acid sequence of $N^2$ comprises less than 100 amino acids.

7. The peptide of claim 1, wherein the amino acid sequence of $N^2$ comprises less than 50 amino acids.

8. The peptide of claim 1, wherein the amino acid sequence of $N^2$ comprises less than 20 amino acids.

9. The peptide of claim 1, wherein the amino acid sequence of $N^2$ comprises less than 10 amino acids.

10. A peptide comprising an amino acid segment comprising:
the amino acid sequence of GLEAS($N^1$)AYDGVEPS($N^2$) AYDGE,
an amino acid sequence at least about 90% identical to the amino acid sequence of GLEAS($N^1$)AYDGVEPS($N^2$) AYDGE, or
the amino acid sequence of GLEAS($N^1$)AYDGVEPS($N^2$) AYDGE having one or more conservative amino acid substitutions;
wherein $N^1$ and $N^2$ comprises an amino acid sequence,
wherein $N^1$ and $N^2$ do not comprise one or more of the amino acids A, C, I, F, L, P, S, T, or V.

11. The peptide of claim 10, wherein the amino acid sequence of $N^1$ comprises less than 100 amino acids.

12. The peptide of claim 10, wherein the amino acid sequence of $N^1$ comprises less than 50 amino acids.

13. The peptide of claim 11, wherein the amino acid sequence of $N^1$ comprises less than 20 amino acids.

14. The peptide of claim 10, wherein the amino acid sequence of $N^1$ comprises less than 10 amino acids.

15. The peptide of claim 10, wherein the amino acid sequence of $N^2$ comprises less than 100 amino acids.

16. The peptide of claim 10, wherein the amino acid sequence of $N^2$ comprises less than 50 amino acids.

17. The peptide of claim 10, wherein the amino acid sequence of $N^2$ comprises less than 20 amino acids.

18. The peptide of claim 10, wherein the amino acid sequence of $N^2$ comprises less than 10 amino acids.

19. The peptide of claim 10, wherein one or more of the amino acids is functionalized.

* * * * *